United States Patent
Feng et al.

(10) Patent No.: US 12,077,575 B2
(45) Date of Patent: Sep. 3, 2024

(54) HUMANIZED TETRA-SPECIFIC OCTAVALENT ANTIBODY AGAINST CLOSTRIDIUM DIFFICILE TOXIN A AND B

(71) Applicants: Hanping Feng, Ellicott City, MD (US); Yongrong Zhang, Columbia, MD (US); Zhiyong Yang, West Friendship, MD (US); Hua Yu, Columbia, MD (US); Yifan Zhang, North Potomac, MD (US)

(72) Inventors: Hanping Feng, Ellicott City, MD (US); Yongrong Zhang, Columbia, MD (US); Zhiyong Yang, West Friendship, MD (US); Hua Yu, Columbia, MD (US); Yifan Zhang, North Potomac, MD (US)

(73) Assignees: FZATA, INC., Halethorpe, MD (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 196 days.

(21) Appl. No.: 17/616,134

(22) PCT Filed: Jun. 3, 2020

(86) PCT No.: PCT/US2020/035925
§ 371 (c)(1),
(2) Date: Dec. 2, 2021

(87) PCT Pub. No.: WO2020/247500
PCT Pub. Date: Dec. 10, 2020

(65) Prior Publication Data
US 2022/0235120 A1    Jul. 28, 2022

Related U.S. Application Data

(60) Provisional application No. 62/856,493, filed on Jun. 3, 2019.

(51) Int. Cl.
*C07K 16/12* (2006.01)
*A61K 39/00* (2006.01)
*A61P 31/04* (2006.01)

(52) U.S. Cl.
CPC .......... *C07K 16/1282* (2013.01); *A61P 31/04* (2018.01); *A61K 2039/505* (2013.01); *C07K 2317/22* (2013.01); *C07K 2317/24* (2013.01)

(58) Field of Classification Search
CPC ............ C07K 16/1282; C07K 2317/22; C07K 2317/24; A61P 31/04; A61K 2039/505
See application file for complete search history.

(56) References Cited

U.S. PATENT DOCUMENTS

| 2016/0368972 A1 | 12/2016 | Shoemaker |
| 2017/0204169 A1 | 7/2017 | Shoemaker et al. |
| 2018/0244760 A1 | 8/2018 | Feng et al. |

FOREIGN PATENT DOCUMENTS

| WO | WO-2016/073562 A1 | 5/2016 | |
| WO | WO-2016127104 A2 * | 8/2016 | .............. A61P 31/04 |
| WO | WO-2017/066468 A1 | 4/2017 | |
| WO | WO-2019/094095 A1 | 5/2019 | |

OTHER PUBLICATIONS

Schmidt et al., "A Tetraspecific VHH-Based Neutralizing Antibody Modifies Disease Outcome in Three Animal Models of Clostridium difficile Infection," Clinical and Vaccine Immunology, Sep. 1, 2016, 23(9):774-784.

Yang et al., "A Novel Multivalent, Single-Domain Antibody Targeting TcdA and TcdB Prevents Fulminant Clostridium difficile Infection in Mice," Journal of Infectious Diseases, Mar. 27, 2014, 210(6):964-972.

Yang et al., "Intravenous adenovirus expressing a multi-specific, single-domain antibody neutralizing TcdA and TcdB protects mice from Clostridium difficile infection," Pathogens and Disease, Aug. 7, 2016, 74(7):ftw078, 1-8.

Li et al., "Single domain based bispecific antibody, Muc1-Bi-1, and its humanized form, Muc1-Bi-2, induce potent cancer cell killing in muc1 positive tumor cells", PLOS One. 13(1):e0191024, 14 pages (Jan. 22, 2018).

Vincke, Cecile et al., "General Stategy to Humanize a Camelid Single-domain Antibody and Identification of a Universal Humanized Nanobody Scaffold," The Journal of Biological Chemistry, vol. 284, No. 5, Jan. 30, 2009, pp. 3273-3284, XP009124408.

* cited by examiner

*Primary Examiner* — Mark Halvorson
*Assistant Examiner* — Dennis J Sullivan
(74) *Attorney, Agent, or Firm* — Foley & Lardner LLP

(57) ABSTRACT

Novel, antibody-based binding agents derived from camelid V$_H$H and human immunoglobulins are described. These binding agents recognize and bind with specificity to *Clostridium difficile* toxin A and/or toxin B and in some cases exhibit toxin neutralizing activity. These binding agents can be used to treat or prevent primary and recurrent CDI. The binding agents include humanized V$_H$H peptide monomers, linked groups of humanized V$_H$H peptide monomers, humanized V$_H$H peptide monomers joined to antibody Fc domains, and humanized V$_H$H peptide monomers joined to IgG antibodies.

19 Claims, 17 Drawing Sheets

Specification includes a Sequence Listing.

Figure 1

```
5D                  QVQLVESGGGLVQPGGSLRLSCEASGFTLDYYGIGWFRQPPGKEREAVSYISASA
Human IGHV3-23*01   EVQLLESGGGLVQPGGSLRLSCAASGFTFSSYAMSWVRQAPGKGLEWVSAISGSG
h5D                 EVQLLESGGGLVQPGGSLRLSCAASGFTLDYYGIGWFRQAPGKEREAVSYISASA
                    :***:************** *****:  *.:.*.** ***  * ** **.*

5D                  RTILYADSVKGRFTISRDNAKNAVYLQMNSLKREDTAVYYCARRRFSASSVNRWLAD
Human IGHV3-23*01   GSTYYADSVKGRFTISRDNSKNTLYLQMNSLRAEDTAVYYCAK--------------
h5D                 RTILYADSVKGRFTISRDNSKNTLYLQMNSLRAEDTAVYYCARRRFSASSVNRWLAD
                    :  **************:**::*******: *********:

5D                  DYDVWGRGTQVAVSS
Human IGHJ4*01      YFDYWGQGTLVTVSS
h5D                 DYDVWGQGTLVTVSS
                     **** ** * ***

E3                  QVQLVESGGGLVQTGGSLRLSCASSGSIAGFETVTWSRQAPGKSLQWVASMTKTN
Human IGHV3-23*01   EVQLLESGGGLVQPGGSLRLSCAASGFTFSSYAMSWVRQAPGKGLEWVSAISGSG
hE3                 EVQLLESGGGLVQPGGSLRLSCAASGSIAGFETVTWSRQAPGKSLQWVASMTKTN
                    :***:******** **********:**        :::* ******.*:**:::: :

E3                  -NEIYSDSVKGRFTISRDNAKNTVYLQMNSLKPEDTGVYFCKGPELRGQGIQVTVSS
Human IGHV3-23*01   GSTYYADSVKGRFTISRDNSKNTLYLQMNSLRAEDTAVYYCAK--------------
Human IGHJ4*01                                                     YFDYWGQGTLVTVSS
hE3                 -NEIYSDSVKGRFTISRDNSKNTVYLQMNSLRAEDTAVYYCKGPELRGQGTLVTVSS
                    .  *:******* *****:***;*******: ***.**;*      *** *****

AH3                 QVQLVETGGGLVQPGGSLRLSCAASGFTLDYSSIGWFRQAPGKEREGVSCISSS
Human IGHV3-23*01   EVQLLESGGGLVQPGGSLRLSCAASGFTFSSYAMSWVRQAPGKGLEWVSAISGS
hAH3                EVQLLESGGGLVQPGGSLRLSCAASGFTLDYSSIGWFRQAPGKEREGVSCISSS
                    :***:*; ******************:   ::.*.*****  * **.**.*

AH3                 GDSTKYADSVKGRFTTSRDNAKNTVYLQMNSLKPDDTAVYYCAAFRATMCGVFPLSPY
Human IGHV3-23*01   GGSTYYADSVKGRFTISRDNSKNTLYLQMNSLRAEDTAVYYCAK-------------
-
hAH3                GDSTKYADSVKGRFTISRDNSKNTLYLQMNSLRAEDTAVYYCAAFRATMCGVFPLSPY
                    *.** ********** ****:***:******; ;********

AH3                 GKDDWGKGTLVTVSS
Human IGHV3-23*01   ---------------
Human IGHJ4*01      YFDYWGQGTLVTVSS
hAH3                GKDDWGQGTLVTVSS
                      * ** ********

AA6                 QLQLVETGGGLVQPGGSLRLSCAASGFTFSDYVMTWVRQAPGKGPEWIATINTDG
Human IGHV3-23*01   EVQLLESGGGLVQPGGSLRLSCAASGFTFSSYAMSWVRQAPGKGLEWVSAISGSG
hAA6                EVQLLESGGGLVQPGGSLRLSCAASGFTFSDYVMTWVRQAPGKGPEWIATINTDG
                    ::**:* ******************** .*.*;********** **::;*. .*

AA6                 -STMRDDSTKGRFTISRDNAKNTLYLQMTSLKPEDTALYYCARGRVISASAIRGAVR
Human IGHV3-23*01   GSTYYADSVKGRFTISRDNSKNTLYLQMNSLRAEDTAVYYCAK--------------
Human IGHJ4*01                                                            YFDYW
hAA6                -STMRDDSTKGRFTISRDNSKNTLYLQMNSLRAEDTAVYYCARGRVISASAIRGAVR
                    **  **.*********:********.**; ****;****;

AA6                 GPGTQVTVSS
Human IGHV3-23*01   ----------
Human IGHJ4*01      GQGTLVTVSS
hAA6                GQGTLVTVSS
                     * ** *****
```

HUMANIZED TETRA-SPECIFIC OCTAVALENT ANTIBODY AGAINST CLOSTRIDIUM DIFFICILE TOXIN A AND B

CROSS-REFERENCE TO RELATED APPLICATIONS

This application is the U.S. National Stage of PCT/US2020/035925, filed Jun. 3, 2020, which claims priority to U.S. Provisional Application No. 62/856,493, filed Jun. 3, 2019.

STATEMENT OF FEDERALLY SPONSORED RESEARCH AND DEVELOPMENT

This invention was made with government support under Grant Number AI132207 awarded by the National Institutes of Health. The government has certain rights in the invention.

SEQUENCE LISTING

A sequence listing in electronic format (ASCII text file (is filed with this application and incorporated by reference. The name of the ASCII text file is sequence.txt; the file was created on Dec. 1, 2021, the size of the file is 61,805 bytes.

BACKGROUND

Camelid single-domain variable fragments of heavy-chain only antibodies ($V_HHs$) are evolving as a new group of therapeutic molecules with unique advantages resulting from their single domain nature, small size (15 kD), and ease of production and manipulation into various antibody formats, including multi-specificity. These advantages significantly expand their therapeutic potential over conventional monoclonal antibodies (Könning et al. 2017). The humanized camelid antibody Caplacizumab (Cablivi™, by Ablynx) was approved in the European Union for the treatment of thrombotic thrombocytopenic purpura and thrombosis in 2018. The recent high-profile acquisition of Ablynx (a company that develops $V_HH$ therapeutics) by Sanofi for €3.9 billion also portends the value of VHH therapeutics. By 2016, there were 142 therapeutic nanobodies under development, 12 of which were in clinical trials.

For VHH therapeutics, it is desirable to humanize camelid $V_HHs$ to reduce immunogenicity, especially those $V_HHs$ that require repeated administration or long term administration. Humanization is usually done via mutation-based methods (e.g. mutation scanning; resurfacing (Desmet et al. 2010); T-cell epitope removal (Roque-Navarro et al. 2003); complementarity determining region (CDR) grafting (Williams et al. 2010)). CDR grafting is the most commonly-used method to humanize antibodies; it was the method used to humanize murine antibody 4D5 (Carter et al. 1992), which was later developed into trastuzumab (Herceptin®) by Genentech. This method grafts the antigen-binding region to a human framework. The method is straightforward: unlike the resurfacing/B-cell epitope removal method, which may retain the T-cell epitopes (Roque-Navarro et al. 2003), CDR grafting allows the complete removal of immunogenicity from framework regions and a great reduction of immunogenicity from CDRs (Harding et al. 2010). Because camelid VHH CDRs are not well defined, the CDR grafting method for $V_HHs$ is not well-established. There is a need for humanized $V_HHs$ suitable for clinical use.

BRIEF SUMMARY OF INVENTION

The present invention provides, inter alia, tetra-specific, octavalent IgG1 molecules based on humanized VHH-antigen-binding blocks. A CDR (complementarity-determining region)-grafting method for humanizing camelid single-domain variable fragments of heavy-chain only antibodies ($V_HHs$) was used to improve $V_HH$-based therapeutics for use in clinical applications. As discussed below, VHH CDRs are defined based on the statistical distribution of antigen-contacting residues in $V_HHs$, which serves as a general guide for VHH humanization. The invention includes a specific antibody (designated as FZ003) that reacts to four non-overlapping epitopes with enhanced bio-activities, including neutralizing activity and broad reactivity.

Accurately defining CDRs is crucial to successfully humanize $V_HHs$ (Roguska et al. 1994; Roque-Navarro et al. 2003; Williams et al. 2010; Sela-Culang et al. 2013). Contrary to conventional antibodies, camelid VHH CDRs have not been well defined. Previous studies and recent findings have demonstrated that CDR definitions based on conventional antibodies cannot be simply adopted for $V_HHs$. However, with the availability of a large database of crystal structures of antibody-antigen complexes, one group recently defined conventional non-rabbit CDRs more accurately than ever before (Kunik et al. 2012), with only 2/166 antigen-contacting residues in the framework regions as demonstrated by an independent group (Olimpieri et al. 2013). Using a similar method, antigen-contacting residues in rabbit antibodies were identified and a CDR grafting approach was developed for the humanization of rabbit antibodies that has achieved a high success rate (Zhang and Ho 2017). This approach was extended and applied to defining CDRs for $V_HHs$ from camelid species, such as camel, alpaca and llama, and utilized to humanize $V_HHs$ with therapeutic potential against Clostridium difficile.

Camelid CDRs

In a first embodiment, the present invention is directed to the camelid (e.g., alpaca) CDRs shown in Table 1. Thus, the invention includes the peptide set forth in SEQ ID NO:14, the peptide set forth in SEQ ID NO:15, the peptide set forth in SEQ ID NO:16, the peptide set forth in SEQ ID NO:17, the peptide set forth in SEQ ID NO:18, the peptide set forth in SEQ ID NO:19, the peptide set forth in SEQ ID NO:20, the peptide set forth in SEQ ID NO:21, the peptide set forth in SEQ ID NO:22, the peptide set forth in SEQ ID NO:23, the peptide set forth in SEQ ID NO:24, and the peptide set forth in SEQ ID NO:25.

These CDRs comprise four different camelid VHH peptides that have binding specificity for C. difficile toxin A or toxin B. These CDRs can be put into human antibody frameworks, such as the DP47 framework, a human germ-line sequence, or the IGHV3-23*01 framework. The resulting humanized $V_HH$ peptides are also included within the scope of the invention.

TABLE 1

|  | CDR1 | CDR2 | CDR3 |
|---|---|---|---|
| Alpaca VHH 5D | GFTLDYYGIGWF (SEQ ID NO: 14) | EREAVSYISASARTILYADSVK (SEQ ID NO: 15) | ARRRESASSVNRWLADDYDVW (SEQ ID NO: 16) |
| Alpaca VHH E3 | GSIAGFETVTWS (SEQ ID NO: 17) | SLQWVASMTKTNNEIYSDSVK (SEQ ID NO: 18) | KGPELR (SEQ ID NO: 19) |
| Alpaca VHH AH3 | GFTLDYSSIGWF (SEQ ID NO: 20) | EREGVSCISSSGDSTKYADSVK (SEQ ID NO: 21) | AAFRATMCGVFPLSPYGKDDW (SEQ ID NO: 22) |
| Alpaca VHH AA6 | GFTFSDYVMTWV (SEQ ID NO: 23) | GPEWIATINTDGSTMRDDSTK (SEQ ID NO: 24) | ARGRVISASAIRGAVR (SEQ ID NO: 25) |

The present invention also includes sequence variants of these camelid CDRs, having at least 80% amino acid sequence identity over the entire length of the peptide sequence and retaining the toxin binding and/or neutralizing activity of the wild-type peptide. Thus, the invention includes variants having at least 80% sequence identity to the peptides set forth in SEQ ID NOs:14-25 wherein the variant retains the toxin binding and/or neutralizing activity of the wild-type peptide upon which it is based.

Camelid $V_HHs$

The present invention is further directed to four camelid (alpaca) VHH peptides termed 5D, E3, AH3 and AA6. The camelid $V_HH$ peptides have binding specificity for *C. difficile* toxin A or toxin B. The amino acid sequence encoding these peptides are provided in SEQ ID NO:26 (5D), SEQ ID NO:27 (E3), SEQ ID NO:28 (AH3), and SEQ ID NO:29 (AA6) and shown in FIG. 1. Thus, the invention includes the peptide set forth in SEQ ID NO:26, the peptide set forth in SEQ ID NO:27, the peptide set forth in SEQ ID NO:28, and the peptide set forth in SEQ ID NO:29.

The present invention also includes sequence variants of these camelid VHH peptides, having at least 80% amino acid sequence identity over the entire length of the peptide sequence and retaining the toxin binding and/or neutralizing activity of the wild-type peptide. Thus, the invention includes variants having at least 80% sequence identity to the peptides set forth in SEQ ID NOs:26-29 wherein the variant retains the toxin binding and/or neutralizing activity of the wild-type peptide upon which it is based.

Binding Agents

*C. difficile*-associated disease is mainly caused by two large exotoxins, i.e., toxin A (TcdA) and toxin B (TcdB), produced by the bacteria. These toxins are structurally similar, 300-kDa single-chain proteins that exhibit similar modes of action on host cells. Both toxins target host Rho GTPases, leading to enzyme inactivation, followed by cytoskeleton disorganization and apoptosis. In intestinal epithelial cells, TcdA catalyzes glucosylation of the Rho GTPases, leading to reorganization of the actin cytoskeleton with accompanying morphological changes such as complete rounding of cells and destruction of the intestinal barrier function. The toxins can individually cause CDI in animals, and TcdA⁻ TcdB⁻ strains of the bacteria are avirulent.

Systemic and mucosal antibodies against the toxins confer protection against CDI. Because TcdA and TcdB are essential virulence factors for *C. difficile*, antibodies produced against both toxins can treat and protect against toxigenic *C. difficile* infection in animal models.

The present invention, in part, builds on existing knowledge regarding anti-TcdA and anti-TcdB antibodies for the treatment and prevention of CDI, and the symptoms of CDI. Provided herein are novel, antibody-based binding agents derived from human and camelid immunoglobulins. These binding agents recognize and bind with specificity to *C. difficile* TcdA and/or TcdB. Some of these binding agents exhibit toxin-neutralizing activity. These binding agents can be used to treat or prevent primary and recurrent CDI, as well as the symptoms of primary and recurrent CDI.

Camelid animals produce a class of functional immunoglobulins that lack light chains and are thus heavy chain-only antibodies (HCAbs). The $V_H$ domain of HCAbs, called $V_HH$, is similar to the conventional human $V_H$ domain but has unique sequence and structural characteristics. DNA encoding this domain can be readily cloned and expressed in microbes to yield soluble protein monomers that retain the antigen-binding properties of the parent HCAb. These $V_HH$ peptide monomers are small (~15 kDa), easy to produce, and generally more stable than conventional antibody fragments. They can also be linked to other $V_HH$ peptide monomers, or produced as fusion proteins with human antibodies, such as IgG, and as fusion proteins with fragments of human antibodies, such as Fc domains. Because the $V_HH$ peptide monomers are derived from camelid animals, administration of the monomers and binding agents comprising the monomers to human subjects may induce an immune response against the proteins. Therefore, humanizing the $V_HH$ peptide monomers prior to the production of the fusion proteins allows for the production of binding agents with reduced immunogenicity versus non-humanized versions. Humanizing the $V_HH$ peptide monomers includes modifying the amino acid sequence of the monomers to increase the similarity of the peptides to antibody variants that naturally occur in humans. Alternatively, and as discussed above and utilized herein, humanized versions of the monomers are produced by CDR-grafting onto human antibody frameworks.

The binding agents of the present invention thus include humanized $V_HH$ peptide monomers and linked groups of humanized $V_HH$ peptide monomers (comprising 2, 3, 4, or more monomers), as well as more complex binding agents that comprise humanized $V_HH$ peptide monomers joined to antibody Fc domains, as well as humanized $V_HH$ peptide monomers joined to partial or full antibodies, where the antibodies are preferably IgG (such as IgG1, IgG2, IgG3, and IgG4), but also include IgM, IgA, IgD and IgE antibodies. The Fc domains and antibodies may be fully human or humanized antibodies as well. The binding agents are defined in the following paragraphs.

Humanized $V_HH$ Peptide Monomer Binding Agents

In a second embodiment, the present invention is directed to binding agents comprising humanized $V_HH$ peptide monomers and linked groups of humanized $V_HH$ peptide monomers comprising two (homo- and hetero-dimers), three (homo- and hetero-trimers), four (homo- and hetero-tetramers), or more monomers, each of which independently binds TcdA and/or TcdB, preferably with specificity. Thus, the invention encompasses $V_HH$ peptide binding agents comprising at least one humanized $V_HH$ peptide monomer, wherein each humanized $V_HH$ peptide monomer has binding specificity for a unique epitope of *C. difficile* toxin A (TcdA) or toxin B (TcdB). In certain aspects, these binding agents comprise two, three, four, or more linked humanized $V_HH$ peptide monomers. The humanized $V_HH$ peptide monomers include, but are not limited to, the humanized $V_HH$ peptide monomers h5D (SEQ ID NO:1), hE3 (SEQ ID NO:2), hAA6 (SEQ ID NO:3) and hAH3 (SEQ ID NO:4), shown in FIG. 1.

The present invention also includes sequence variants of the humanized $V_HH$ peptide monomers, having at least 80% amino acid sequence identity over the entire length of the $V_HH$ variant peptide sequence and retaining the toxin binding and/or neutralizing activity of the wild-type peptide. The variant amino acids of the sequence variants may be limited to the framework regions of the $V_HH$ peptide monomers, or limited to the CDRs of the $V_HH$ peptide monomers, or located in both regions. When compared to the corresponding non-humanized camelid $V_HH$ peptide sequence (i.e. SEQ ID NO:26 (5D), SEQ ID NO:27 (E3), SEQ ID NO:28 (AH3), and SEQ ID NO:29 (AA6)), the peptide sequence of the variant includes at least one amino acid difference.

In aspects of this embodiment where two or more monomers are linked, the monomers may be linked by flexible peptide linkers, generally comprising between 10 and 20 amino acids. Suitable linkers include, but are not limited to, linker-1 (SEQ ID NO:5) and linker-2 (SEQ ID NO:6).

In certain aspects of this embodiment, the binding agents bind to TcdA and/or TcdB with specificity. In certain aspects of this embodiment, the binding agents exhibit TcdA and/or TcdB neutralizing activity.

In a specific aspect of this embodiment, the binding agent comprises four linked humanized $V_HH$ peptide monomers where two of the monomers have binding specificity for epitopes of TcdA and two of the monomers have binding specificity for epitopes of TcdB. The epitopes of TcdA may be the same or different. The epitopes of TcdB may be the same or different.

Also included in the scope of the invention are isolated polynucleotide sequences comprising a nucleotide sequence encoding the binding agents comprising humanized $V_HH$ peptide monomers and linked groups of humanized $V_HH$ peptide monomers of the invention and complementary strands thereof. The invention further encompasses expression vectors comprising the isolated polynucleotide sequences. The invention also encompasses isolated host cells comprising one or more of the expression vectors of the invention. The invention further encompasses methods of producing a binding agent comprising culturing the isolated host cells under conditions promoting expression of the binding agent encoded by the expression vector, and recovering the binding agent from the cell culture.

$V_HH$-IgG Binding Agents

In a third embodiment, the invention is directed to binding agents comprising humanized $V_HH$ peptide monomers joined to substantial portions of IgG antibodies, where the binding agents bind TcdA and/or TcdB. In these IgG-based binding agents, the variable regions of the light and heavy chains of IgG antibodies are replaced by one, two, three, four or more of the humanized $V_HH$ peptide monomers. The IgG antibodies utilized may be fully human or humanized antibodies.

The invention includes sequence variants of the humanized $V_HH$-IgG binding agents, having at least 80% amino acid sequence identity over the entire length of the peptide sequence and retaining the toxin binding and/or neutralizing activity of the wild-type protein. The variant amino acids of the sequence variants may be limited to the framework regions of the $V_HH$ peptide monomers, or limited to the CDRs of the $V_HH$ peptide monomers, or limited to the IgG portions of the agents, or limited to a combination of the framework regions of the $V_HH$ peptide monomers and the IgG portions of the agents. When changes are present in the $V_HH$ peptide monomers, the peptide sequence of the monomer variant includes at least one amino acid difference in comparison to the corresponding non-humanized camelid $V_HH$ peptide sequence (i.e. SEQ ID NO:26 (5D), SEQ ID NO:27 (E3), SEQ ID NO:28 (AH3), or SEQ ID NO:29 (AA6)).

In certain aspects of this embodiment, the $V_HH$-IgG binding agents comprise two, three, four, or more linked humanized $V_HH$ peptide monomers joined to the amino termini of IgG light and heavy chains in place of the native variable regions. The humanized $V_HH$ peptide monomers include, but are not limited to, the humanized $V_HH$ peptide monomers h5D (SEQ ID NO:1), hE3 (SEQ ID NO:2), hAA6 (SEQ ID NO:3), and hAH3 (SEQ ID NO:4).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:5) and linker-2 (SEQ ID NO:6).

In a first sub-embodiment, the invention is directed to tetra-specific, octameric binding agents comprising substantial portions of an IgG antibody, two sets of linked first and second humanized $V_HH$ peptide monomers, and two sets of linked third and fourth humanized $V_HH$ peptide monomers, wherein the IgG antibody comprises two arms, each arm comprising a heavy chain lacking a variable region and a light chain lacking a variable region, and each chain having an amino terminus, wherein for each arm of the antibody, one set of linked first and second humanized $V_HH$ peptide monomers is joined to the amino terminus of the light chain, and one set of linked third and fourth humanized $V_HH$ peptide monomers is joined to the amino terminus of the heavy chain, and wherein the humanized $V_HH$ peptide monomers independently have binding specificity for an epitope of *Clostridium difficile* toxin A (TcdA) or toxin B (TcdB). This binding agent is termed "tetra-specific" as it recognizes four different toxin epitopes. It is termed "octameric" as it bears eight humanized $V_HH$ peptide monomers (two copies of the first monomer, two copies of the second monomer, two copies of the third monomer, and two copies of the fourth monomer).

In this sub-embodiment, the first, second, third and fourth humanized $V_HH$ peptide monomers each has binding specificity for a different epitope.

In certain aspects of this sub-embodiment, two of the humanized $V_HH$ peptide monomers have binding specificity for epitopes of TcdA and two of the humanized $V_HH$ peptide monomers have binding specificity for epitopes of TcdB.

In certain aspects of this sub-embodiment, the humanized $V_HH$ peptide monomers independently have binding specificity for an epitope in the glucosyltransferase domain, cysteine protease domain, translocation domain or receptor binding domain of TcdA or TcdB.

As this binding agent is an IgG-based binding agent, it will be clear to the skilled artisan that two heavy chain polypeptides and two light chain polypeptides, having the noted amino acid sequences, will assemble through disulfide bonding to provide the complete binding agent. One example of this binding agent is the FZ003 binding agent, based on IgG having a kappa light chain. The light chain of the FZ003 binding agent is provided in SEQ ID NO:8, and it is composed of humanized $V_HH$ peptide monomers hAA6 (SEQ ID NO:3) and hE3 (SEQ ID NO:2), wherein the peptide monomers are linked by linker-1 (SEQ ID NO:5). The remainder of the sequence is the IgG light chain sequence. The heavy chain of the FZ003 binding agent is provided in SEQ ID NO:9, and it is composed of humanized $V_HH$ peptide monomers hAH3 (SEQ ID NO:4) and h5D (SEQ ID NO:1), wherein the peptide monomers are linked by linker-1 (SEQ ID NO:5). The remainder of the sequence is the IgG heavy chain sequence. Sequence variants of these binding agents retain TcdA and/or TcdB binding specificity, or the sequence variants retain toxin-neutralizing activity, or both. The variant amino acids of the sequence variants may be limited to the framework regions of the $V_HH$ peptide monomers, or limited to the CDRs of the $V_HH$ peptide monomers, or limited to the IgG portions of the agents, or limited to a combination of the framework regions of the $V_HH$ peptide monomers and the IgG portions of the agents.

In a second sub-embodiment, the invention is directed to bi-specific or tetra-specific, tetrameric binding agents comprising substantial portions of an IgG antibody and first, second, third and fourth humanized $V_HH$ peptide monomers, wherein the IgG antibody comprises two arms, each arm comprising a heavy chain lacking a variable region and a light chain lacking a variable region, and each chain having an amino terminus, wherein for a first arm of the antibody, the first humanized $V_HH$ peptide monomer is joined to the amino terminus of the light chain, and the second humanized $V_HH$ peptide monomer is joined to the amino terminus of the heavy chain, wherein for a second arm of the antibody, the third humanized $V_HH$ peptide monomer is joined to the amino terminus of the light chain, and the fourth humanized $V_HH$ peptide monomer is joined to the amino terminus of the heavy chain, and wherein the humanized $V_HH$ peptide monomers independently have binding specificity for an epitope of *Clostridium difficile* toxin A (TcdA) or toxin B (TcdB). When the binding agent is "tetra-specific", it recognizes four different toxin epitopes; when "bi-specific" it recognizes two different toxin epitopes. The binding agents are "tetrameric" as they bear four humanized $V_HH$ peptide monomers (when bi-specific, the first and third monomer have the same sequence and bind the same epitope, and the second and fourth monomers have the same sequence and bind the same epitope; when tetra-specific, each of the monomers has a different sequence and binds a different epitope).

When the binding agent is bi-specific, the first and second monomers have binding specificity for different epitopes, the first and third monomers have identical amino acid sequences, and the second and fourth monomers have identical amino acid sequences. One of the humanized $V_HH$ peptide monomers may have binding specificity for an epitope of TcdA and one of the humanized $V_HH$ peptide monomers may have binding specificity for an epitope of TcdB.

When the binding agent is tetra-specific, each of the humanized $V_HH$ peptide monomers has binding specificity for a different epitope. Two of the humanized $V_HH$ peptide monomers may have binding specificity for epitopes of TcdA and two of the humanized $V_HH$ peptide monomers may have binding specificity for epitopes of TcdB.

In certain aspects of this sub-embodiment, each of the humanized $V_HH$ peptide monomers has binding specificity for epitopes of TcdA.

In certain aspects of this sub-embodiment, each of the humanized $V_HH$ peptide monomers has binding specificity for epitopes of TcdB.

In certain aspects of this sub-embodiment, the humanized $V_HH$ peptide monomers independently have binding specificity for an epitope in the glucosyltransferase domain, cysteine protease domain, translocation domain or receptor binding domain of TcdA or TcdB.

In certain aspects of this embodiment and the sub-embodiments, the binding agents bind to TcdA and/or TcdB with specificity. In certain aspects of this embodiment, the binding agents exhibit TcdA and/or TcdB neutralizing activity.

Also included in the scope of the invention are isolated polynucleotide sequences comprising a nucleotide sequence encoding the light chain arm of the humanized $V_HH$-IgG binding agents of the invention and complementary strands thereof. In one specific example, a light chain arm of a humanized $V_HH$-IgG binding agent of the invention is encoded by the nucleic acid sequence set forth in SEQ ID NO:10.

Also included in the scope of the invention are isolated polynucleotide sequences comprising a nucleotide sequence encoding the heavy chain arm of the humanized $V_HH$-IgG binding agents of the invention and complementary strands thereof. In one specific example, a heavy chain arm of a humanized $V_HH$-IgG binding agent of the invention is encoded by the nucleic acid sequence set forth in SEQ ID NO:11.

The invention further encompasses expression vectors comprising the isolated polynucleotide sequences. In one specific example, an expression vector encoding a light chain arm of a humanized $V_HH$-IgG binding agent of the invention comprises the nucleic acid sequence set forth in SEQ ID NO:12. In another specific example, an expression vector encoding a heavy chain arm of a humanized $V_HH$-IgG binding agent of the invention comprises the nucleic acid sequence set forth in SEQ ID NO:13. The invention also encompasses isolated host cells comprising one or more of the expression vectors of the invention. The invention further encompasses methods of producing a binding agent comprising culturing the isolated host cells under conditions promoting expression of the binding agent encoded by the expression vector, and recovering the binding agent from the cell culture.

$V_HH$-Fc Binding Agents

In a fourth embodiment, the invention is directed to binding agents comprising humanized $V_HH$ peptide monomers joined to antibody Fc domains, where the binding agents bind TcdA and/or TcdB. In these Fc domain-based binding agents, one, two, three, four or more of the humanized $V_HH$ peptide monomers are joined to the hinge, $C_H2$ and $C_H3$ regions of each arm of the Fc domain of an antibody heavy chain. Thus, the peptide monomers replace the Fab regions of an antibody. The Fc domains utilized may be fully human or humanized Fc domains.

The invention includes sequence variants of the $V_HH$-Fc binding agents, having at least 80% amino acid sequence identity over the entire length of the peptide sequence and retaining the toxin binding and/or neutralizing activity of the wild-type protein. The variant amino acids of the sequence variants may be limited to the framework regions of the $V_HH$ peptide monomers, or limited to the CDRs of the $V_HH$ peptide monomers, or limited to the Fc portions of the agents, or limited to a combination of the framework regions of the $V_HH$ peptide monomers and the Fc portions of the agents. When changes are present in the $V_HH$ peptide monomers, the peptide sequence of the monomer variant includes at least one amino acid difference in comparison to the corresponding non-humanized camelid $V_HH$ peptide sequence (i.e. SEQ ID NO:26 (5D), SEQ ID NO:27 (E3), SEQ ID NO:28 (AH3), or SEQ ID NO:29 (AA6)).

In certain aspects of this embodiment, these binding agents comprise two, three, four, or more linked humanized $V_HH$ peptide monomers joined to the amino termini of the arms of the Fc domains. The humanized $V_HH$ peptide monomers include, but are not limited to, the humanized $V_HH$ peptide monomers h5D (SEQ ID NO:1), hE3 (SEQ ID NO:2), hAA6 (SEQ ID NO:3) and hAH3 (SEQ ID NO:4).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:5) and linker-2 (SEQ ID NO:6).

In a first sub-embodiment, the invention is directed to tetra-specific, octameric binding agents comprising an antibody Fc domain and two sets of linked first, second, third and fourth humanized $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first, second, third and fourth humanized $V_HH$ peptide monomers is joined to the amino terminus of the arm, and where the humanized $V_HH$ peptide monomers independently have binding specificity for an epitope of *Clostridium difficile* toxin A (TcdA) or toxin B (TcdB). This binding agent is termed "tetra-specific" as it recognizes four different toxin epitopes. It is termed "octameric" as it bears eight humanized $V_HH$ peptide monomers (two copies of the first monomer, two copies of the second monomer, two copies of the third monomer, and two copies of the fourth monomer).

In certain aspects of this sub-embodiment, the first, second, third and fourth humanized $V_HH$ peptide monomers each has binding specificity for a different epitope.

In certain aspects of this sub-embodiment, two of the humanized $V_HH$ peptide monomers have binding specificity for epitopes of TcdA and two of the humanized $V_HH$ peptide monomers have binding specificity for epitopes of TcdB.

In certain aspects of this sub-embodiment, the humanized $V_HH$ peptide monomers independently have binding specificity for an epitope in the glucosyltransferase domain, cysteine protease domain, translocation domain or receptor binding domain of TcdA or TcdB.

The variant amino acids of the sequence variant may be located in framework regions of the humanized $V_HH$ peptide monomers.

In a second sub-embodiment, the invention is directed to bi-specific, tetrameric binding agents comprising an antibody Fc domain and two sets of linked first and second humanized $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first and second humanized $V_HH$ peptide monomers is joined to the amino terminus of the arm, and where the humanized $V_HH$ peptide monomers have binding specificity for an epitope of *Clostridium difficile* toxin A (TcdA) or toxin B (TcdB). This binding agent is termed "bi-specific" as it recognizes two different toxin epitopes. It is termed "tetrameric" as it bears four humanized $V_HH$ peptide monomers (two copies of the first monomer, and two copies of the second monomer).

In certain aspects of this sub-embodiment, the first and second humanized $V_HH$ peptide monomers have binding specificity for the same or different epitopes.

In certain aspects of this sub-embodiment, the humanized $V_HH$ peptide monomers independently have binding specificity for an epitope in the glucosyltransferase domain, cysteine protease domain, translocation domain or receptor binding domain of TcdA or TcdB.

In certain aspects of this embodiment and the sub-embodiments, the binding agents bind to TcdA and/or TcdB with specificity. In certain aspects of this embodiment, the binding agents exhibit TcdA and/or TcdB neutralizing activity.

The invention includes epitope binding fragments of each the binding agents provided in the various embodiments and aspects defined herein.

The invention includes pharmaceutical formulations comprising one or more of the binding agents defined herein and a pharmaceutically acceptable carrier or diluent.

Also included in the scope of the invention are isolated polynucleotide sequences comprising a nucleotide sequence encoding the light chain arm of the humanized $V_HH$-Fc binding agents of the invention and complementary strands thereof.

Also included in the scope of the invention are isolated polynucleotide sequences comprising a nucleotide sequence encoding the heavy chain arm of the humanized $V_HH$-Fc binding agents of the invention and complementary strands thereof.

The invention further encompasses expression vectors comprising the isolated polynucleotide sequences. The invention also encompasses isolated host cells comprising one or more of the expression vectors of the invention. The invention further encompasses methods of producing a binding agent comprising culturing the isolated host cells under conditions promoting expression of the binding agent encoded by the expression vector, and recovering the binding agent from the cell culture.

Methods of Treatment

In a fifth embodiment, the invention is directed to methods of treating or preventing a disease symptom induced by *C. difficile* in a subject comprising administering a therapeutically-effective amount of one or more binding agents as defined herein to a subject having *C. difficile* infection or a risk of developing *C. difficile* infection. In some aspects of the embodiment, the *C. difficile* infection is a primary infection. In other aspects, the *C. difficile* infection is a recurrent infection. In certain embodiments, the binding agent is the FZ003 binding agent.

In a sixth embodiment, the invention is directed to methods of neutralizing *C. difficile* toxin TcdA and/or TcdB in a subject infected by *C. difficile* comprising administering a therapeutically-effective amount of one or more binding agents as defined herein to a subject having *C. difficile* infection. In some aspects of the embodiment, the *C. difficile* infection is a primary infection. In other aspects, the *C. difficile* infection is a recurrent infection. In certain embodiments, the binding agent is the FZ003 binding agent.

In a seventh embodiment, the invention is directed to methods of treating or preventing *C. difficile* infection in a subject comprising administering a therapeutically-effective amount of one or more of the binding agents as defined herein to a subject having *C. difficile* infection or a risk of developing *C. difficile* infection. In some aspects of the embodiment, the *C. difficile* infection is a primary infection.

In other aspects, the *C. difficile* infection is a recurrent infection. In certain embodiments, the binding agent is the FZ003 binding agent.

In certain aspects of the sixth embodiment, the method further comprises administering a therapeutically-effective amount of an antibiotic (and/or other therapeutic for treating or preventing *C. difficile* infection) to the subject.

In certain aspects of each of the methods described herein, the binding agent is in a pharmaceutical formulation comprising the binding agent and a pharmaceutically acceptable carrier or diluent.

In certain aspects of each of the methods described herein, the therapeutically-effective amount of the binding agent is from 10 ug/kg to 100 mg/kg of the agent per body weight of the subject.

In certain aspects of each of the methods described herein, the agent is administered to the subject orally, parenterally or rectally.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 1 provides the amino acid sequences for four camelid (alpaca) $V_HH$ peptides termed 5D (SEQ ID NO:26), E3 (SEQ ID NO:27), AH3 (SEQ ID NO:28) and AA6 (SEQ ID NO:29). The amino acid sequences of the four humanized versions of these $V_HH$ peptides, namely h5D (SEQ ID NO:1), hE3 (SEQ ID NO:2), hAA6 (SEQ ID NO:3) and hAH3 (SEQ ID NO:4), are provided as well. The amino acid sequences for human IGHV3-23*01 (SEQ ID NO:30) and human IGHJ4*01 (SEQ ID NO:31) are provided as well.

DETAILED DESCRIPTION OF THE INVENTION

I. Definitions

Figure 2:
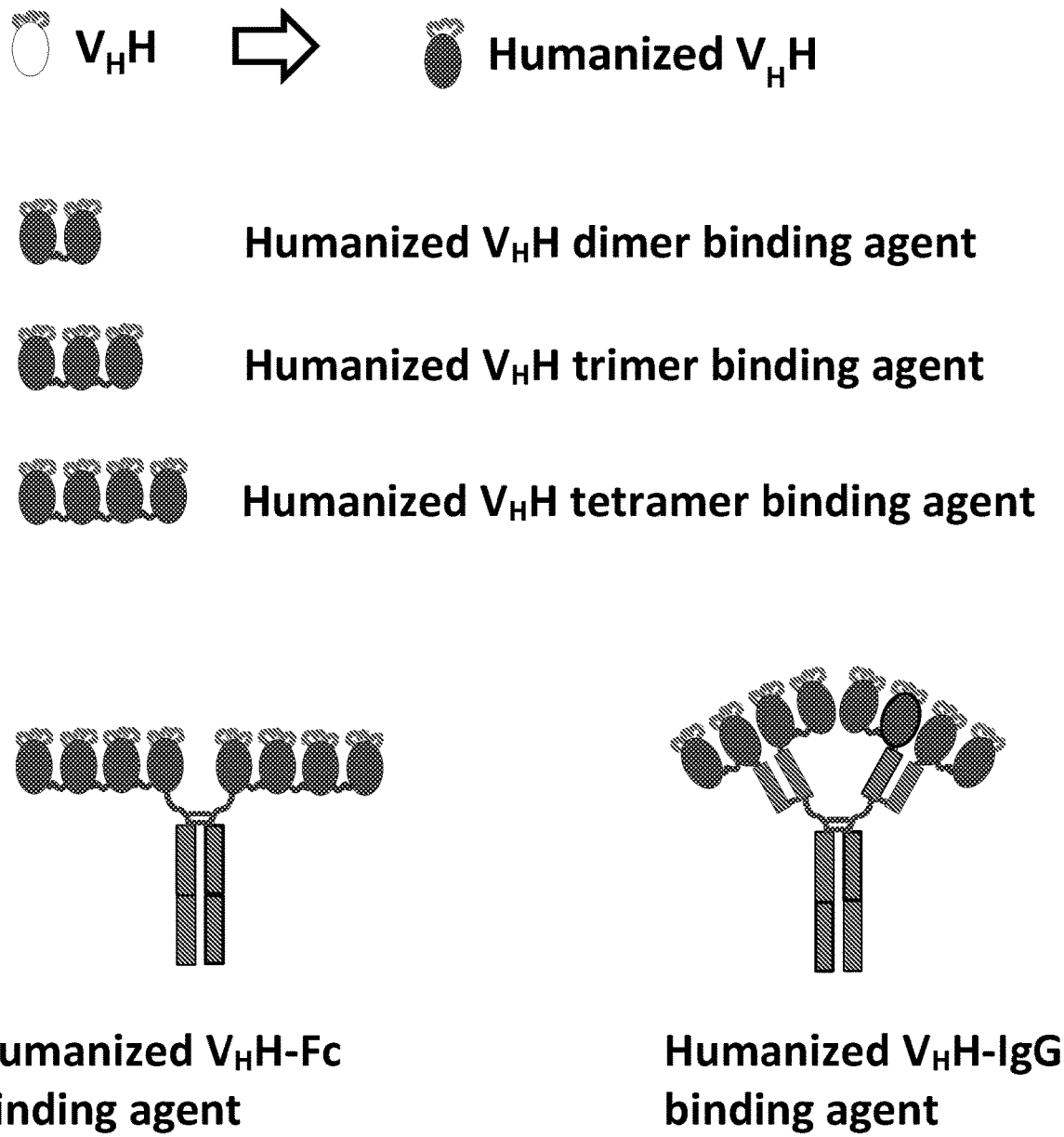
FIG. 2 provides schematic images of humanized $V_HH$ binding agents of the invention.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

The primary effectors of CDI in animals are the *C. difficile* exotoxins TcdA and TcdB (toxin A and B). These toxins are structurally similar, 300-kDa single-chain proteins that exhibit similar modes of action on host cells. Both toxins target host Rho GTPases, leading to enzyme inactivation, followed by cytoskeleton disorganization and apoptosis. In intestinal epithelial cells, TcdA catalyzes glucosylation of the Rho GTPases, leading to reorganization of the actin cytoskeleton with accompanying morphological changes such as complete rounding of cells and destruction of the intestinal barrier function. The toxins can individually cause CDI in animals, and TcdA⁻ TcdB⁻ strains of the bacteria are avirulent.

Numerous independent studies have demonstrated that systemic and mucosal antibodies against the toxins confer protection against CDI. Because TcdA and TcdB are essential virulence factors for *C. difficile*, antibodies produced against both toxins can protect against toxigenic *C. difficile* infection in animal models. In humans, high serum levels of antitoxin antibodies are associated with reduced disease severity and incidence of relapse. Therefore, a preventative rationale for systemically and orally administered antitoxin antibodies exists. However, monoclonal antibodies targeting a single epitope are typically low affinity, and use of such antibodies runs the risk of inducing mutations within the epitopes of the toxins thereby creating additional strains. Thus, neutralizing antitoxins targeting multiple, key, and conserved toxin epitopes are highly desirable.

Camelid animals produce a class of functional immunoglobulins that lack light chains and are thus heavy chain-only antibodies (HCAbs). Camelid HCAbs bind to target antigens with binding properties equivalent to those achieved by conventional human IgG. The $V_H$ region of HCAbs, called $V_HH$, is similar to conventional $V_H$ domains but has unique sequence and structural characteristics. DNA encoding this domain can readily be cloned and expressed in microbes to yield soluble protein monomers retaining the antigen-binding properties of the parent HCAb. These $V_HH$ peptide monomer binding agents are small (~15 kDa), easy to produce, and generally more stable than conventional antibody fragments.

The present invention utilizes the advantageous characteristics of HCAbs in the production of humanized $V_HH$ peptide monomers and binding agents based thereon that can be used in the treatment and prevention of CDI. $V_HH$ peptide monomers were screened for TcdA and TcdB epitope recognition and binding, and the binding agents of the invention are based on versions of those that exhibited TcdA and/or TcdB binding specificity, or TcdA and/or TcdB neutralizing activity, or both such binding specificity and neutralizing activity, humanized using the methods defined herein.

Two major hurdles for repeated and/or long-term in vivo use of $V_HH$ peptide monomers are their likely short half-life and potential immunogenicity. As to the first hurdle, the $V_HH$ monomers can be fused with human IgG and Fc domains, as discussed herein, which serves to increase their valency and circulating half-life.

With respect to the second hurdle, because the $V_HH$ peptide monomers are derived from camelid animals, there is the possibility that administration of the monomers and binding agents comprising the monomers to human subjects could induce an immune response against the proteins. Due to their small size and the high degree of identity of their framework regions to the human $V_H$ framework of family III, the $V_HH$ peptide monomers are expected to exhibit low immunogenicity when administered to humans. Indeed, systemic application of small monovalent $V_HH$ monomers seems to induce little, if any, neutralizing antibody responses. However, protein immunogenicity generally increases with size and complexity. To address possible immunogenicity in IgG- and Fc-based binding agents, the $V_HH$ monomers are humanized as using CDR-grafting techniques without compromising their expression level, affinity, solubility, and stability. The final product has a good expression, stability, and solubility similar to human IgG1 s, while retaining the antigen specificity and affinity of the loop donor $V_HH$ peptide.

Humanized $V_HH$ monomers that gain highest identity to human $V_H$ gene(s) and possess the highest binding/neutralizing activity were selected, after which they were transformed into the $V_HH$-Fc and $V_HH$-IgG constructs to generate fully humanized binding agents of the invention. The protein sequences of these binding agents can be essentially identical to that of a human antibody variant, despite the non-human origin of some of the CDR segments that are responsible for the ability of the binding agent to bind to its target antigen. Therefore, this strategy decreases the chance for potential immunogenicity in vivo and thus increase their safety and half-life in vivo.

Those humanized $V_HH$ monomers that exhibit epitope binding and toxin-neutralizing activity were linked to produce some of the binding agents of the invention. The binding agents include simple humanized $V_HH$ peptide monomers and linked groups of humanized $V_HH$ peptide monomers (comprising 2, 3, 4, or more monomers), as well as more complex binding agents that comprise humanized $V_HH$ peptide monomers joined to antibody Fc domains, and humanized $V_HH$ peptide monomers joined to portions of IgG antibodies (FIG. 2).

$V_HH$ Monomers & $V_HH$ Dimers

The inventors established an efficient platform to screen $V_HH$ monomers against specific domains of both *C. difficile* toxins. Using highly immunogenic atoxic holotoxins for immunization, and bioactive chimeric toxins (with normal domain functions) for screening, panels of $V_HH$ monomers binding to different domains of TcdA or TcdB were prepared. A majority of these $V_HH$ monomers possessed potent neutralizing activity and their binding to specific domains was determined.

Several of the $V_HH$ monomers bind to highly conserved TcdA/TcdB epitopes. For example, the E3 $V_HH$ monomer (SEQ ID NO:27) binds to the Rho GTPase binding site and blocks glucosylation; the AH3 $V_HH$ monomer (SEQ ID NO:28) binds to the GT domain of the toxin; the 7F $V_HH$ monomer binds to cysteine protease cleavage sites and blocks GT domain cleavage and release. Some $V_HH$ monomers have potent toxin neutralizing activity, capable of blocking toxin cytotoxic activity at nM concentrations.

These $V_HH$ monomers were then used in the production of the humanized $V_HH$ monomers defined herein, using the CDR-grafting technique also defined herein. Humanized versions of each of the $V_HH$ monomers 5D (SEQ ID NO:26), E3 (SEQ ID NO:27), AH3 (SEQ ID NO:28) and AA6 (SEQ ID NO:29) were prepared, resulting in the humanized $V_HH$ monomers h5D (SEQ ID NO:1), hE3 (SEQ ID NO:2), hAA6 (SEQ ID NO:3) and hAH3 (SEQ ID NO:4). See FIG. 1.

The present invention thus includes each of the humanized $V_HH$ peptide monomers h5D (SEQ ID NO:1), hE3 (SEQ ID NO:2), hAA6 (SEQ ID NO:3) and hAH3 (SEQ ID NO:4). The invention also includes sequence variants of the humanized $V_HH$ peptide monomers having at least 80%, 81%, 82%, 83%, 84%, 85%, 86%, 87%, 88%, 89%, 90%, 91%, 92%, 93%, 94%, 95%, 96%, 97%, 98%, or 99% sequence identity over the entire length of the $V_HH$ variant peptide sequence and retaining the toxin binding and/or neutralizing activity of the wild-type humanized peptide. The variant amino acids of the sequence variants may be limited to the framework regions of the $V_HH$ peptide monomers, or limited to the CDRs of the $V_HH$ peptide monomers, or located in both the framework regions and the CDRs of the $V_HH$ peptide monomers. The variants of the humanized $V_HH$ peptide monomers have at least one amino acid difference in comparison to the corresponding non-humanized camelid $V_HH$ peptide sequence (i.e. SEQ ID NO:26 (5D), SEQ ID NO:27 (E3), SEQ ID NO:28 (AH3), and SEQ ID NO:29 (AA6)). Thus, the variants do not encompass the original non-humanized camelid $V_HH$ peptide monomers.

The present invention also includes polynucleotide sequences encoding each of the humanized $V_HH$ peptide monomers and the sequence variants thereof, as well as complementary strands thereof.

To enhance the binding activity of the peptide monomers, humanized $V_HH$ peptide homo- and hetero-dimer binding agents were created, where two humanized $V_HH$ peptide monomers are linked. Homodimer binding agents comprise two identical monomers (e.g. h5D-h5D) that bind identical epitopes on two different toxins. Heterodimer binding agents comprise two different monomers (e.g. h5D-hE3) that bind two distinct epitopes of the same toxin or distinct epitopes on two different toxins.

The humanized $V_HH$ monomers in the homo- and heterodimers are linked using a short, flexible linker of between 10 and 20 amino acids. Suitable linkers include those provided in Table 2.

TABLE 2

| Name | SEQ ID NO. for Amino Acid Seq. |
|---|---|
| Linker-1 | 5 |
| Linker-2 | 6 |

It will be understood by the skilled artisan that minor changes can be made to the sequence of the flexible linker without departing from the properties of the peptide. Sequence variants of the flexible linker having at least 90%, 91%, 92%, 93%, 94%, 95%, 96%, 97%, 98%, or 99% sequence identity over the entire length of the peptide sequence and retaining properties of the linker upon which they are based may thus be used.

The present invention includes humanized $V_HH$ peptide homodimer binding agents comprising pairs of any of the monomers h5D, hE3, hAA6 and hAH3 or variants thereof as defined herein, where at least one of the monomers is a humanized monomer, linked by a flexible linker as defined above. The present invention also includes humanized $V_HH$ peptide heterodimer binding agents comprising any combination of two of the monomers h5D, hE3, hAA6 and hAH3 or variants thereof as defined herein, where at least one of the monomers is a humanized monomer, linked by a flexible linker as defined above.

The present invention also includes sequence variants of the humanized $V_HH$ peptide homo- and hetero-dimers having at least 80%, 81%, 82%, 83%, 84%, 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The variant amino acids of the sequence variants may be limited to the framework regions of the humanized $V_HH$ peptide monomers, or limited to the CDRs of the humanized $V_HH$ peptide monomers, or located in both the framework regions and the CDRs of the humanized $V_HH$ peptide monomers. The variants of the humanized $V_HH$ peptide dimers have at least one amino acid difference in at least one monomer sequence in comparison to the corresponding non-humanized camelid $V_HH$ peptide sequence (i.e. SEQ ID NO:26 (5D), SEQ ID NO:27 (E3), SEQ ID NO:28 (AH3), and SEQ ID NO:29 (AA6)).

The present invention further includes polynucleotide sequences encoding each the humanized $V_HH$ peptide homo-hetero-dimers and the sequence variants thereof, as well as complementary strands thereof.

The invention also includes humanized $V_HH$ peptide homo- and hetero-trimer binding agents where three monomers are linked using the flexible linkers defined above in Table 2, where at least one of the monomers is a humanized monomer. Any combination of the monomers h5D, hE3, hAA6 and hAH3 may be used, including trimers comprising three copies of the same monomer, trimers comprising two copies of one monomer and a single copy of another, and trimers comprising three different monomers. Sequence variants of the humanized $V_HH$ peptide homo- and heterotrimers are included in the invention, having at least 80%, 81%, 82%, 83%, 84%, 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The variant amino acids of the sequence variants may be limited to the framework regions of the humanized $V_HH$ peptide monomers, or limited to the CDRs of the humanized $V_HH$ peptide monomers, or located in both the framework regions and the CDRs of the humanized $V_HH$ peptide monomers. The variants of the humanized $V_HH$ peptide trimers have at least one amino acid difference in at least one monomer sequence in comparison to the corresponding non-humanized camelid $V_HH$ peptide sequence (i.e. SEQ ID NO:26 (5D), SEQ ID NO:27 (E3), SEQ ID NO:28 (AH3), and SEQ ID NO:29 (AA6)).

The present invention further includes polynucleotide sequences encoding each the humanized $V_HH$ peptide homo-hetero-trimers and the sequence variants thereof, as well as complementary strands thereof.

hABAB

The invention encompasses binding agents comprising four linked humanized $V_HH$ peptide monomers that can simultaneously neutralize both *C. difficile* TcdA and TcdB. By creating tetra-specific binding agents that recognize and bind two epitopes on each of the toxins, the binding and neutralizing activity of the proteins might be strengthened. Therefore, four-domain (tetra-specific) humanized $V_HH$ binding agents may be generated.

The tetra-specific, tetrameric binding agents can be prepared from any combination of the monomers h5D, hE3, hAA6 and hAH3 or variants thereof as defined herein, where the monomers are linked using the flexible linkers of Table 2, where at least one of the monomers is a humanized monomer. In certain aspects, two, three or all four of the monomers is a humanized monomer. These binding agents will range from those having four copies of the same monomer, to those having three copies of the same monomer, to those having two copies of the same monomer, to those having four unique monomers, and variations therein. Sequence variants of the tetramers are included in the invention, having at least 80%, 81%, 82%, 83%, 84%, 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The variant amino acids of the sequence variants may be limited to the framework regions of the humanized $V_HH$ peptide monomers, or limited to the CDRs of the humanized $V_HH$ peptide monomers, or located in both the framework regions and the CDRs of the humanized $V_HH$ peptide monomers. The variants of the humanized $V_HH$ peptide tetramers have at least one amino acid difference in at least one monomer sequence in comparison to the corresponding non-humanized camelid $V_HH$ peptide sequence (i.e. SEQ ID NO:26 (5D), SEQ ID NO:27 (E3), SEQ ID NO:28 (AH3), and SEQ ID NO:29 (AA6)).

The present invention further includes polynucleotide sequences encoding each tetramer and the sequence variants thereof, as well as complementary strands thereof.

An exemplary binding agent of the invention comprises four linked humanized $V_HH$ monomers, each of which has binding specificity for a different epitope of TcdA or TcdB. Such a binding agent, termed hABAB, is a tetra-specific, tetrameric binding agent that consists of four distinct neutralizing humanized $V_HH$ monomers, two against TcdA and two against TcdB. This structural feature allows hABAB to bind simultaneously to two distinct neutralizing epitopes on each toxin.

hABAB binding agent can be prepared by linking humanized $V_HH$ monomers hAH3, h5D, hE3, and hAA6 using flexible linkers (Table 2). In one embodiment, humanized $V_HH$ peptide monomers hAH3 and hAA6 are separated by placing the h5D between them because hAH3 and hAA6 bind to GT and TD respectively, which are spatially distant to each other. This design may allow hAH3 and hAA6 to bind to TcdA simultaneously.

For the sake of clarity it can be noted that as used herein, "mono-specific", "bi-specific", "tri-specific", "tetra-specific", etc., mean the particular binding agent binds to 1, 2, 3, 4, etc., different epitopes, respectively. As used herein, "monomeric", "dimeric", "trimeric", "tetrameric", etc., mean that the particular binding agent has 1, 2, 3, 4, etc., separate humanized $V_HH$ peptide monomers that bind to the epitopes, respectively. Thus, a mono-specific, dimeric binding agent would display two humanized $V_HH$ peptide monomers that bind to the same epitope (e.g., a homodimer), and a bi-specific, dimeric binding agent would have two humanized $V_HH$ peptide monomers that bind to two different epitopes (e.g., a heterodimer). A tetra-specific, octameric binding agent has eight humanized $V_HH$ peptide monomers that recognize four different epitopes.

$V_HH$-Fc

It is well known that chimeric Fc-fusion proteins have the potential of increasing the half-life of a protein in vivo. This strategy has been applied in several FDA approved drugs, such as Etanercept. A proof-of principle study has shown that single-chain antibodies can be correctly assembled and expressed by B cells of transgenic mice carrying a mini-Ig construct encoding a dromedary $V_HH$ and the Fc domain of human IgG. Also, a chimeric anti-EGFR/EGFRvIII $V_HH$, EG2-Fc exhibited excellent tumor accumulation in vivo and has pharmacokinetic properties that could improve glioblastoma targeting.

The present invention includes binding agents comprising humanized $V_HH$ peptide monomers joined to antibody Fc domains ($V_HH$-Fc), where the binding agents bind TcdA and/or TcdB. In these Fc domain-based binding agents, one, two, three, four or more of the humanized $V_HH$ peptide monomers are joined to the hinge, $C_H2$ and $C_H3$ regions of the Fc domain of an antibody heavy chain. Thus, the peptide monomers replace the Fab regions of the antibody.

The humanized $V_HH$ peptide monomers may be any of h5D (SEQ ID NO:1), hE3 (SEQ ID NO:2), hAA6 (SEQ ID NO:3) and hAH3 (SEQ ID NO:4) or variants thereof as defined herein. Where two or more monomers are linked, the monomers may be linked by flexible peptide linkers, generally comprising between 10 and 20 amino acids. Suitable linkers include those linkers provided in Table 2.

While the $V_HH$-Fc will typically be composed of two identical chains that self-assemble intracellularly after production, the invention also includes $V_HH$-Fc binding agents comprising two different Fc chains. In such circumstances, the sequence of the humanized $V_HH$ monomer(s) alone may differ between the two Fc chains, or the Fc chains themselves may differ in sequence, or both the $V_HH$ monomer(s) and the Fc chains may differ in sequence.

One type of $V_HH$-Fc binding agent is an octameric (also referred to as "octavalent") binding agent comprising an antibody Fc domain and first, second, third and fourth humanized $V_HH$ peptide monomers, where at least one of the monomers is a humanized monomer, where the humanized $V_HH$ peptide monomers have binding specificity for an epitope of *Clostridium difficile* toxin A (TcdA) or toxin B (TcdB), where the first, second, third and fourth humanized $V_HH$ peptide monomers are linked together and joined to amino termini of both antibody Fc domains, and where the antibody Fc domain comprises the hinge, $C_H2$ and $C_H3$ regions of an antibody heavy chain. Because this binding agent has four humanized $V_HH$ peptide monomers, it can be mono-specific (where all of the monomers bind the same epitope), bi-specific (where the monomers bind two different epitopes), tri-specific (where the monomers bind three different epitopes), or tetra-specific (where the monomers bind four different epitopes). In certain aspects, two, three or all four of the monomers is a humanized monomer. The humanized $V_HH$ peptide monomers may be any of h5D, hE3, hAA6 and hAH3 or variants thereof as defined herein.

A specific example of a tetra-specific $V_HH$-Fc binding agent is the hABAB-Fc binding agent, a tetra-specific, octameric binding agent comprising an antibody Fc domain and two sets of linked first, second, third and fourth humanized V$_H$H peptide monomers, wherein the antibody Fc domain comprises two arms, each arm comprising hinge, C$_H$2 and C$_H$3 regions of an antibody heavy chain, and each arm having an amino terminus, wherein for each arm of the Fc domain, one set of linked first, second, third and fourth humanized V$_H$H peptide monomers is joined to the amino terminus of the arm, and where the humanized V$_H$H peptide monomers have binding specificity for an epitope of *Clostridium difficile* toxin A (TcdA) or toxin B (TcdB). This binding agent is termed "tetra-specific" as it recognizes four different toxin epitopes. It is termed "octameric" as it bears eight humanized V$_H$H peptide monomers (two copies of the first monomer, two copies of the second monomer, two copies of the third monomer, and two copies of the fourth monomer). The humanized V$_H$H peptide monomers may be any of h5D, hE3, hAA6 and hAH3 or variants thereof as defined herein.

hABAB-Fc binding agent may be prepared by generating an expression vector encoding the humanized V$_H$H peptide monomers hAH3/h5D/hAA6/hE3 (linked in the noted order) joined to a human IgG1 Fc domain. The humanized V$_H$H peptide monomers may be separated by flexible linkers of Table 2. Upon self-assembly of pairs of the chains after expression, the tetra-specific, octameric binding agent results. The invention includes the hABAB-Fc binding agent and sequence variants having at least 80%, 81%, 82%, 83%, 84%, 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The variant amino acids of the sequence variants may be limited to the framework regions of the V$_H$H peptide monomers, or limited to the CDRs of the V$_H$H peptide monomers, or limited to the Fc portions of the agents, or limited to a combination of the framework regions of the V$_H$H peptide monomers and the Fc portions of the agents. When changes are present in the V$_H$H peptide monomers, the peptide sequence of the monomer variant includes at least one amino acid difference in comparison to the corresponding non-humanized camelid V$_H$H peptide sequence (i.e. SEQ ID NO:26 (5D), SEQ ID NO:27 (E3), SEQ ID NO:28 (AH3), or SEQ ID NO:29 (AA6)).

The present invention further includes polynucleotide sequences encoding these sequence variants and complementary strands thereof.

Specific pairings with one monomer include: h5D-Fc+ h5D-Fc; hE3-Fc+hE3-Fc; hAA6-Fc+hAA6-Fc; hAH3-Fc+ hAH3-Fc; h5D-Fc+hE3-Fc; h5D-Fc+hAA6-Fc; h5D-Fc+ hAH3-Fc; hE3-Fc+hAA6-Fc; hE3-Fc+hAH3-Fc; and hAA6-Fc+hAH3-Fc. Specific pairings with two monomers include: hAH3-h5D-Fc+hAH3-h5D-Fc; hAA6-hE3-Fc+ hAA6-hE3-Fc; and hAH3-h5D-Fc+hAA6-hE3-Fc.

Bi-specific, tetrameric V$_H$H-Fc binding agents can be produced comprising an antibody Fc domain and two sets of linked first and second humanized V$_H$H peptide monomers, wherein the antibody Fc domain comprises two arms, each arm comprising hinge, C$_H$2 and C$_H$3 regions of an antibody heavy chain, and each arm having an amino terminus, wherein for each arm of the Fc domain, one set of linked first and second humanized V$_H$H peptide monomers is joined to the amino terminus of the arm, and where the humanized V$_H$H peptide monomers have binding specificity for an epitope of *Clostridium difficile* toxin A (TcdA) or toxin B (TcdB). This binding agent is termed "bi-specific" as it recognizes two different toxin epitopes. It is termed "tetrameric" as it bears four humanized V$_H$H peptide monomers (two copies of the first monomer, and two copies of the second monomer). The first and second humanized V$_H$H peptide monomers may have binding specificity for the same or different epitopes. The humanized V$_H$H peptide monomers may independently have binding specificity for an epitope in the glucosyltransferase domain, cysteine protease domain, translocation domain or receptor binding domain of TcdA or TcdB. The humanized V$_H$H peptide monomers may be any of h5D, hE3, hAA6 and hAH3 or variants thereof as defined herein.

The V$_H$H-Fc binding agents bind to TcdA and/or TcdB with specificity. In certain aspects of the invention, the binding agents exhibit TcdA and/or TcdB neutralizing activity.

V$_H$H-IgG

The present invention also includes binding agents comprising humanized V$_H$H peptide monomers joined to more of an antibody that the Fc domain alone. For example, V$_H$H-IgG binding agents comprise one, two, three, four or more of the humanized V$_H$H peptide monomers are joined to the light (kappa or lambda) and heavy chains of an IgG antibody lacking the variable regions of the antibody. Thus, the peptide monomers replace the variable regions of the antibody. In addition to IgG (including IgG1, IgG2, IgG3, and IgG4), other antibodies can be used as the basis for the binding agents, such as IgM, IgA, IgD and IgE.

The humanized V$_H$H peptide monomers may be any of the h5D (SEQ ID NO:1), hE3 (SEQ ID NO:2), hAA6 (SEQ ID NO:3) and hAH3 (SEQ ID NO:4) humanized V$_H$H peptide monomers or variants thereof as defined herein. Where two or more monomers are linked, the monomers may be linked by flexible peptide linkers, generally comprising between 10 and 20 amino acids. Suitable linkers include those linkers provided in Table 2.

V$_H$H-IgG binding agents include octameric binding agents comprising an IgG antibody and first, second, third and fourth humanized V$_H$H peptide monomers, wherein the humanized V$_H$H peptide monomers have binding specificity for an epitope of *Clostridium difficile* toxin A (TcdA) or toxin B (TcdB), wherein first and second humanized V$_H$H peptide monomers are linked together and joined to amino termini of both light chains of the antibody, wherein the light chains lack the antibody variable regions, and wherein third and fourth humanized V$_H$H peptide monomers are linked together and joined to amino termini of both heavy chains of the antibody, wherein the heavy chains lack the antibody variable regions. Because this binding agent has four humanized V$_H$H peptide monomers, it can be mono-specific (where all of the monomers bind the same epitope), bi-specific (where the monomers bind two different epitopes), tri-specific (where the monomers bind three different epitopes), or tetra-specific (where the monomers bind four different epitopes). In one specific example, the V$_H$H-IgG binding agents of the invention comprise the V$_H$H peptide monomers h5D (SEQ ID NO:1), hE3 (SEQ ID NO:2), hAA6 (SEQ ID NO:3) and hAH3 (SEQ ID NO:4).

A specific example of a tetra-specific V$_H$H-IgG binding agent is the ABAB-IgG binding agent, a tetra-specific, octameric binding agent comprising an IgG antibody, two sets of linked first and second humanized V$_H$H peptide monomers, and two sets of linked third and fourth humanized V$_H$H peptide monomers, wherein the IgG antibody comprises two arms, each arm comprising a heavy chain lacking a variable region and a light chain lacking a variable region, and each chain having an amino terminus, wherein for each arm of the antibody, one set of linked first and second humanized V$_H$H peptide monomers is joined to the amino terminus of the light chain, and one set of linked third and fourth humanized $V_HH$ peptide monomers is joined to the amino terminus of the heavy chain, and wherein the humanized $V_HH$ peptide monomers have binding specificity for an epitope of *Clostridium difficile* toxinA (TcdA) or toxin B (TcdB). This binding agent is termed "tetra-specific" as it recognizes four different toxin epitopes. It is termed "octameric" as it bears eight humanized $V_HH$ peptide monomers (two copies of the first monomer, two copies of the second monomer, two copies of the third monomer, and two copies of the fourth monomer). In certain aspects, the first, second, third and fourth humanized $V_HH$ peptide monomers may each have binding specificity for a different epitope. In certain aspects, two of the humanized $V_HH$ peptide monomers may have binding specificity for epitopes of TcdA and two of the humanized $V_HH$ peptide monomers may have binding specificity for epitopes of TcdB. In certain aspects, the humanized $V_HH$ peptide monomers independently have binding specificity for an epitope in the glucosyltransferase domain, cysteine protease domain, translocation domain or receptor binding domain of TcdA or TcdB. The humanized $V_HH$ peptide monomers may be any of h5D, hE3, hAA6 and hAH3 or variants thereof as defined herein. In one specific example, the ABAB-IgG binding agents of the invention comprise the $V_HH$ peptide monomers h5D (SEQ ID NO:1), hE3 (SEQ ID NO:2), hAA6 (SEQ ID NO:3) and hAH3 (SEQ ID NO:4).

The invention includes $V_HH$-IgG binding agent and sequence variants having at least 80%, 81%, 82%, 83%, 84%, 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The variant amino acids of the sequence variants may be limited to the framework regions of the $V_HH$ peptide monomers, or limited to the CDRs of the $V_HH$ peptide monomers, or limited to the IgG portions of the agents, or limited to a combination of the framework regions of the $V_HH$ peptide monomers and the IgG portions of the agents. When changes are present in the $V_HH$ peptide monomers, the peptide sequence of the monomer variant includes at least one amino acid difference in comparison to the corresponding non-humanized camelid $V_HH$ peptide sequence (i.e. SEQ ID NO:26 (5D), SEQ ID NO:27 (E3), SEQ ID NO:28 (AH3), or SEQ ID NO:29 (AA6)).

A specific example of an ABAB-IgG binding agent of the invention is the FZ003 binding agent, based on IgG antibody having a kappa light chain. The light chain of the FZ003 binding agent is provided in SEQ ID NO:8, and it is composed of humanized $V_HH$ peptide monomers hAA6 (SEQ ID NO:3) and hE3 (SEQ ID NO:2), wherein the peptide monomers are linked by linker-1 (SEQ ID NO:5). The remainder of the sequence is the IgG light chain sequence. The heavy chain of the FZ003 binding agent is provided in SEQ ID NO:9, and it is composed of humanized $V_HH$ peptide monomers hAH3 (SEQ ID NO:4) and h5D (SEQ ID NO:1), wherein the peptide monomers are linked by linker-1 (SEQ ID NO:5). The remainder of the sequence is the IgG heavy chain sequence.

Bi-specific or tetra-specific, tetrameric IgG binding agents are included in the invention. Such binding agents comprise an IgG antibody and first, second, third and fourth humanized $V_HH$ peptide monomers, wherein the IgG antibody comprises two arms, each arm comprising a heavy chain lacking a variable region and a light chain lacking a variable region, and each chain having an amino terminus, wherein for a first arm of the antibody, the first humanized $V_HH$ peptide monomer is joined to the amino terminus of the light chain, and the second humanized $V_HH$ peptide monomer is joined to the amino terminus of the heavy chain, wherein for a second arm of the antibody, the third humanized $V_HH$ peptide monomer is joined to the amino terminus of the light chain, and the fourth humanized $V_HH$ peptide monomer is joined to the amino terminus of the heavy chain, and where the humanized $V_HH$ peptide monomers have binding specificity for an epitope of *Clostridium difficile* toxin A (TcdA) or toxin B (TcdB). When the binding agent is "tetra-specific", it recognizes four different toxin epitopes; when "bi-specific" it recognizes two different toxin epitopes. The binding agents "tetrameric" as they bear four humanized $V_HH$ peptide monomers (when bi-specific, the first and second monomer have the same sequence and bind the same epitope, and the third and fourth monomers have the same sequence and bind the same epitope; when tetra-specific, each of the monomers has a different sequence and binds a different epitope).

When the binding agent is bi-specific, the first and third monomers have binding specificity for different epitopes, the first and second monomers have identical amino acid sequences, and the third and fourth monomers have identical amino acid sequences. In certain aspects, one of the humanized $V_HH$ peptide monomers has binding specificity for an epitope of TcdA and one of the humanized $V_HH$ peptide monomers has binding specificity for an epitope of TcdB.

When the binding agent is tetra-specific, each of the humanized $V_HH$ peptide monomers has binding specificity for a different epitope. In certain aspects, two of the humanized $V_HH$ peptide monomers have binding specificity for epitopes of TcdA and two of the humanized $V_HH$ peptide monomers have binding specificity for epitopes of TcdB.

In certain aspects, each of the humanized $V_HH$ peptide monomers has binding specificity for epitopes of TcdA. In other aspects, each of the humanized $V_HH$ peptide monomers has binding specificity for epitopes of TcdB.

In certain aspects, the humanized $V_HH$ peptide monomers independently have binding specificity for an epitope in the glucosyltransferase domain, cysteine protease domain, translocation domain or receptor binding domain of TcdA or TcdB.

Antibody Fragments

The binding agents of the invention include epitope binding fragments of each of the humanized $V_HH$-Fc and $V_HH$-IgG binding agents defined herein. Because the humanized $V_HH$-Fc and $V_HH$-IgG binding agents are comparable in structure to human IgG antibodies, where the variable regions are replaced by the humanized $V_HH$ monomers, terms for human antibody fragments are also applicable to the such binding agents. The fragments include, but are not limited to, Fab fragments, F(ab')$_2$ fragments, single chain Fv (scFv) antibodies, and fragments produced by a Fab expression library, as well as bi-specific antibody and triple-specific antibodies.

The humanized $V_HH$-Fc and $V_HH$-IgG binding agents of the invention include fully human binding agents. The binding agents may be monoclonal or polyclonal. Further, the binding agents may be recombinant binding agents.

The binding agents may be produced in any species of animal, though preferably from a mammal such as a human, simian, mouse, rat, rabbit, guinea pig, horse, cow, sheep, goat, pig, dog or cat. For example, the binding agents can be human or humanized, or any binding agent preparation suitable for administration to a human.

Polynucleotide, Expression Vectors, Host Cells and Method of Making

The invention includes polynucleotides comprising nucleotide sequences encoding each the binding agents provided herein, as well as complementary strands thereof. A specific example is the polynucleotide sequences encoding the FZ003 binding agent defined above. The light chain comprises the nucleotide sequence set forth in SEQ ID NO:10. The heavy chain comprises the nucleotide sequence set forth in SEQ ID NO:11.

The invention also includes expression vectors comprising the polynucleotides, and host cells comprising the expression vectors. Suitable expression vectors include, e.g., pcDNA3.1 and pSec-His. Suitable host cells include, e.g., Chinese hamster ovary cells (CHO cells) and human embryonic kidney cells 293 (HEK 293 cells).

With respect to the FZ003 binding agent, the light and heavy chain sequences were separately inserted into the pHy expression vector. The complete sequence of the resulting light-chain encoding expression vector is provided in SEQ ID NO:12. The complete sequence of the resulting heavy-chain encoding expression vector is provided in SEQ ID NO:13.

The invention further includes methods of producing the binding agents defined herein, comprising culturing the host cells under conditions promoting expression of the binding agents encoded by the expression vectors, and recovering the binding agents from the cell cultures.

Methods of Treatment and Prevention

The binding agents of the invention can be used in methods of treating or preventing a disease symptom induced by *C. difficile* in a subject. These methods generally comprise administering a therapeutically-effective amount of one or more binding agents as defined herein to a subject having *C. difficile* infection or a risk of developing *C. difficile* infection.

The binding agents of the invention can also be used in of neutralizing *C. difficile* toxin TcdA and/or TcdB in a subject infected by *C. difficile*. These methods generally comprise administering a therapeutically-effective amount of one or more binding agents as defined herein to a subject having *C. difficile* infection.

The binding agents of the invention can further be used in methods of treating *C. difficile* infection in a subject. These methods generally comprise administering a therapeutically-effective amount of one or more of the binding agents as defined herein to a subject having *C. difficile* infection. These same methods can be used to treat CDI, as defined herein.

The binding agents can also be used in immunoprophylaxis in order to prevent immediate CDI threats. In addition, passive immunoprophylaxis can be used to prevent both immediate and longer-term CDI threats. Each approach has its own particular advantages and is suitable to target a particular high-risk population. These methods generally comprise administering a therapeutically-effective amount of one or more of the binding agent as defined herein to a subject a risk of developing *C. difficile* infection.

Each of the methods of the invention may include administration of the one or more binding agents in a pharmaceutical formulation comprising the binding agents and a pharmaceutically acceptable carrier or diluent.

In aspects of each of these methods, the binding agent is the FZ003 binding agent.

As used herein, the terms "neutralize" and "neutralizing" have their ordinary and customary meanings, and include one or more of: blocking, ameliorating, or decreasing in severity the activity of *C. difficile* TcdA and/or TcdB; and/or partly or fully inhibiting the activity of *C. difficile* TcdA and/or TcdB in a subject. Such neutralizing is by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, 10%, 5% or 1% versus a subject in which the methods of the present invention have not been practiced.

As used herein, the terms "treat", "treating", and "treatment" have their ordinary and customary meanings, and include one or more of: blocking, ameliorating, or decreasing in severity and/or frequency a symptom of a *C. difficile* infection or a *C. difficile*-related disease in a subject; and/or partly or fully inhibiting the biological activity and/or promoting the immunologic clearance of *C. difficile* TcdA and/or TcdB in a subject infected with *C. difficile*; and/or growth, division, spread, or proliferation of *C. difficile* cells or a *C. difficile* infection in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, 10%, 5% or 1% versus a subject in which the methods of the present invention have not been practiced.

As used herein, the terms "prevent", "preventing" and "prevention" have their ordinary and customary meanings, and include one or more of, stopping, averting, avoiding, alleviating or blocking *C. difficile* from colonizing, developing or progressing in a subject; and/or partly or fully inhibiting the biological activity and/or toxic effects of TcdA and/or TcdB in a subject infected with *C. difficile*; and/or stopping, averting, avoiding, alleviating or blocking the growth, division, spread, or proliferation of bacterial cells or bacterial infection in a subject. Prevention means stopping by at least about 95% versus a subject to which the prevention has not been administered. Preferably, the stopping is about 100%, about 99%, about 98%, about 97%, about 96% or about 95%. The results of the prevention may continue for a period of days (such as 1, 2, 3, 4, 5, 6 or 7 days), weeks (such as 1, 2, 3 or 4 weeks) or months (such as 1, 2, 3, 4, 5, 6 or more months).

The method of treating and preventing provided herein can be supplemented by also administering a therapeutically-effective amount of an antibiotic to the subject. Preferably, the antibiotic will have antibacterial activity against *C. difficile*.

Pharmaceutical Formulations

While the binding agents may be administered directly to a subject, the methods of the present invention are preferably based on the administration of a pharmaceutical formulation comprising one or more binding agents and a pharmaceutically acceptable carrier or diluent. Thus, the invention includes pharmaceutical formulations comprising one or more of the binding agents defined herein and a pharmaceutically acceptable carrier or diluent.

Pharmaceutically acceptable carriers and diluents are commonly known and will vary depending on the particular binding agent being administered and the mode of administration. Examples of generally used carriers and diluents include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising binding agents will typically have been prepared and cultured in the absence of any non-human components, such as animal serum (e.g., bovine serum albumin).

Pharmaceutical formulations comprising one or more binding agents may be administered to a subject using modes and techniques known to the skilled artisan. Characteristic of CDI disease may make it more amenable to treatment and prevention using colonic delivery of therapeutic agents, i.e., targeted delivery of binding agents to the lower GI tract, e.g., the large intestine or colon. For example, the binding agents described herein may be delivered to the gastrointestinal tract of a subject in need thereof using a yeast oral/gastrointestinal delivery system as described in U.S. Pat. App. Pub. No. US2018/0319872, herein incorporated by reference in its entirety. Other modes of delivery include, but are not limited to, oral, anal, via intravenous injection or aerosol administration. Other modes include, without limitation, intradermal, subcutaneous (s.c., s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids).

Depending on the means of administration, the dosage may be administered all at once, such as with an oral formulation in a capsule or liquid, or slowly over a period of time, such as with an intramuscular or intravenous administration.

The amount of binding agents, alone or in a pharmaceutical formulation, administered to a subject is an amount effective for the treatment or prevention of infection. Thus, therapeutically effective amounts are administered to subjects when the methods of the present invention are practiced. In general, from about 1 ug/kg to about 1000 mg/kg of the binding agent per body weight of the subject is administered. Suitable ranges also include from about 50 ug/kg to about 500 mg/kg, and from about 10 ug/kg to about 100 mg/kg. However, the amount of binding agent administered to a subject will vary between wide limits, depending upon the location, source, extent and severity of the infection, the age and condition of the subject to be treated, etc. A physician will ultimately determine appropriate dosages to be used.

Administration frequencies of the binding agents and pharmaceutical formulations comprising the binding agents will vary depending on factors that include the location of the bacterial infection, the particulars of the infection to be treated or prevented, and the mode of administration. Each formulation may be independently administered 4, 3, 2 or once daily, every other day, every third day, every fourth day, every fifth day, every sixth day, once weekly, every eight days, every nine days, every ten days, bi-weekly, monthly and bi-monthly.

The duration of treatment or prevention will be based on location and severity of the infection being treated or the relative risk of contracting the infection, and will be best determined by the attending physician. However, continuation of treatment is contemplated to last for a number of days, weeks, or months.

In each embodiment and aspect of the invention, the subject is a human, a non-human primate, bird, pig, horse, cow, goat, sheep, a companion animal, such as a dog, cat or rodent, or other mammal. The subjects to which the methods of the present invention can be applied include subjects having an underlying disease or condition that makes them more susceptible to *C. difficile* infections.

The invention also provides a kit comprising one or more containers filled with one or more binding agents or pharmaceutical formulations comprising binding agents. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human or animal administration.

Expression, Purification and Evaluation of Binding Agents

A variety of selection criteria may be used to select the binding agents defined herein. First, each of the constructs defined herein can be used in transient transfections of 293T cells for making small-scale recombinant proteins by Protein A affinity chromatography. The production yield of each construct can be determined by quantitative ELISA. Second, binding activity of recombinant proteins can be screened using ELISA and surface plasmon resonance (SPR) to select constructs that preserve their original binding activities against the toxins. Third, the proteins can be evaluated for neutralizing activity in in vitro assays. From the in vitro assays, candidate binding agents can be evaluated for their in vivo toxicity, serum half-life, and immunogenicity.

Accumulating observations indicate that polyreactivity and/or autoreactivity of in vivo recombinant binding agents are potential issues related to their in vivo safety and half-life. The application of the binding agents as a systemic binding agent for preventing primary acute CDI likely requires that the chimeric and humanized proteins are limited in polyreactivity and/or autoreactivity. Progress in protein proteomics has made it possible to screen for polyreactivity and autoreactivity of recombinant antibodies in vitro, which is a great tool for surrogate therapeutic antibodies. Therefore, selected humanized binding agents with good yield, high binding affinity, and potent neutralizing activity can be further tested for potential polyreactivity and autoreactivity using the auto-antigen microarray test and ProtoArray protein microarrays (Invitrogen).

III. Examples

Production of Camelid $V_HH$ Peptides

A panel of $V_HH$ peptides against *C. difficile* toxins TcdA and TcdB were generated using phage display (Yang et al. 2014; Li et al. 2015; Yang et al. 2016).

Analysis of Camelid $V_HH$ Peptides

Analysis of the generated $V_HH$ peptides revealed that several had potent neutralizing activities and therapeutic potential as described in previous publications (Yang et al. 2014; Li et al. 2015; Yang et al. 2016). Candidate $V_HHs$ with highest neutralizing activities were selected (5D and E3 against TcdB, and AA6 and AH3 against TcdA).

Mutation Scanning Humanization Strategy

To reduce possible immunogenicity and increase therapeutic potential, select humanized $V_HHs$ peptides were generated. A mutation scanning humanization strategy was initially adopted for the four most neutralizing $V_HHs$, two against TcdA and two against TcdB. Using this method, amino acids were identified within the $V_HH$ frameworks, amino acids that are different from homologous human germline VHs. Individual $V_HHs$ containing point mutations were generated and tested; those that retained wild-type binding affinity and neutralizing activity were considered to be permissive mutations. Those point mutations that reduced $V_HH$ binding and neutralizing activities were considered to be non-permissive mutations. A final humanized $V_HH$ contained all permissive amino acid sequences from the human V$_H$ framework and maintained similar binding affinity and neutralizing activity as the wild type counterpart.

On average, 10-15 mutations were tested for each V$_H$H, as exemplified by E3 (an anti-TcdB V$_H$H). Interestingly, mutation scanning identified several key amino acid residues (e.g. 51Q in V$_H$H E3) outside of the IMGT or Kabat defined CDRs in conventional antibodies. Crystal structural analysis of E3-TcdB binding domain complex confirmed that these amino acid residues indeed are involved in antigen contact. Finally, the mutation scanning allowed permissive mutations to be identified. The humanized E3 containing all these permissive mutations was found to have comparable TcdB-binding and neutralizing activity as wild-type E3. Using this strategy, MS (mutation scanning) humanized 5D (anti-TcdB; SEQ ID NO:32), E3 (anti-TcdB; SEQ ID NO:33), AA6 (anti-TcdA; SEQ ID NO:34) and AH3 (anti-TcdA; SEQ ID NO:35) were generated.

Analysis of Humanized V$_H$H Peptides Produced Using Mutation Scanning

Figure 3:
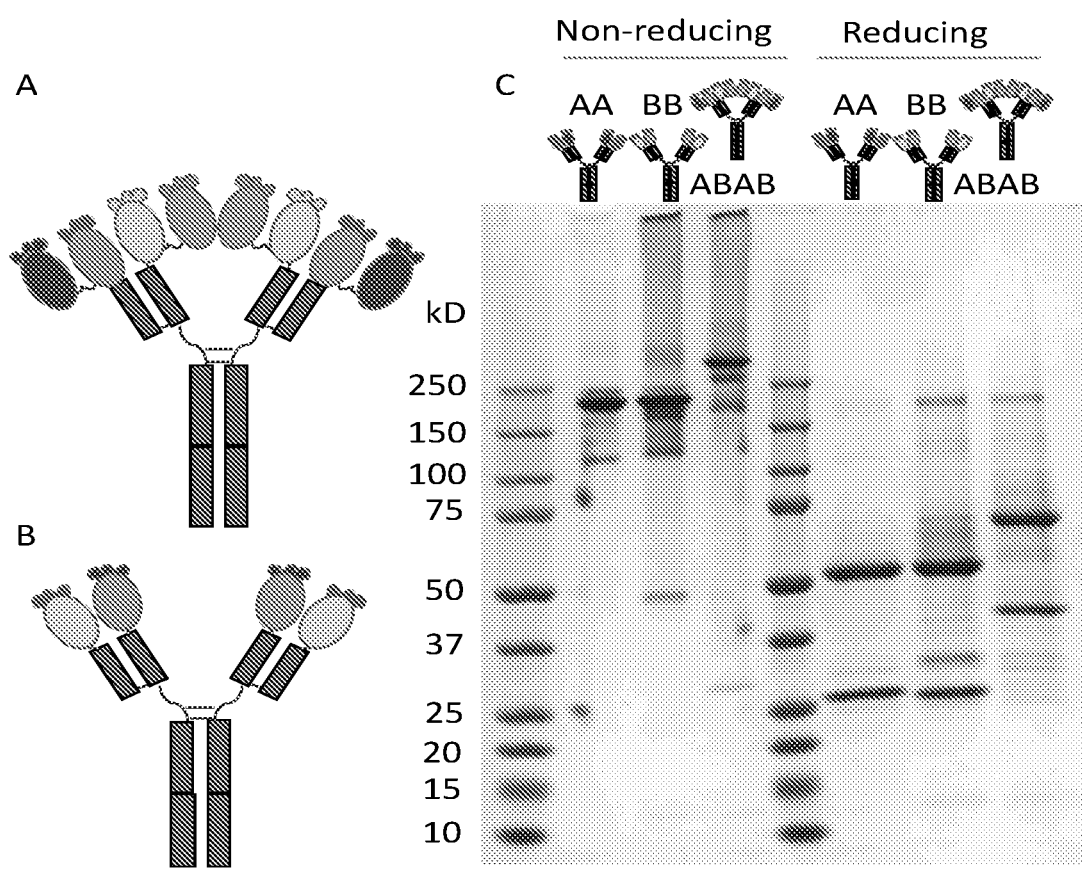
FIG. 3 provides the constructs (A) tetra-specific IgG1 and (B) bi-specific IgG1, and (C) SDS-PAGE of bi-specific IgG1 (AA and BB) and tetra-specific IgG1 (ABAB).

Whether the humanized antitoxin V$_H$Hs could be adapted to generate bi-specific and tetra-specific IgG1 binding agents as diagrammed in FIG. 3B, A, respectively, was investigated.

It was found that the humanized bispecific AA-IgG1 (recognizing two different TcdA epitopes), BB-IgG1 (recognizing two different TcdB epitopes), and tetra-specific ABAB-IgG1 humanized by mutation scanning (designated "FZ001"; recognizing two different TcdA epitopes and two different TcdB epitopes) could be efficiently expressed in CHO cells using standard techniques and that these antibody molecules displayed typical light and heavy chains in an SDS gel (FIG. 3C). The amino acid sequence of the FZ001 light chain (MShAA6-MShE3) is provided in SEQ ID NO:36. The amino acid sequence of the FZ001 heavy chain (MShAH3-MShSD) is provided in SEQ ID NO:37. The nucleic acid sequence of the FZ001 light chain (MShAA6-MShE3) is provided in SEQ ID NO:38. The nucleic acid sequence of the FZ001 heavy chain (MShAH3-MShSD) is provided in SEQ ID NO:39.

CDR Grafting Humanization Strategy

Although the mutation scanning methods described above were used to successfully humanized the four noted V$_H$H peptides, this approach required generating a large number of constructs with point mutations and it was a slow and labor-intensive process. CDR grafting, however, is a simpler and more straightforward method; however, this method requires that the CDRs can be accurately defined. Therefore, the following CDR-grafting based method for humanizing V$_H$Hs was developed.

First, a non-redundant structure database comprising all available unique V$_H$H-antigen complex structures for each V$_H$H peptide sequence was generated. The antigen contacting residues in the V$_H$H peptides of the database were identified in order to generate a contact map for each structure of V$_H$H peptide-antigen complex. This allowed the antigen-contacting residues to be identified and CDRs were defined as regions that contain all antigen-contacting residues.

Using this technique, the four humanized V$_H$H peptides h5D (SEQ ID NO:1), hE3 (SEQ ID NO:2), hAA6 (SEQ ID NO:3) and hAH3 (SEQ ID NO:4) were produced from the four camelid (alpaca) V$_H$H peptides 5D (SEQ ID NO:26), E3 (SEQ ID NO:27), AH3 (SEQ ID NO:28) and AA6 (SEQ ID NO:29). These humanized peptides (SEQ ID NOs:1-4) had sequences that differed from the humanized peptides that resulted from the mutation scanning strategy discussed above.

Production and Analysis of FZ003

The alpaca V$_H$H CDRs defined above for E3, 5D, AA6, and AH3 were also grafted into the IGHV3-23*01 antibody framework and a tetra-specific, octameric V$_H$H-IgG1 binding agent, designated as FZ003, was prepared.

In particular, FZ003 was constructed by two plasmids containing light chain constant region fused to 5D and AH3, and a heavy chain constant region fused to E3 and AA6. The plasmids (pHy vector) were then used to transfect mammalian cell lines (CHO or HEK cells) to produce FZ003 using standard approaches.

The light chain of the FZ003 binding agent is provided in SEQ ID NO:8, and it is composed of humanized V$_H$H peptide monomers hAA6 (SEQ ID NO:3) and hE3 (SEQ ID NO:2), wherein the peptide monomers are linked by linker-1 (SEQ ID NO:5). The remainder of the sequence is the IgG light chain sequence. The nucleotide sequence encoding the light chain is provided in SEQ ID NO:10.

The heavy chain of the FZ003 binding agent is provided in SEQ ID NO:9, and it is composed of humanized V$_H$H peptide monomers hAH3 (SEQ ID NO:4) and h5D (SEQ ID NO:1), wherein the peptide monomers are linked by linker-1 (SEQ ID NO:5). The remainder of the sequence is the IgG heavy chain sequence. The nucleotide sequence encoding the light chain is provided in SEQ ID NO:11.

The light and heavy chain sequences were separately inserted into the pHy expression vector. The complete sequence of the resulting light-chain encoding expression vector is provided in SEQ ID NO:12. The complete sequence of the resulting heavy-chain encoding expression vector is provided in SEQ ID NO:13.

Figure 4:
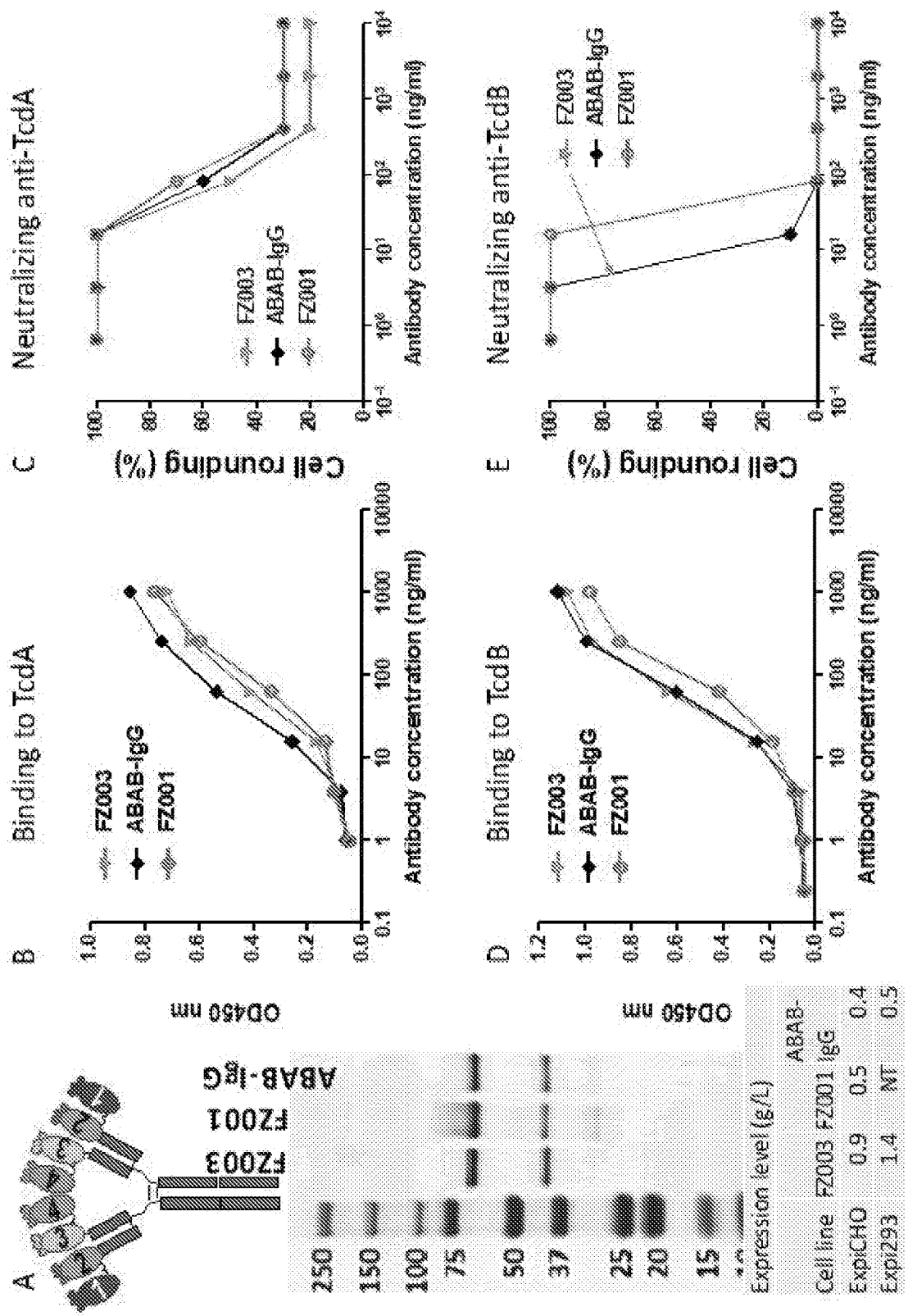
FIG. 4 provides the characterizations of the tetra-specific, octameric $V_HH$ binding agents against *C. difficile* TcdA and TcdB. ABAB-IgG contains alpaca $V_HH$s, FZ001 contains humanized $V_HH$s generated by mutation scanning, FZ003 contains CDR-grafted humanized $V_HH$s. (A) The construct, SDS-PAGE of purified proteins and the expression level of these construct in mammalian cell lines are shown. The numbered part is the $V_HH$: 1 and 4 target TcdA, 2 and 3 target TcdB. (B) The affinity and (C) neutralizing activity of purified tetra-specific IgG1 to TcdA. (D) The affinity and (E) neutralizing activity of purified tetra-specific IgG1 to TcdB.

The levels of transient expression of FZ003 in ExpiCHO-S™ and Expi293™ cells were 2-3 folds more than that of its wild-type counterpart (ABAB-IgG; produced using the non-humanized alpaca E3, 5D, AA6 and AH3 V$_H$H peptides) and near 2-fold more than FZ001 (FIG. 4A). The expression level was measured with quantitative ELISA using plates coated with goat anti-human kappa light chain antibody, detected with goat anti-human IgG γ chain antibody, and with purified tetra-specific IgG1 as the standards. The FZ003 has a higher expression level than FZ001 and ABAB-IgG.

Importantly, FZ003 showed similar toxin-binding activities and neutralized both TcdA and TcdB comparably as ABAB-IgG (FIG. 4B-4E) in a cell-culture-based neutralizing assay. The affinity was measured with ELISA using plates coated with *C. difficile* toxins. The neutralizing activity was measured by applying various concentrations of tetra-specific IgG1 mixed with TcdA or TcdB to a single layer of Vero cells, and observing toxin-induced cell (Li et al. 2015; Yang et al. 2014).

FZ003 also showed neutralizing activity against TcdA and TcdB produced by *Clostridium difficile* clinical isolates. A panel of strains was kindly provided by Dr. Trevor Lawley and represented an assortment of genetically and geographically diverse clinical isolates. FZ003 (1 ug/ml) was mixed with supernatants (20× dilution) from these *C. difficile* cultures (7 days) before applying to Vero cell monolayers in 96 well-plates for 24 hr. Control wells were added supernatants with irrelevant IgG1. Cell rounding was monitored and the results shown in Table 3 demonstrate the neutralizing activity of FZ003.

TABLE 3

| Strain | Ribotype | REA Type | PFGE Type | Toxins | Place/Date of isolation | FZ003 Neutralization |
|---|---|---|---|---|---|---|
| R20291 | 27 | BI | NAP1 | TcdA/TcdB | London/2006 | YES |
| CD196 | 27 | BI | NAP1 | TcdA/TcdB | France/1985 | YES |
| 630 | 12 | R | | TcdA/TcdB | Zurich/1982 | YES |
| M120 | 78 | BK | NAP7, 8, 9 | TcdA/TcdB | UK/2007 | YES |
| BI-9 | 1 | J | NAP2 | TcdA/TcdB | Gerding Collection | YES |
| Liv024 | 1 | J | NAP2 | TcdA/TcdB | Liverpool/2009 | YES |
| Liv022 | 106 | DH | NAP11 | TcdA/TcdB | Liverpool/2009 | YES |
| TL178 | 2 | G | NAP6 | TcdA/TcdB | Belfast/2009 | YES |
| TL176 | 14 | Y | NAP4 | TcdA/TcdB | Cambridge, UK/2009 | YES |
| TL174 | 15 | | | TcdA/TcdB | Cambridge, UK/2009 | YES |
| CD305 | 23 | | | TcdA/TcdB | London/2008 | YES |
| CF5 | 17 | | | TcdB | Belgium/1995/human | YES |
| M68 | 17 | | | TcdB | Dublin/2006/human | YES |

In a similar experiment, FZ003 showed neutralizing activity against TcdA and TcdB produced by *Clostridium difficile* clinical isolates from the Emerging Infections Program—*Clostridium difficile* Surveillance Project (see the website having an URL ending in cdc.gov/hai/eip/*clostridium-difficile*.html) at the U.S. Centers for Disease Control and Prevention. Isolates were selected to represent the diversity of strain types and geographical locations circulating in the U.S. during 2010-2011. The following *Clostridium difficile* isolates were obtained through BEI Resources, NIAID, NIH. As above, FZ003 (1 ug/ml) was mixed with supernatants (20× dilution) from the *C. difficile* cultures (7 days) before applying to Vero cell monolayers in 96 well-plates for 24 hr. Control wells were added supernatants with irrelevant IgG1. Cell rounding was monitored and the results shown in Table 4 demonstrate the neutralizing activity of FZ003.

TABLE 4

| BEI Number | Designation | Ribotype | PFGE Type | Toxins | Place/Date of isolation | FZ003 neutralization |
|---|---|---|---|---|---|---|
| NR-49277 | 20100502 | 19 | NAP1 | TcdA/TcdB | Colorado/2010 | YES |
| NR-49278 | 20100207 | 27 | NAP1 | TcdA/TcdB | New York/2010 | YES |
| NR-49279 | 20100211 | 27 | NAP1 | TcdA/TcdB | New York/2010 | YES |
| NR-49280 | 20100221 | 27 | NAP1 | TcdA/TcdB | New York/2010 | YES |
| NR-49281 | 20110052 | 27 | NAP1 | TcdA/TcdB | Northeastern USA/2010 | YES |
| NR-49282 | 20120016 | 19 | NAP1 | TcdA/TcdB | New York/2010 | YES |
| NR-49283 | 20120013 | 27 | NAP1 | TcdA/TcdB | Northeastern USA/2011 | YES |
| NR-49284 | 20120015 | 27 | NAP1 | TcdA/TcdB | New York/2011 | YES |
| NR-49285 | 20110979 | 27 | NAP1 | TcdA/TcdB | Midwestern USA/2011 | YES |
| NR-49286 | 20110999 | 27 | NAP1 | TcdA/TcdB | Western-Midwestern USA/2011 | YES |
| NR-49287 | 20110868 | 27 | NAP1 | TcdA/TcdB | Southern USA/2011 | YES |
| NR-49288 | 20110870 | 27 | NAP1 | TcdA/TcdB | Tennessee/2011 | YES |
| NR-49289 | 20120184 | 27 | NAP1 | TcdA/TcdB | Tennessee/2011 | YES |
| NR-49290 | 20120187 | 19 | NAP1 | TcdA/TcdB | Tennessee/2011 | YES |
| NR-49291 | 20120236 | 27 | NAP1 | TcdA/TcdB | Midwestern USA/2011 | YES |
| NR-49292 | 20110869 | 001_072 | NAP2 | TcdA/TcdB | Tennessee/2011 | YES |
| NR-49293 | 20110978 | 001_072 | NAP2 | TcdA/TcdB | Minnesota/2011 | YES |
| NR-49294 | 20100584 | 14 | NAP4 | TcdA/TcdB | Western USA/2010 | YES |
| NR-49295 | 20111144 | 14 | NAP4 | TcdA/TcdB | New York/2011 | YES |
| NR-49296 | 20120196 | 14 | NAP4 | TcdA/TcdB | Connecticut/2011 | YES |
| NR-49297 | 20120613 | 14 | NAP4 | TcdA/TcdB | Southern USA/2011 | YES |
| NR-49298 | 20100432 | 20 | NAP4 | TcdA/TcdB | Midwestern USA/2010 | YES |
| NR-49299 | 20110241 | 20 | NAP4 | TcdA/TcdB | Midwestern USA/2010 | YES |
| NR-49300 | 20110566 | 20 | NAP4 | TcdA/TcdB | Northeastern USA/2010 | YES |
| NR-49301 | 20110818 | 20 | NAP4 | TcdA/TcdB | Western USA/2010 | YES |
| NR-49302 | 20111075 | 20 | NAP4 | TcdA/TcdB | Minnesota/2010 | YES |
| NR-49303 | 20120041 | 20 | NAP4 | TcdA/TcdB | New York/2011 | YES |
| NR-49304 | 20120956 | 20 | NAP4 | TcdA/TcdB | Southern USA/2011 | YES |
| NR-49305 | 20110742 | 2 | NAP6 | TcdA/TcdB | Northeastern USA/2011 | YES |
| NR-49306 | 20110997 | 2 | NAP6 | TcdA/TcdB | Midwestern USA/2011 | YES |
| NR-49307 | 20120020 | 2 | NAP6 | TcdA/TcdB | Northeastern USA/2011 | YES |
| NR-49308 | 20120166 | 2 | NAP6 | TcdA/TcdB | Tennessee/2011 | YES |
| NR-49309 | 20120190 | 2 | NAP6 | TcdA/TcdB | Connecticut/2011 | YES |
| NR-49310 | 20110986 | 78 | NAP7 | TcdA/TcdB | Midwestern USA/2011 | YES |
| NR-49311 | 20120183 | 78 | NAP7 | TcdA/TcdB | Southern USA/2011 | YES |
| NR-49312 | 20110960 | 17 | NAP9 | TcdA/TcdB | Minnesota/2011 | YES |
| NR-49313 | 20110963 | 17 | NAP9 | TcdA/TcdB | Minnesota/2011 | YES |
| NR-49314 | 20121412 | 47 | NAP9 | TcdA/TcdB | Georgia/2011 | YES |
| NR-49315 | 20111003 | 3 | NAP10 | TcdA/TcdB | Minnesota/2011 | YES |
| NR-49316 | 20110961 | A12 | NAP10 | TcdA/TcdB | Midwestern USA/2011 | YES |
| NR-49317 | 20111163 | 24 | NAP11 | TcdA/TcdB | Northeastern USA/2011 | YES |
| NR-49318 | 20110973 | 106 | NAP11 | TcdA/TcdB | Midwestern USA/2011 | YES |
| NR-49319 | 20110992 | 106 | NAP11 | TcdA/TcdB | Midwestern USA/2011 | YES |
| NR-49320 | 20110995 | 106 | NAP11 | TcdA/TcdB | Midwestern USA/2011 | YES |

TABLE 4-continued

| BEI Number | Designation | Ribotype | PFGE Type | Toxins | Place/Date of isolation | FZ003 neutralization |
|---|---|---|---|---|---|---|
| NR-49321 | 20120085 | 106 | NAP11 | TcdA/TcdB | Midwestern USA/2011 | YES |
| NR-49323 | 20110740 | 18 | NAP12 | TcdA/TcdB | Northeastern USA/2011 | YES |
| NR-49324 | 20121190 | 126 | NAP12 | TcdA/TcdB | Midwestern USA/2011 | YES |
| NR-49325 | 20100422 | 54 | unnamed Type A | TcdA/TcdB | Minnesota/2010 | YES |
| NR-49326 | 20111006 | 54 | unnamed Type A | TcdA/TcdB | Minnesota/2011 | YES |
| NR-49327 | 20120014 | 54 | unnamed Type A | TcdA/TcdB | New York/2011 | YES |

In Vivo Mouse Studies

Figure 5:
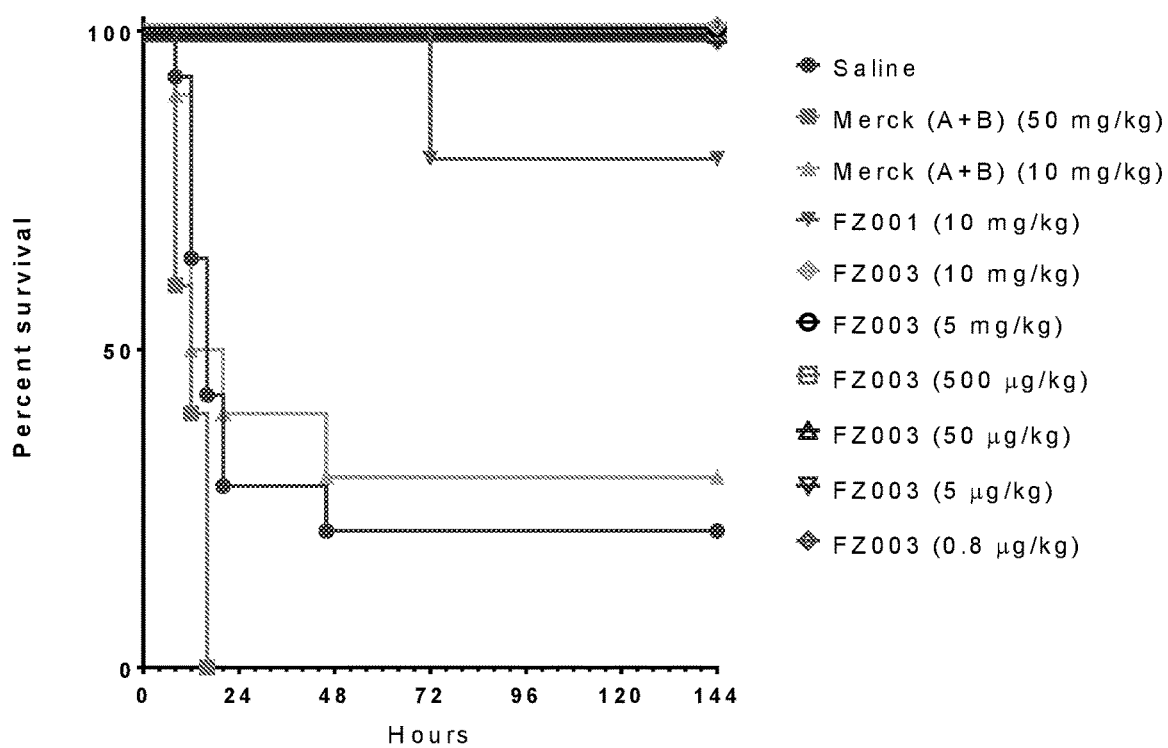
FIG. 5 provides data showing FZ003 having therapeutic efficacy against CDI in mice versus Merck anti-TcdB antibody.

In a first experiment, the neutralizing activity of FZ003 was evaluated against TcdA and TcdB in a mouse systemic toxin challenge model. *C. difficile* toxins TcdA and TcdB were pre-incubated with various concentrations of antibodies at 37° C. for 30 min before i.p. injecting to normal mice (n=5). The final dosage of each toxin for all groups was 1.2 ug/kg (body weight). The final dosages of antibodies for the groups were: FZ001 at 10 mg/kg; FZ003 at 10 mg/kg, 5 mg/kg, 500 ug/kg, 50 ug/kg, 5 ug/kg and 0.8 ug/kg. The equal volume of saline was injected as control. Mice were monitored at least three times a day for 6 days. Percent survival is shown in FIG. 5. FZ003 was ultra-potent in neutralizing both TcdA and TcdB in vivo and more than 1000× more potent than the Merck antibody. P-values are in comparison to Merck 10 mg/kg. **: P≤0.0001; *: P≤0.001.

Figure 6A:
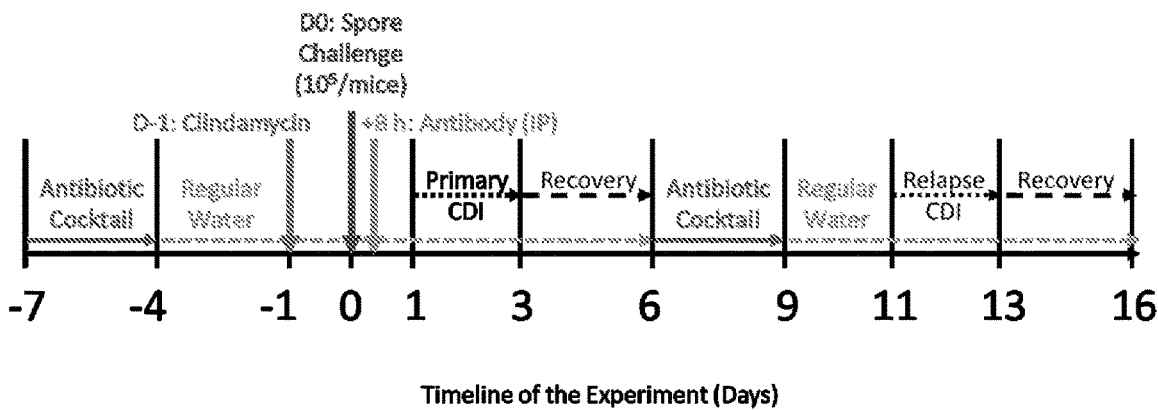
FIG. 6A shows the scheme for a mouse CDI study, comparing FZ003 versus Merck anti-TcdB antibody.

In a second experiment, FZ003 was shown to protect mice from both primary and recurrent CDI. *C. difficile* infection (CDI) was established routinely (see FIG. 6A). Briefly, mice were fed with antibiotic cocktail for 3 consecutive days (day −7 to −4) and then regular water. On day 3 after halt of antibiotic cocktail (day −1), the mice were i.p. injected with a single dose of 10 mg/kg clindamycin. The next day (day 0), each mouse was challenged with $10^5$ *C. difficile* UK1 spores orally. The antibodies at different doses were i.p. injected 8 hours post-infection. The same volume of saline was injected as placebo. The primary disease was monitored for 6 days (day 1-6). Theoretically, without treatment, the disease peak will appear during day 1-3. During day 4-6, the mice will recover from illness. After a full recovery, the mice were caged in clean cages and fed with another round of antibiotic cocktail water for 3 consecutive days (day 6-9) to induce sequent recurrence. Usually, the recurrent disease will occur on day 11-13 without treatment. The mice were monitored for diarrhea, weight loss and survival through the experiment.

Figure 6B:
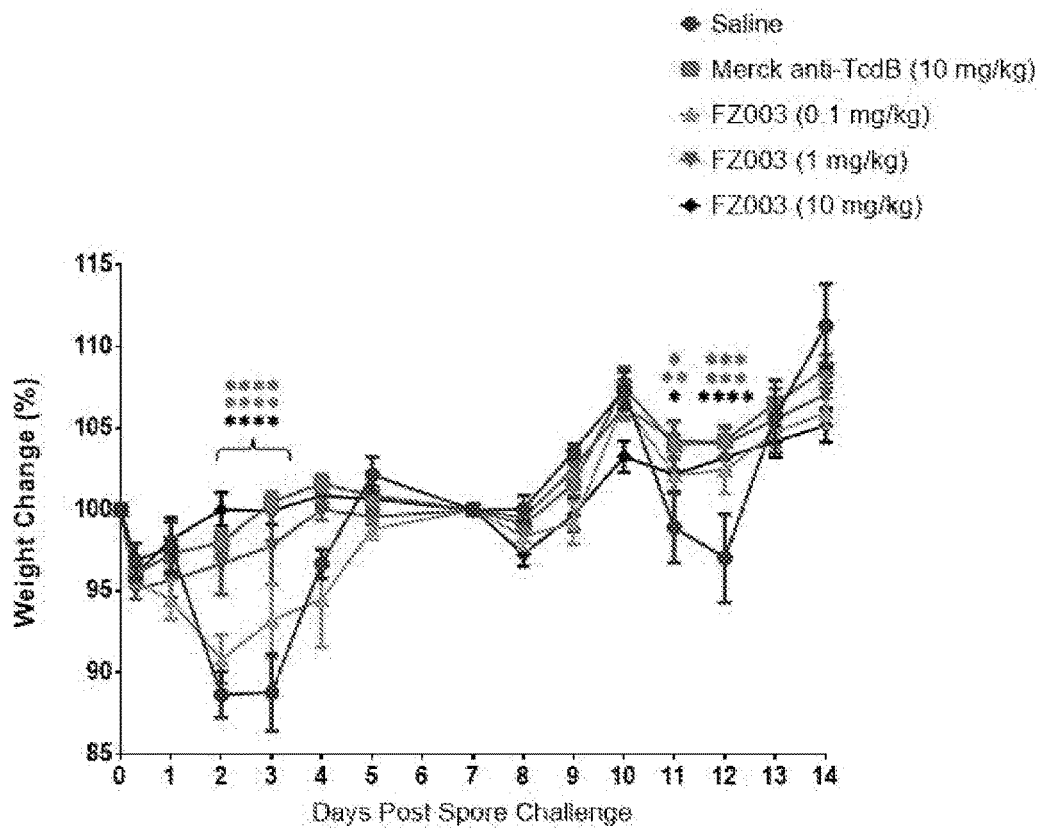
FIG. 6B shows weight of mice treated with FZ003 versus Merck anti-TcdB antibody.
Figure 6C:
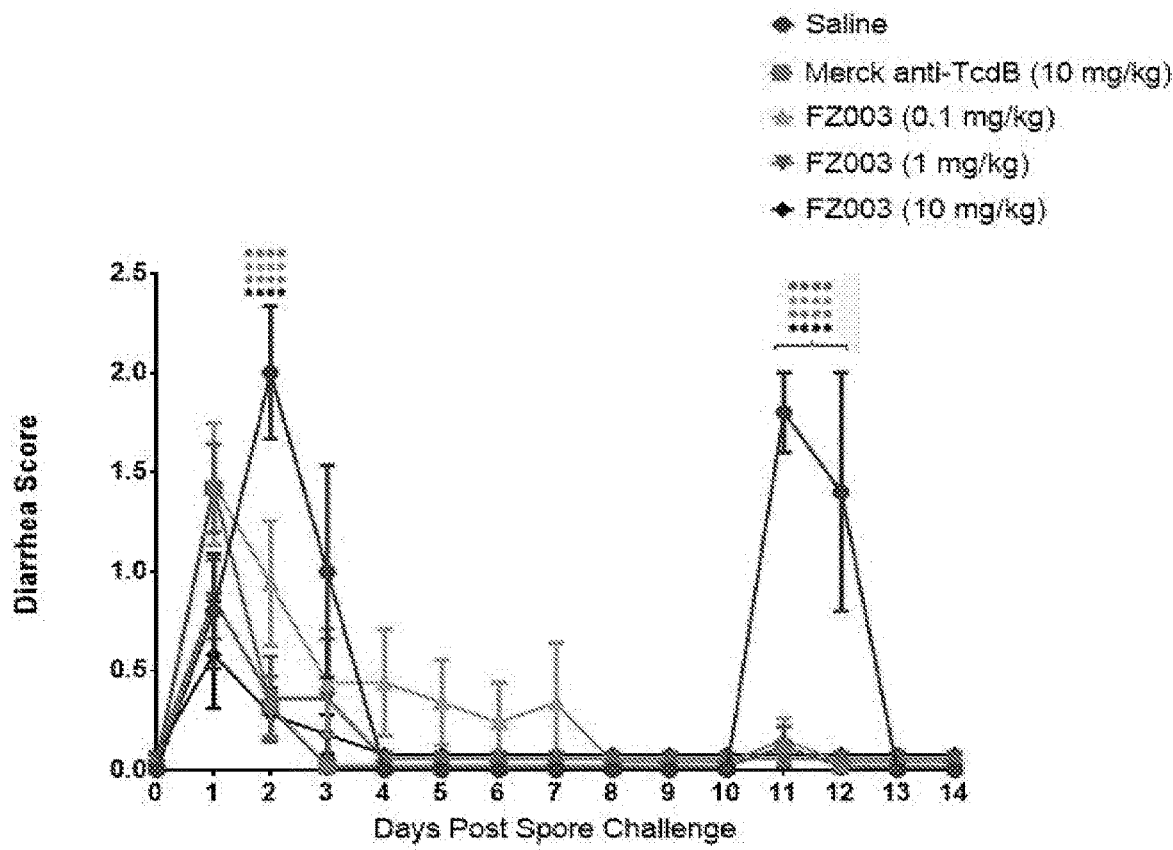
FIG. 6C shows diarrhea scores for mice treated with FZ003 versus Merck anti-TcdB antibody.
Figure 6D:
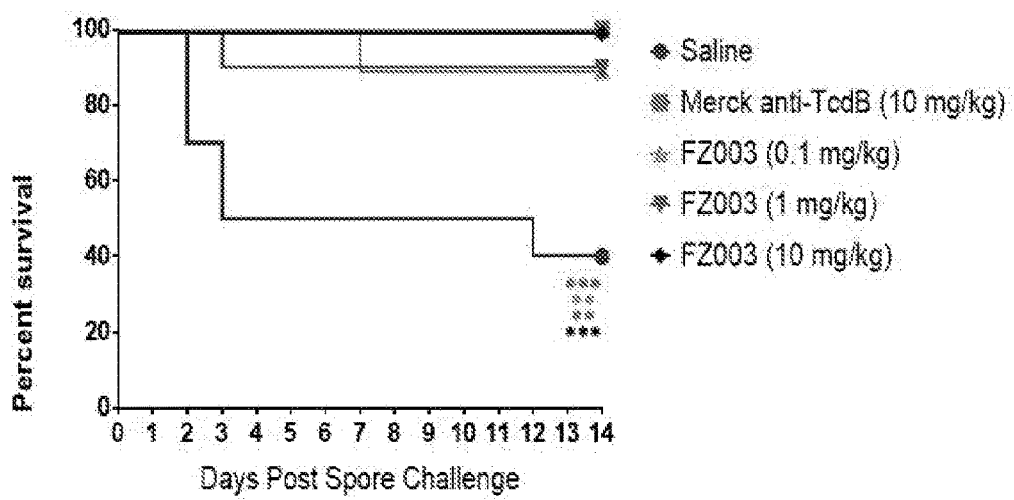
FIG. 6D shows percent survival of mice treated with FZ003 versus Merck anti-TcdB antibody.

FZ003 (0.1 mg/kg, 1 mg/kg, 10 mg/kg) and Merck anti-TcdB antibody (10 mg/kg) were intraperitoneally injected 8 h post *C. difficile* challenge. Mice were monitored for disease symptoms as indicated by diarrhea score, weight loss and survival (FIGS. 6B, 6C, 6D). Compared to the Merck anti-TcdB monoclonal antibody that was approved by the FDA (10 mg/Kg), FZ003 provided similar protection at a dose as low as 0.1 mg/Kg. The weight loss, diarrhea score and survival were monitored through the experiment (n=10). FIG. 6B—weight loss. The bodyweights on day 0 before infection were used as baseline. The weight loss was monitored until day 14. FIG. 6C—diarrhea was monitored according to a previous published score system (Yang et al. 2014; Li et al. 2015; Yang et al. 2016). FIG. 6D—survival. P values compared to saline. **≤0.0001, *≤0.001, **≤0.01, *≤0.05. For saline group, the disease peak of primary infection was on day 2 and 3 and that of sequent recurrence was on day 11 and 12 based on the weight loss and diarrhea score. 40% of saline group eventually survived from primary and sequent infection. The treatment groups with certain doses of FZ003 showed comparable protective effects to 10 mg/kg Merck antibody. With the treatment of 10 mg/kg Merck antibody, mice showed no significant weight loss through the primary infection and had statistically lower diarrhea score compared with saline group. All mice inject with Merck antibody survived at the end of the experiment. FZ003 at the doses of 10 mg/kg fully protected the mice from weight loss and death. As shown in FIG. 6C, FZ003 at 10 mg/kg was the best to protect the host from diarrhea during the primary infection. FZ003 showed a dose dependent protective effect. By contrast, FZ003 at 0.1 mg/kg showed slightly reduced protection from weight loss and diarrhea compared with the higher doses. 80% mice survived with 1 mg/kg and 0.1 mg/kg of FZ003 treatment.

Figure 7A:
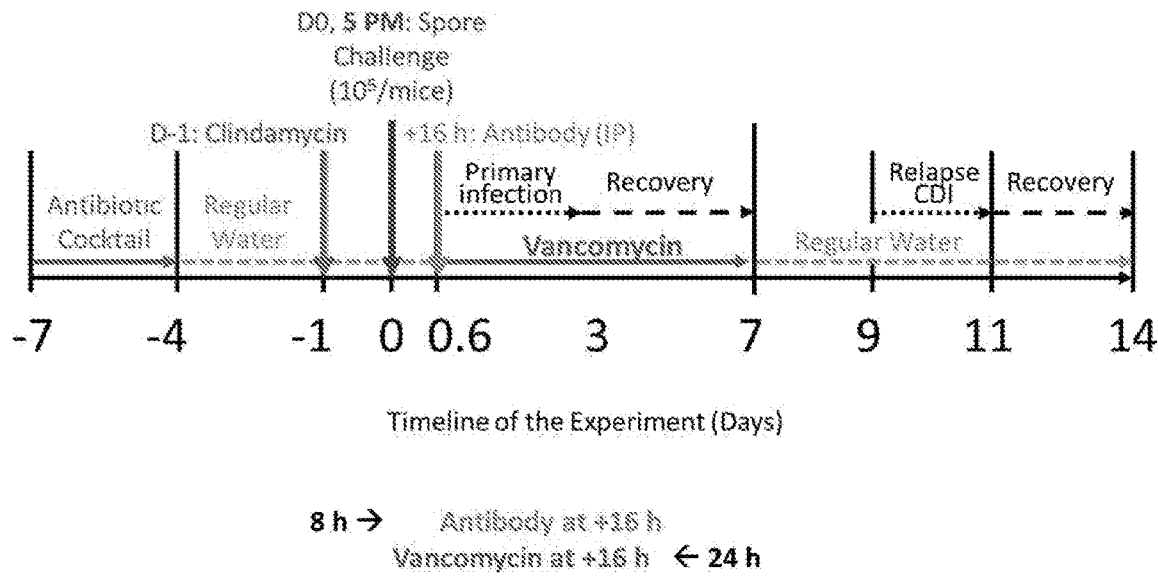
FIG. 7A shows the scheme for a study of vancomycin-induced relapse CDI in mice, comparing FZ003 versus Merck anti-TcdB antibody.

In a third experiment, the effectiveness of FZ003 versus Merck anti-TcdB antibody in vancomycin-induced relapse CDI was studied. *C. difficile* infection (CDI) was established routinely. Briefly, mice were fed with antibiotic cocktail for 3 consecutive days (day −7 to −4) and then regular water (see FIG. 7A). On day 3 after halt of antibiotic cocktail (day −1), the mice were i.p. injected with a single dose of 10 mg/kg clindamycin. The next day (day 0), each mouse was challenged with $10^5$ *C. difficile* UK1 spores orally. Single dosage of FZ003 at different doses were i.p. injected 16 hours post-infection. The same volume of saline was injected as placebo. At the same time as antibody injection, all groups received daily single dose of vancomycin treatment for 6 consecutive days (day 1-7) to block the primary disease. The peak disease of vancomycin induced relapse often occurs from day 9 to 11.

Figure 7B:
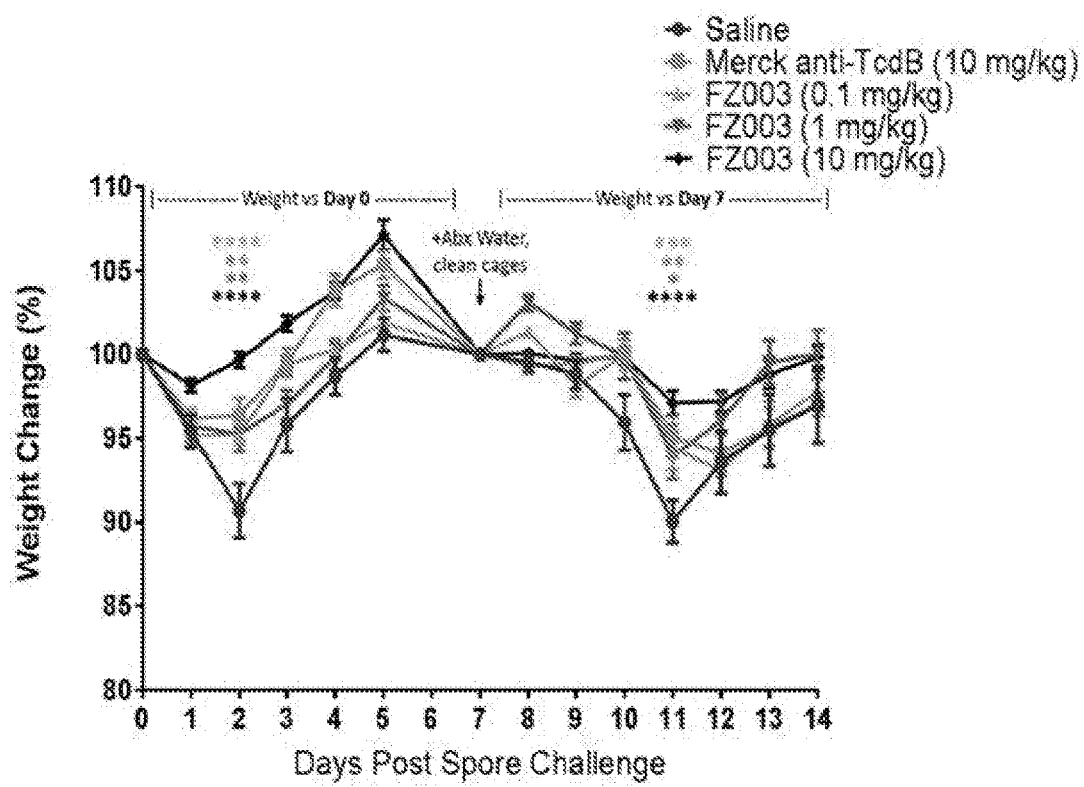
FIG. 7B shows weight of mice treated with FZ003 versus Merck anti-TcdB antibody.
Figure 7C:
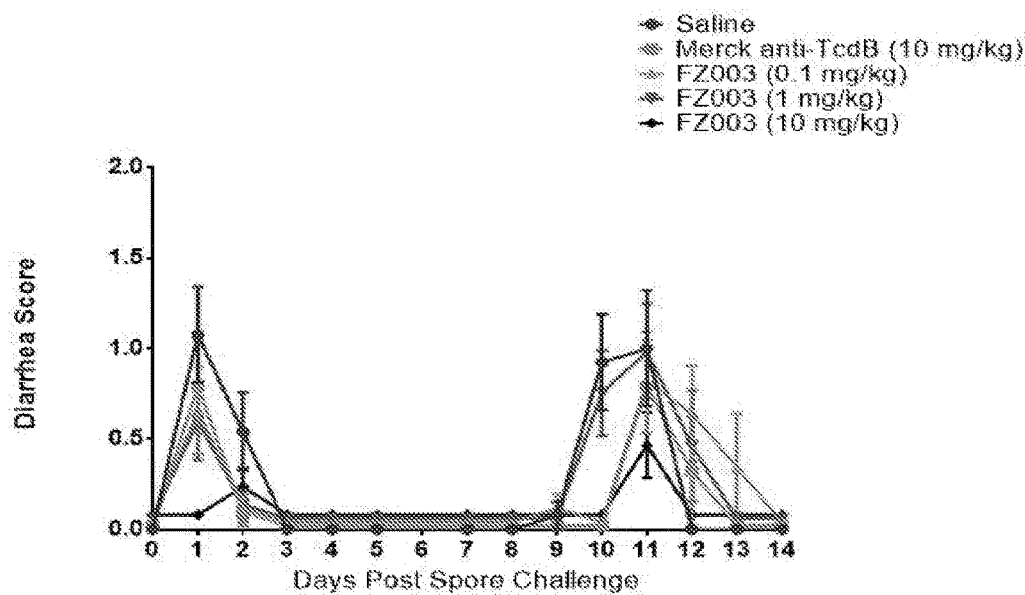
FIG. 7C shows diarrhea scores for mice treated with FZ003 versus Merck anti-TcdB antibody.
Figure 7D:
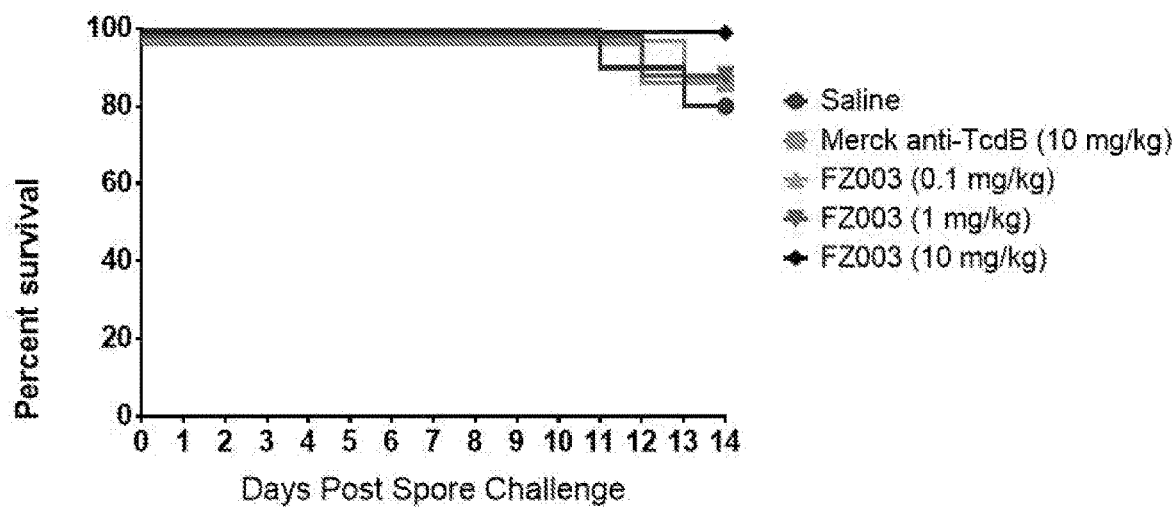
FIG. 7D shows percent survival of mice treated with FZ003 versus Merck anti-TcdB antibody.

The weight loss, diarrhea score and survival were monitored through the experiment (n=10). FIG. 7B—weight loss. The bodyweights on day 0 before infection were used as baseline. The weight loss was monitored until day 14. FIG. 7C diarrhea was monitored according to a previous published score system (Yang et al. 2014; Li et al. 2015; Yang et al. 2016). FIG. 7D—survival. P values compared to saline (**≤0.0001, *≤0.001, **≤0.01, *≤0.05).

With vancomycin treatment, none of the mice died through 7 days, although mild weight loss and diarrhea were observed on day 1 and 2 in saline group. Treatment with vancomycin plus Merck antibody at 10 mg/kg or FZ003 at 1 and 0.1 mg/kg attenuated the symptoms compared to saline group on day 1 and 2. Mice received vancomycin plus 10 mg/kg FZ003 had no significant disease through day 1 to day 7. At the recurrent stage (day 7-14), the saline group develop significant diarrhea on day 10 and 11. Accordingly, a dramatic weight loss for saline group was on day 11. All the antibody treated groups had reduced diarrhea and weight loss. Among all the antibody treated groups, FZ003 at the dose of 10 mg/kg was the best to fully protect the host from weight loss and death, although minor diarrhea was observed.

Figure 8A:
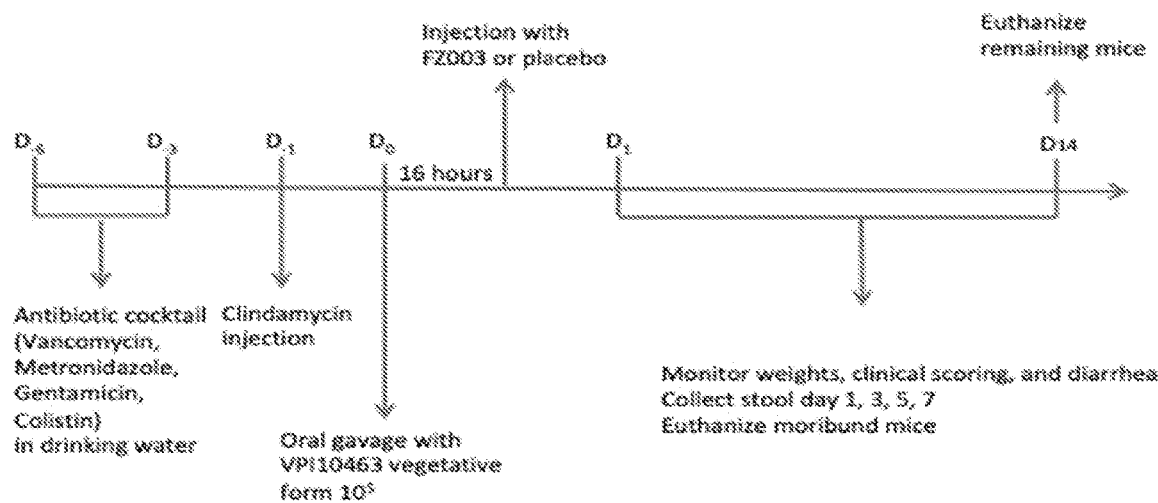
FIG. 8A shows the scheme for a study of the protective effects of FZ003 (10 mg/kg) against primary CDI in aged mouse model.

In a fourth experiment, the protective effects of FZ003 (10 mg/kg or 1 mg/kg) against primary CDI in aged mouse model (n=5) was studied. FIG. 8A shows a timeline of treatment in the aged mouse model. *C. difficile* infection (CDI) was established routinely. Briefly, mice were fed with antibiotic cocktail for 3 consecutive days (day −7 to −4) and then regular water. On day 3 after halt of antibiotic cocktail (day −1), the mice were i.p. injected with a single dose of 10 mg/kg clindamycin. The next day (day 0), each mouse was challenged with $10^5$ CFU of *C. difficile* VPI10463 vegetative cells. Single dosage of FZ003 at 10 mg/kg was i.p. injected 16 hours post-infection. The same volume of PBS was injected as placebo.

Figure 8B:
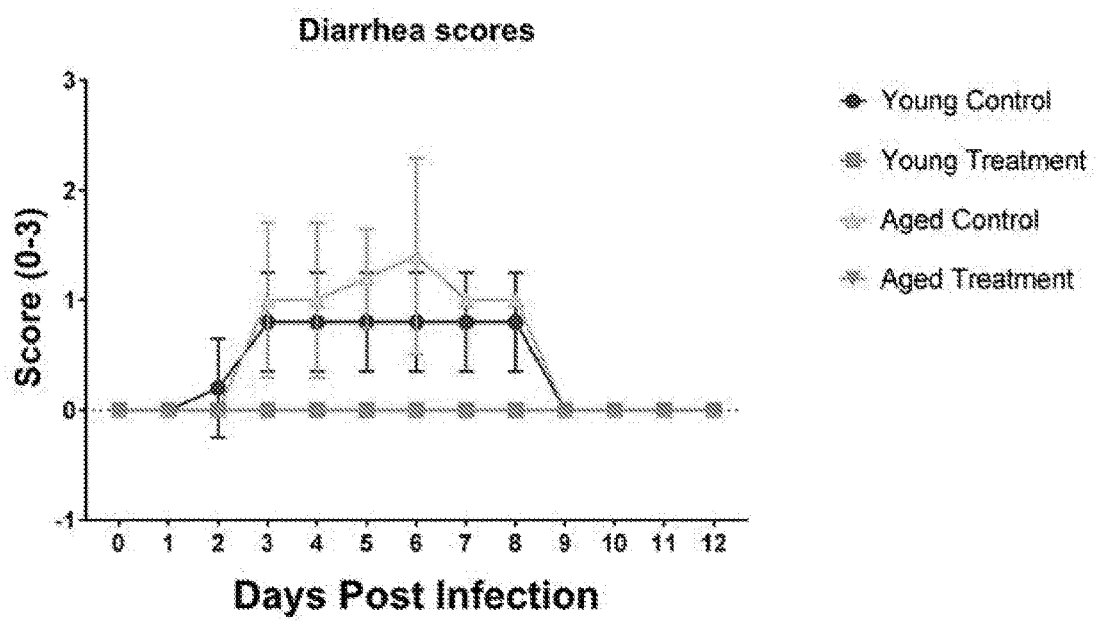
FIG. 8B shows diarrhea scores for mice treated with FZ003 (10 mg/kg) versus PBS.

FIG. 8B—diarrhea was monitored according to a previous published score system. (Yang et al. 2014; Yang et al. 2016) FIG. 8C (10 mg/kg FZ003) and FIG. 8D (1 mg/kg FZ003)—weight loss. The bodyweights on day 0 before infection were used as baseline. The weight loss was monitored until day 12. FIG. 8E (10 mg/kg FZ003) and FIG. 8F (1 mg/kg FZ003)—clinical scoring was performed by clinical symptoms such as diarrhea, weight loss and appearance and the data shows the groups of FZ003 protected aged mice from CDI. FIG. 8G (10 mg/kg FZ003) and FIG. 8H (1 mg/kg FZ003)—survival. P values compared to saline (**≤0.0001, *≤0.001, **≤0.01, *≤0.05).

Figure 8C:
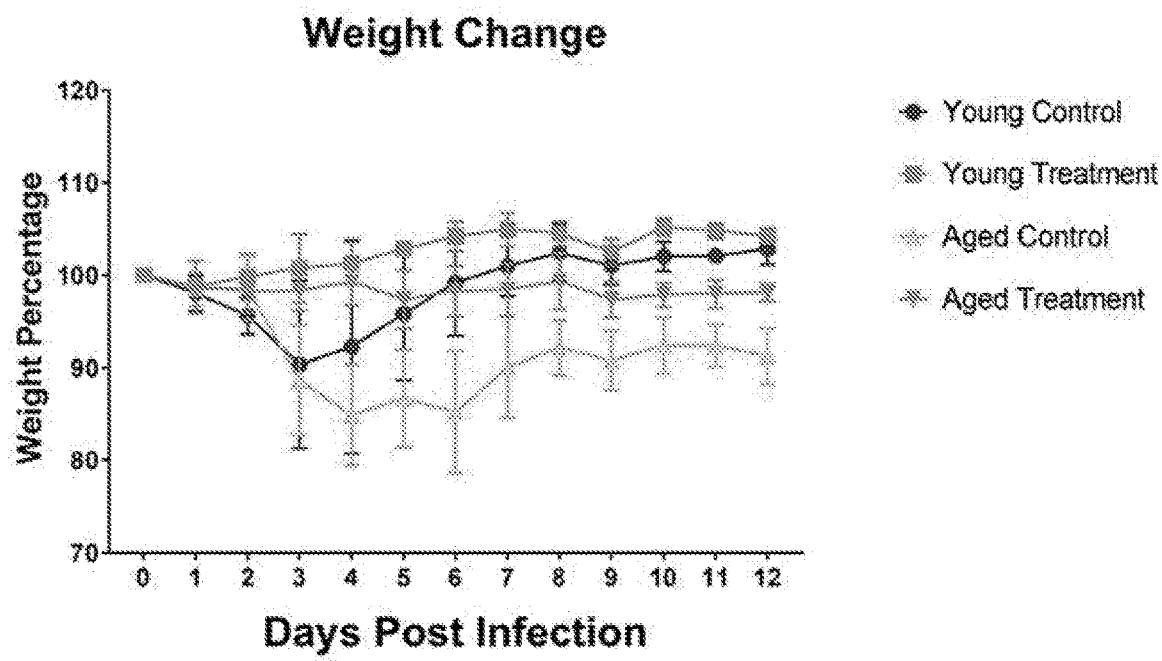
FIG. 8C shows weight of mice treated with FZ003 (10 mg/kg) versus PBS.
Figure 8D:
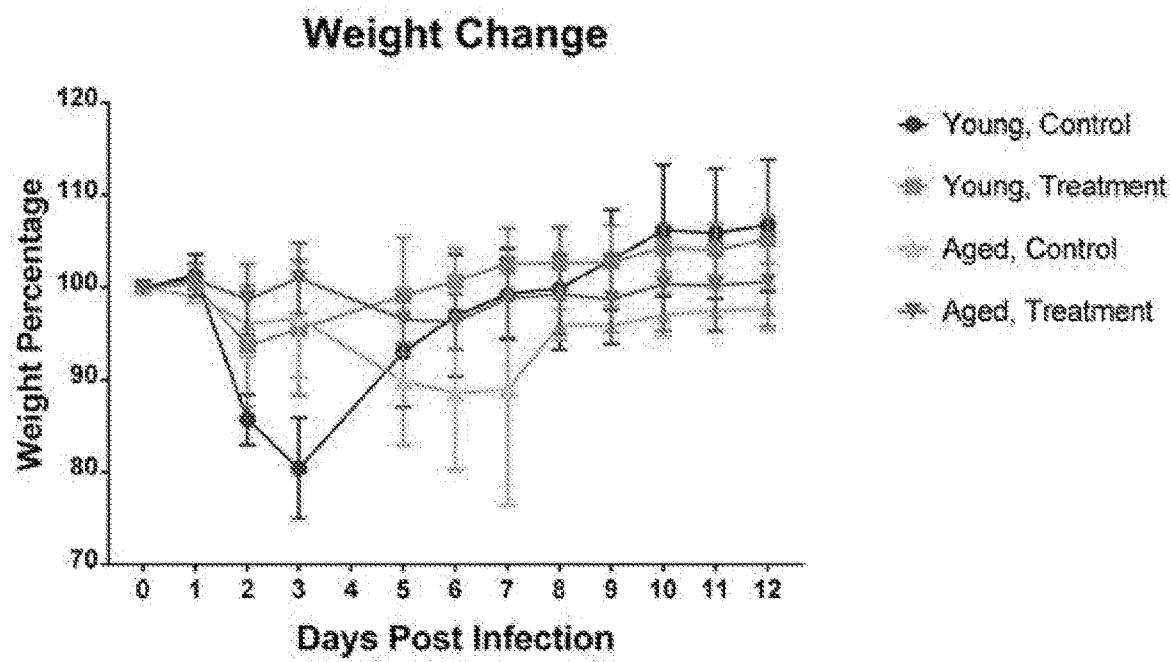
FIG. 8D shows weight of mice treated with FZ003 (1 mg/kg) versus PBS.
Figure 8E:
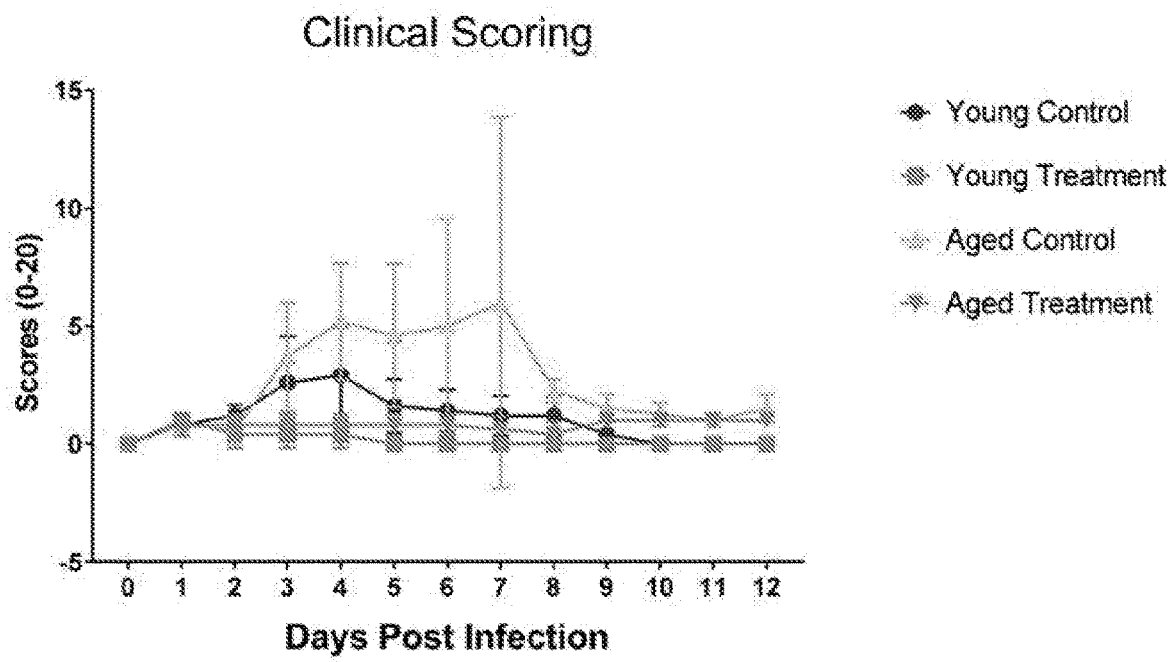
FIG. 8E shows clinical scoring of mice treated with FZ003 (10 mg/kg) versus PBS.
Figure 8F:
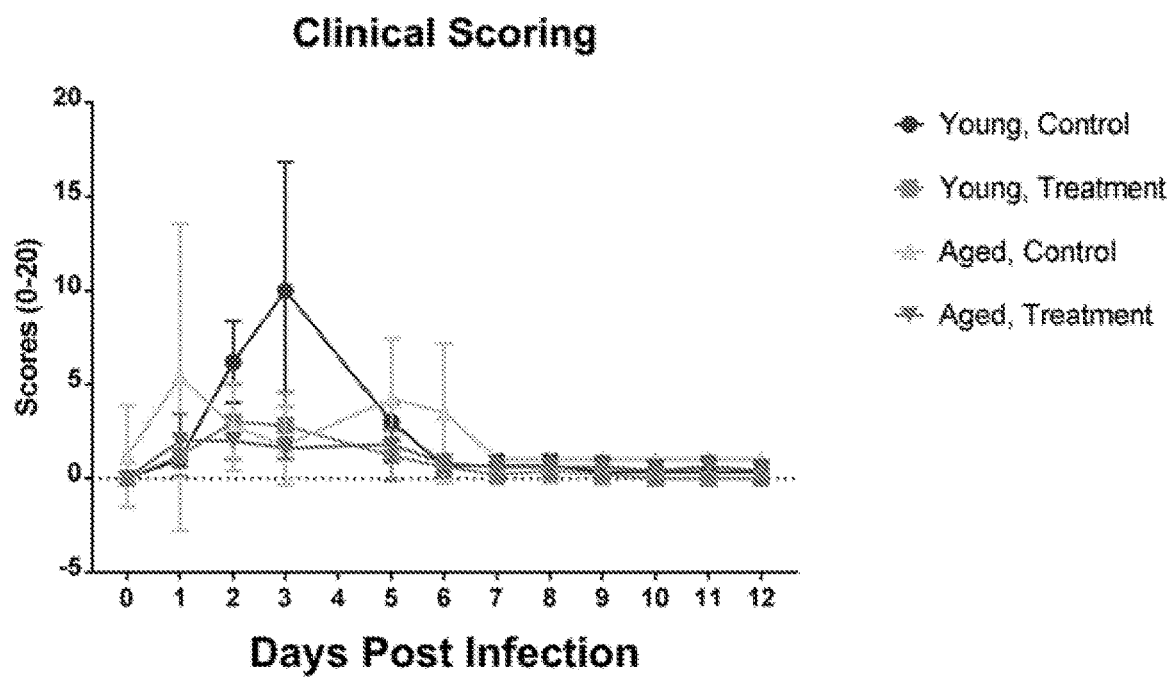
FIG. 8F shows clinical scoring of mice treated with FZ003 (1 mg/kg) versus PBS.
Figure 8G:
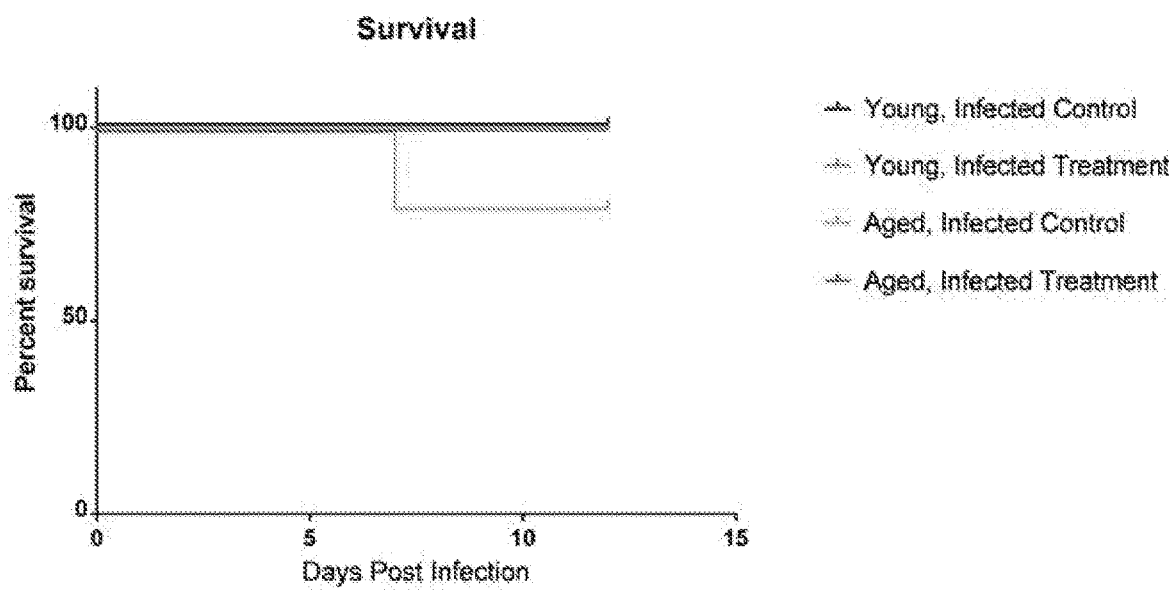
FIG. 8G shows percent survival of mice treated with FZ003 (10 mg/kg) versus PBS.
Figure 8H:
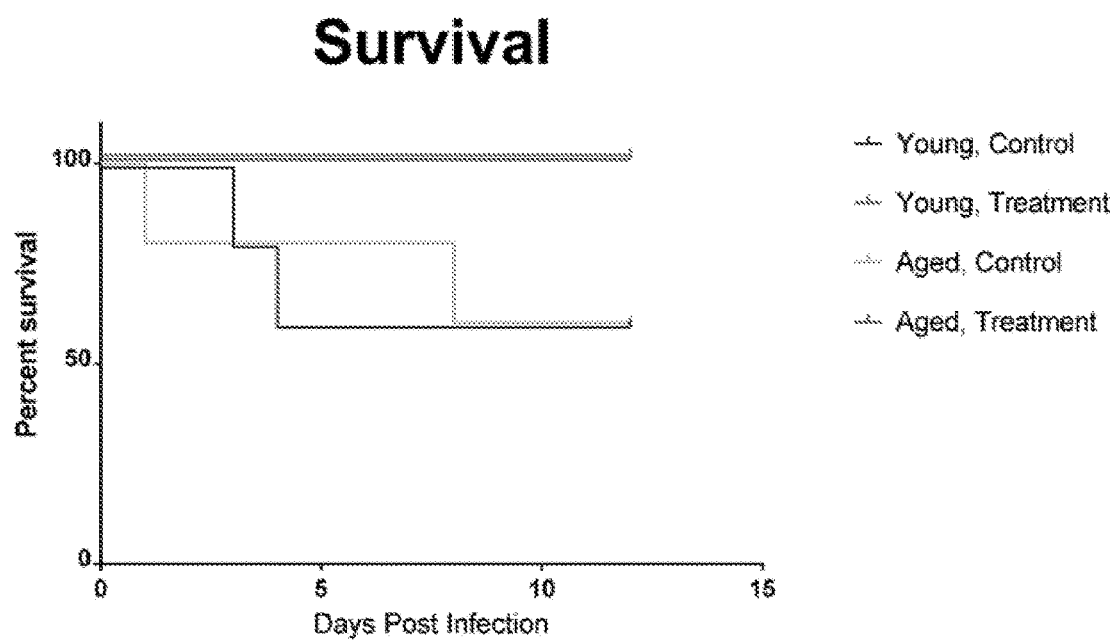
FIG. 8H shows percent survival of mice treated with FZ003 (1 mg/kg) versus PBS.

The aged mice started to lose weight on day 3 and gain weight on day 7 as in FIGS. 8C and 8D. With the treatment of FZ003, the mice did not have significant weight loss throughout the experiment. The FZ003 treatment also improved the clinical symptom. In treated group, none of the mice developed diarrhea. By contrast, mice from PBS control group developed mild to moderate diarrhea. Compared with young mice, aged mice developed a longer disease period that assembled chronic CDI in humans.

Figure 9A:
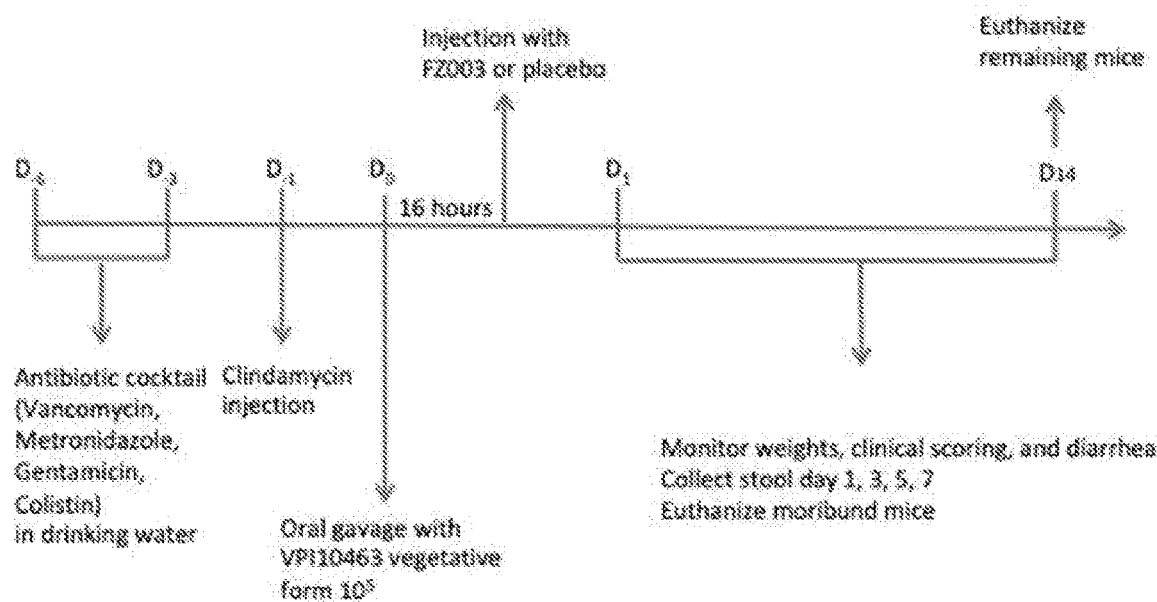
FIG. 9A shows the scheme for a study of the protective effects of FZ003 (1 mg/kg) against primary CDI in aged mouse model.
Figure 9B:
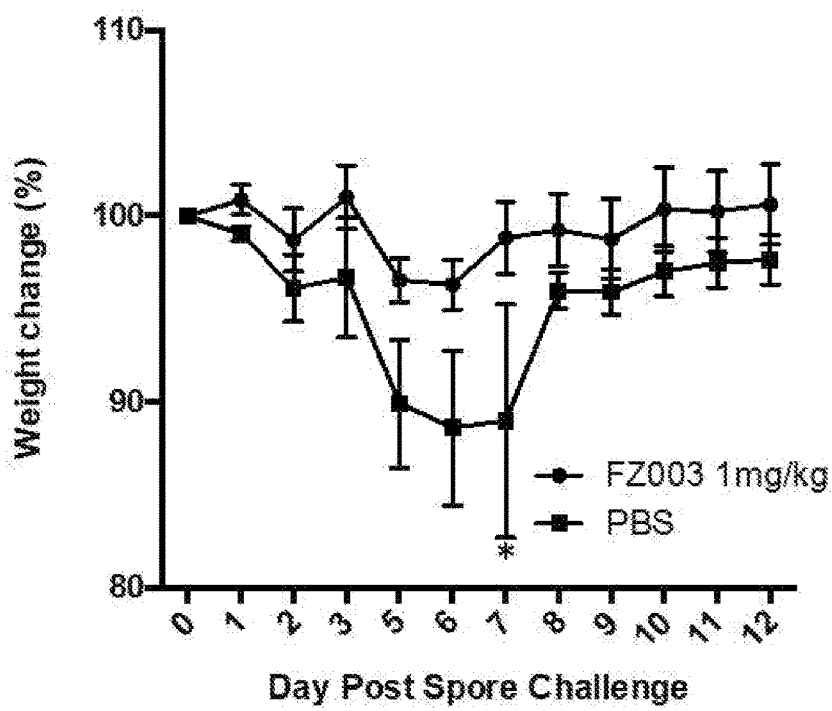
FIG. 9B shows weight of mice treated with FZ003 versus PBS.
Figure 9C:
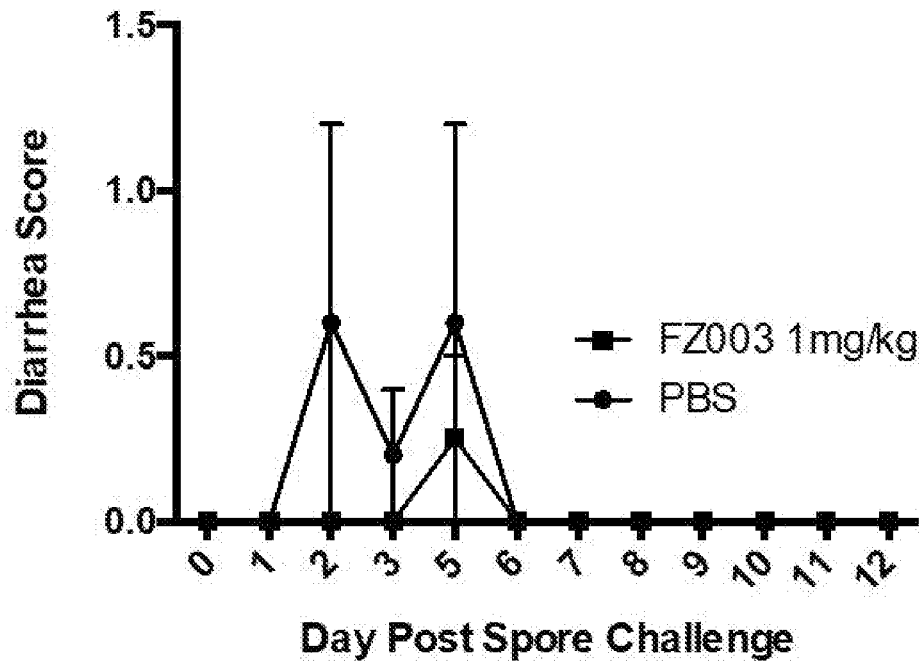
FIG. 9C shows diarrhea scores for mice treated with FZ003 versus PBS.
Figure 9D:
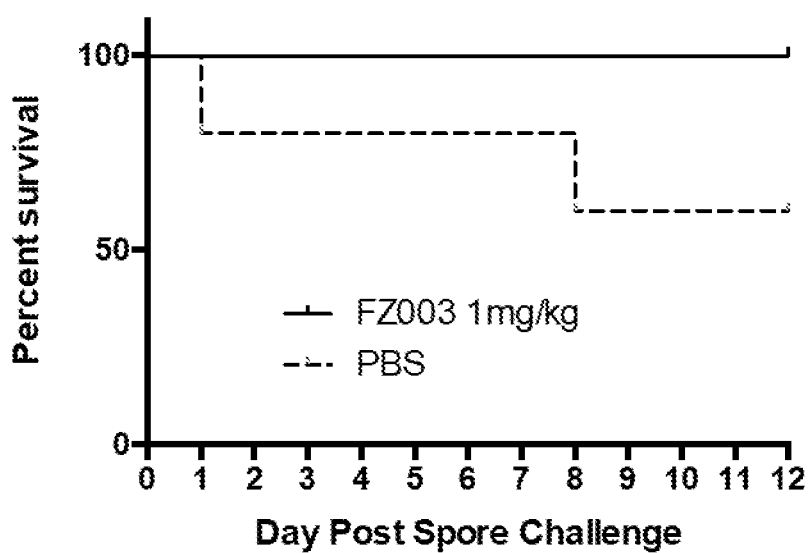
FIG. 9D shows percent survival of mice treated with FZ003 versus PBS.

The experiment was repeated using the same scheme (FIG. 9A), but the amount of FZ003 administered to the mice was reduced to (1 mg/kg). FIG. 9B—weight loss. The bodyweights on day 0 before infection were used as baseline. The weight loss was monitored until day 12. FIG. 9C—diarrhea was monitored according to a previous published score system. (Yang et al. 2014; Li et al. 2015; Yang et al. 2016) FIG. 9D—survival. P values compared to saline (*≤0.05).

In Vivo Hamster Study

Figure 10A:
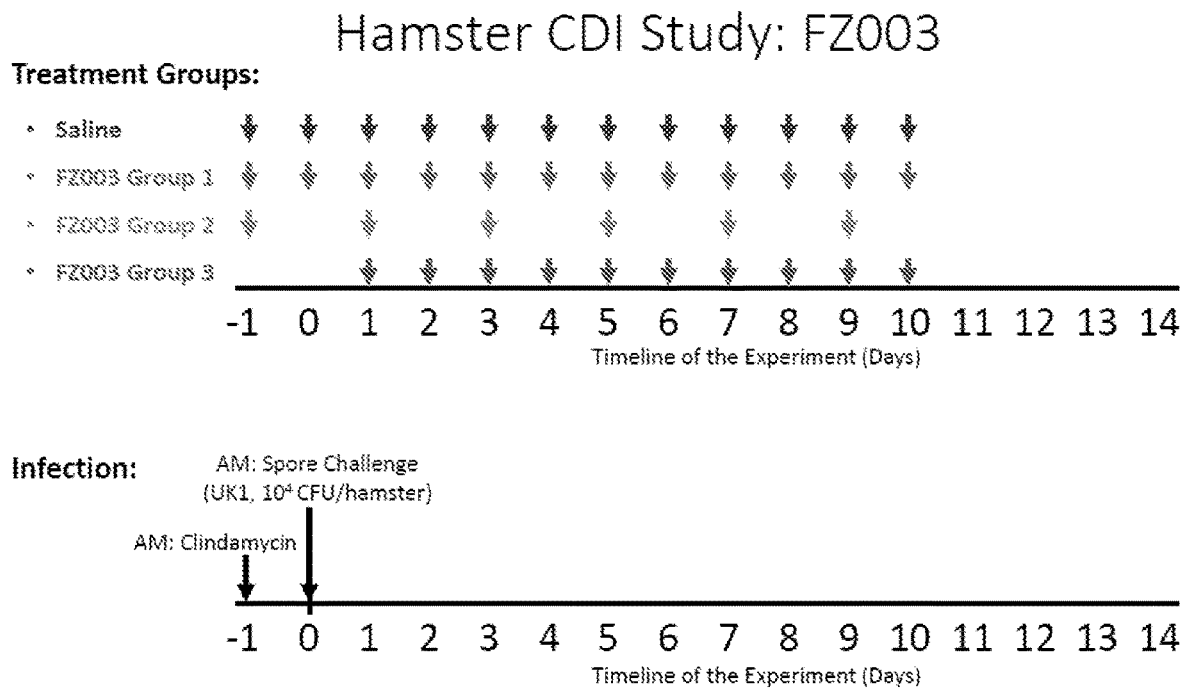
FIG. 10A shows the scheme for a hamster CDI study, comparing FZ003 versus saline.

The therapeutic efficacy of FZ003 was also evaluated against *C. difficile* infection (CDI) in a hamster disease model. To induce CDI, groups of Golden Syrian hamsters (5 per group) were injected with clindamycin (30 mg/kg; ip) one day before *C. difficile* spore challenge (UK1, $10^4$ CFU/mouse). For treatment, FZ003 was administered at 10 mg/kg, ip, as shown in FIG. 10A. Survival was monitored for up to Day +18 post challenge. Weight loss and diarrhea were monitored up to Day +14 post challenge. Cage changes were made on Day +7, +17.

Figure 10B:
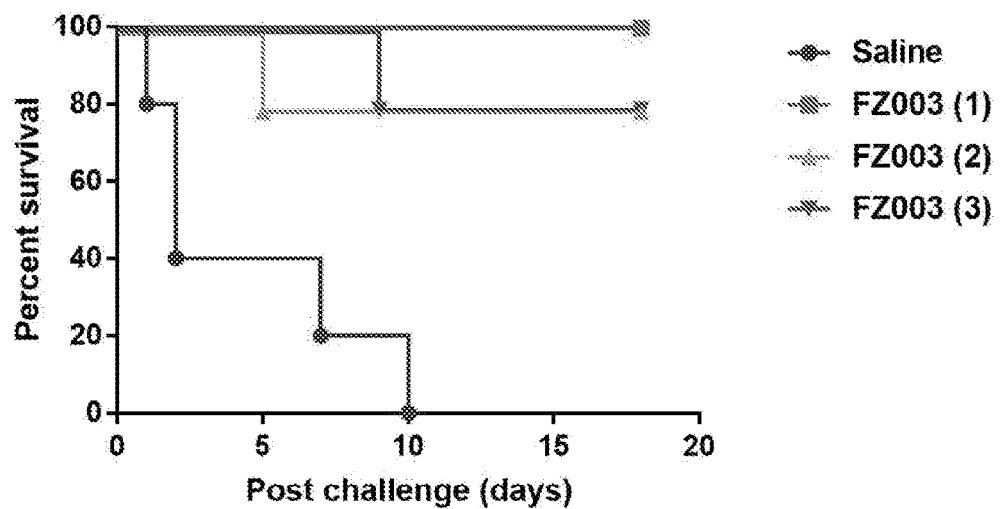
FIG. 10B shows percent survival of hamsters treated with FZ003 or saline.
Figure 10C:
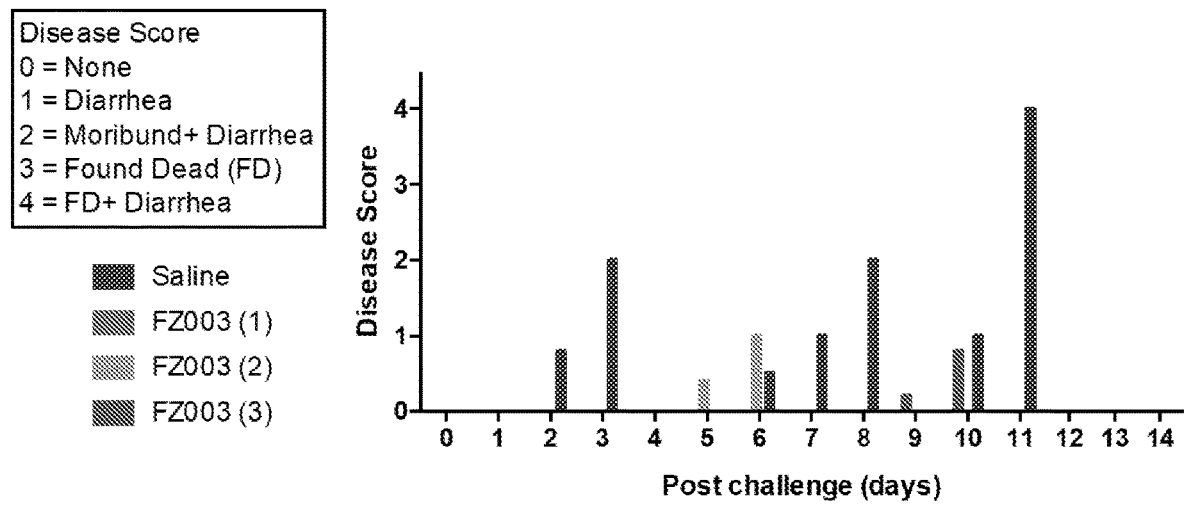
FIG. 10C shows disease scores for hamsters treated with FZ003 or saline.
Figure 10D:
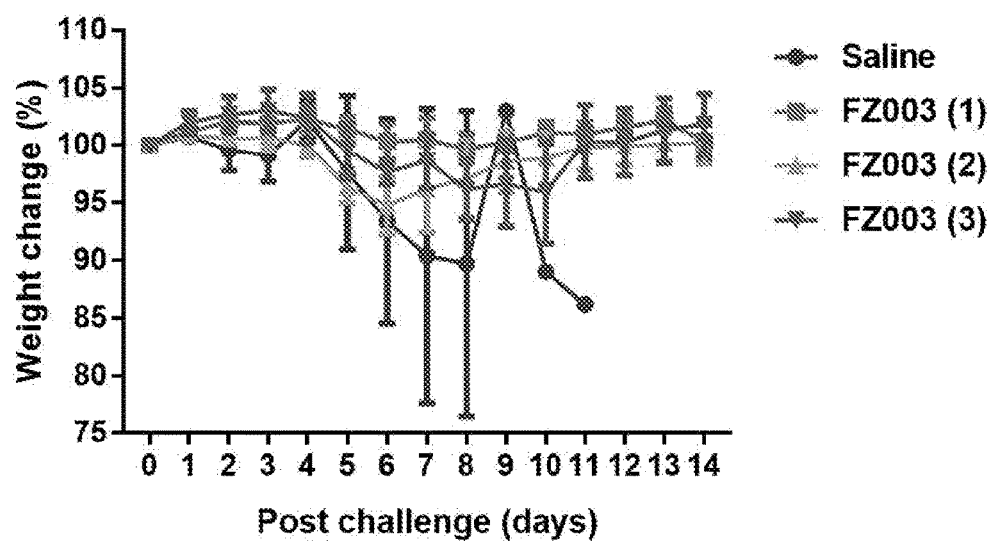
FIG. 10D shows weight of hamsters treated with FZ003 or saline.

As can be seen in FIG. 10B, animals treated with FZ003 showed a marked improvement in survival versus control animals receiving only saline, with decreased disease scores (FIG. 10C) and increased weight (FIG. 10D) as well. Hamster survival was analyzed by Kaplan-Meier survival analysis with Logrank test of significance using the Prism statistic software program and p value is indicated (P=0.0018 (Group 1); P=0.0132 (Group 2); P=0.0066 (Group 3).

While the invention has been described with reference to certain particular embodiments thereof, those skilled in the art will appreciate that various modifications may be made without departing from the spirit and scope of the invention. The scope of the appended claims is not to be limited to the specific embodiments described.

Amino Acid and Nucleic Acid Sequences

SEQ ID NO:1—humanized $V_HH$ peptide monomer 5D (h5D)

SEQ ID NO:2—humanized $V_HH$ peptide monomer E3 (hE3)

SEQ ID NO:3—humanized $V_HH$ peptide monomer AA6 (hAA6)

SEQ ID NO:4—humanized $V_HH$ peptide monomer AH3 (hAH3)

SEQ ID NO:5—linker-1

SEQ ID NO:6—linker-2

SEQ ID NO:8—amino acid sequence of FZ003 light chain (hAA6-hE3)

SEQ ID NO:9—amino acid sequence FZ003 heavy chain (hAH3-h5D)

SEQ ID NO:10—nucleic acid sequence of FZ003 light chain (hAA6-hE3)

SEQ ID NO:11—nucleic acid sequence of FZ003 heavy chain (hAH3-h5D)

SEQ ID NO:12—nucleic acid sequence of expression vector encoding FZ003 light chain SEQ ID NO:13—nucleic acid sequence of expression vector encoding FZ003 heavy chain SEQ ID NO:14—amino acid sequence of CDR1 of alpaca $V_HH$ peptide 5D SEQ ID NO:15—amino acid sequence of CDR2 of alpaca $V_HH$ peptide 5D SEQ ID NO:16—amino acid sequence of CDR3 of alpaca $V_HH$ peptide 5D SEQ ID NO:17—amino acid sequence of CDR1 of alpaca $V_HH$ peptide E3

SEQ ID NO:18—amino acid sequence of CDR2 of alpaca $V_HH$ peptide E3

SEQ ID NO:19—amino acid sequence of CDR3 of alpaca $V_HH$ peptide E3

SEQ ID NO:20—amino acid sequence of CDR1 of alpaca $V_HH$ peptide AH3

SEQ ID NO:21—amino acid sequence of CDR2 of alpaca $V_HH$ peptide AH3

SEQ ID NO:22—amino acid sequence of CDR3 of alpaca $V_HH$ peptide AH3

SEQ ID NO:23—amino acid sequence of CDR1 of alpaca $V_HH$ peptide AA6

SEQ ID NO:24—amino acid sequence of CDR2 of alpaca $V_HH$ peptide AA6

SEQ ID NO:25—amino acid sequence of CDR3 of alpaca $V_HH$ peptide AA6

SEQ ID NO:26—amino acid sequence of alpaca $V_HH$ peptide 5D

SEQ ID NO:27—amino acid sequence of alpaca $V_HH$ peptide E3

SEQ ID NO:28—amino acid sequence of alpaca $V_HH$ peptide AH3

SEQ ID NO:29—amino acid sequence of alpaca $V_HH$ peptide AA6

SEQ ID NO:30—amino acid sequence of human IGHV3-23*01

SEQ ID NO:31—amino acid sequence of human IGHJ4*01

SEQ ID NO:32—MS humanized $V_HH$ peptide monomer 5D (MSh5D)

SEQ ID NO:33—MS humanized V$_H$H peptide monomer E3 (MShE3)

SEQ ID NO:34—MS humanized V$_H$H peptide monomer AA6 (MShAA6)

SEQ ID NO:35—MS humanized V$_H$H peptide monomer AH3 (MShAH3)

SEQ ID NO:36—amino acid sequence of FZ001 light chain (MShAA6-MShE3)

SEQ ID NO:37—amino acid sequence FZ001 heavy chain (MShAH3-MSh5D)

SEQ ID NO:38—nucleic acid sequence of FZ001 light chain (MShAA6-MShE3)

SEQ ID NO:39—nucleic acid sequence of FZ001 heavy chain (MShAH3-MSh5D)

REFERENCES

All patents and publications mentioned in this specification are indicative of the level of skill of those skilled in the art to which the invention pertains. Each cited patent and publication is incorporated herein by reference in its entirety. All of the following references have been cited in this application:

Carter, P., et al. (1992). Humanization of an anti-p185HER2 antibody for human cancer therapy. *Proceedings of the National Academy of Sciences of the United States of America* 89(10): 4285-4289.

Desmet, J., et al. (2010). Humanization by Resurfacing. *Antibody Engineering*. R. Kontermann and S. Dübel, Springer Berlin Heidelberg: 341-353.

Harding, F. A., et al. (2010). The immunogenicity of humanized and fully human antibodies. *mAbs* 2(3): 256-265.

Könning, D., et al. (2017). Camelid and shark single domain antibodies: structural features and therapeutic potential. *Current Opinion in Structural Biology* 45: 10-16.

Kunik, V., et al. (2012). Structural Consensus among Antibodies Defines the Antigen Binding Site. *PLoS Computational Biology* 8(2): e1002388.

Li, S., et al. (2015). Critical Roles of *Clostridium difficile* Toxin B Enzymatic Activities in Pathogenesis. *Infect Immun* 83(2): 502-513.

Olimpieri, P. P., et al. (2013). Prediction of site-specific interactions in antibody-antigen complexes: the proABC method and server. *Bioinformatics* (Oxford, England) 29(18): 2285-2291.

Roguska, M. A., et al. (1994). Humanization of murine monoclonal antibodies through variable domain resurfacing. *Proceedings of the National Academy of Sciences of the United States of America* 91(3): 969-973.

Roque-Navarro, L., et al. (2003). Humanization of Predicted T-Cell Epitopes Reduces the Immunogenicity of Chimeric Antibodies: New Evidence Supporting a Simple Method. *Hybridoma and Hybridomics* 22(4): 245-257.

Sela-Culang, I., et al. (2013). The Structural Basis of Antibody-Antigen Recognition. *Frontiers in Immunology* 4: 302, pp. 1-13.

Williams, D., et al. (2010). Humanising Antibodies by CDR Grafting. *Antibody Engineering*. R. Kontermann and S. Dübel, Springer Berlin Heidelberg: 319-339.

Yang, Z., et al. (2014). A novel multivalent, single-domain antibody targeting TcdA and TcdB prevents fulminant *Clostridium difficile* infection in mice. *J Infect Dis* 210(6): 964-972.

Yang, Z., et al. (2016). Intravenous adenovirus expressing a multi-specific, single-domain antibody neutralizing TcdA and TcdB protects mice from *Clostridium difficile* infection. *Pathog Dis* 74(7): pp. 1-8.

Zhang, Y.-F. and M. Ho (2017). Humanization of rabbit monoclonal antibodies via grafting combined Kabat/IMGT/Paratome complementarity-determining regions: rationale and examples. *mAbs* 9(3): 419-429.

What is claimed is:

1. A tetra-specific, octameric binding agent comprising, two sets of linked first and second humanized $V_HH$ peptide monomers, and two sets of linked third and fourth humanized $V_HH$ peptide monomers,
    wherein the binding agent comprises two arms, each arm comprising a heavy chain lacking a variable region and a light chain lacking a variable region, and each chain having an amino terminus,
    wherein for each arm of the binding agent, one set of linked first and second humanized $V_HH$ peptide monomers is joined to the amino terminus of the light chain, and one set of linked third and fourth humanized $V_HH$ peptide monomers is joined to the amino terminus of the heavy chain, and wherein the humanized $V_HH$ peptide monomers independently have binding specificity for an epitope of *Clostridium difficile* toxin A (TcdA) or toxin B (TcdB) and are selected from h5D (SEQ ID NO:1), hE3 (SEQ ID NO:2), hAA6 (SEQ ID NO:3) and hAH3 (SEQ ID NO:4), wherein the first, second, third, and fourth humanized $V_HH$ peptide monomers have specificity for one or a combination of epitopes and are selected from h5D (SEQ ID NO: 1), hE3 (SEQ ID NO:2), hAA6 (SEQ ID NO:3) and hAH3 (SEQ ID NO:4).

2. The binding agent of claim 1, each of the first, second, third and fourth humanized $V_HH$ peptide monomers has binding specificity for a different epitope.

3. The binding agent of claim 1, wherein two of the humanized $V_HH$ peptide monomers have binding specificity for epitopes of TcdA and two of the humanized $V_HH$ peptide monomers have binding specificity for epitopes of TcdB.

4. The binding agent of claim 1, wherein the humanized $V_HH$ peptide monomers independently have binding specificity for an epitope in the glucosyltransferase domain, cysteine protease domain, translocation domain or receptor binding domain of TcdA or TcdB.

5. The binding agent of claim 1, wherein the light chain of the binding agent comprises the amino acid sequence set forth in SEQ ID NO:8 (AA6/E3 kappa) or a sequence variant having at least 90% sequence identity thereto, and wherein the heavy chain of the binding agent comprises the amino acid sequence set forth in SEQ ID NO:9 (AH3/5D heavy) or a sequence variant having at least 90% sequence identity thereto.

6. The binding agent of claim 5, wherein variant amino acids of the sequence variant are located in framework regions of the humanized $V_HH$ peptide monomer.

7. The binding agent of claim 1, wherein the two arms comprise constant regions derived from IgG1, IgG2, IgG3 or IgG4.

8. An isolated polynucleotide sequence comprising a nucleotide sequence encoding the light chain arm of the binding agent and the heavy chain arm if the binding agent of claim 1, or a complementary strand thereof.

9. An expression vector comprising the isolated polynucleotide sequence of claim 8.

10. An isolated host cell comprising the isolated polynucleotide sequence of claim 8.

11. A method of producing a binding agent comprising culturing the isolated cell of claim 10 under conditions promoting expression of the binding agent encoded by the expression vector, and recovering the binding agent from the cell culture.

12. A bi-specific or tetra-specific, tetrameric binding agent comprising an IgG antibody and first, second, third and fourth humanized $V_H H$ peptide monomers,
   wherein the IgG antibody comprises two arms, each arm comprising a heavy chain lacking a variable region and a light chain lacking a variable region, and each chain having an amino terminus,
   wherein for a first arm of the antibody, the first humanized $V_H H$ peptide monomer is joined to the amino terminus of the light chain, and the second humanized $V_H H$ peptide monomer is joined to the amino terminus of the heavy chain,
   wherein for a second arm of the antibody, the third humanized $V_H H$ peptide monomer is joined to the amino terminus of the light chain, and the fourth humanized $V_H H$ peptide monomer is joined to the amino terminus of the heavy chain, and
   wherein each of the humanized $V_H H$ peptide monomers has binding specificity for an epitope of *Clostridium difficile* toxin A (TcdA) or toxin B (TcdB) and are selected from h5D (SEQ ID NO:1), hE3 (SEQ ID NO:2), hAA6 (SEQ ID NO:3) and hAH3 (SEQ ID NO:4), wherein the first, second, third, and fourth humanized $V_H H$ peptide monomers have specificity for one or a combination of epitopes and are selected from h5D (SEQ ID NO: 1), hE3 (SEQ ID NO:2), hAA6 (SEQ ID NO:3) and hAH3 (SEQ ID NO:4).

13. A tetra-specific, octameric binding agent comprising an antibody Fc domain and two sets of linked first, second, third and fourth humanized $V_H H$ peptide monomers,
   wherein the antibody Fc domain comprises a first and second arm, each arm comprising hinge, $C_H 2$ and $C_H 3$ regions of an antibody heavy chain, and each arm having an amino terminus,
   wherein for each arm of the Fc domain, one set of linked first, second, third and fourth humanized $V_H H$ peptide monomers is joined to the amino terminus of the arm, and
   wherein the humanized $V_H H$ peptide monomers have binding specificity for an epitope of *Clostridium difficile* toxin A (TcdA) or toxin B (TcdB) and is selected from h5D (SEQ ID NO:1), hE3 (SEQ ID NO:2), hAA6 (SEQ ID NO:3) and hAH3 (SEQ ID NO:4), wherein the first, second, third, and fourth humanized $V_H H$ peptide monomers have specificity for one or a combination of epitopes and are selected from h5D (SEQ ID NO: 1), hE3 (SEQ ID NO:2), hAA6 (SEQ ID NO:3) and hAH3 (SEQ ID NO:4).

14. A bi-specific, tetrameric binding agent comprising an antibody Fc domain and two sets of linked first and second humanized $V_H H$ peptide monomers,
   wherein the antibody Fc domain comprises a first and second arm, each arm comprising hinge, $C_H 2$ and $C_H 3$ regions of an antibody heavy chain, and each arm having an amino terminus,
   wherein for each arm of the Fc domain, one set of linked first and second humanized $V_H H$ peptide monomers is joined to the amino terminus of the arm, and
   wherein the humanized $V_H H$ peptide monomers have binding specificity for an epitope of *Clostridium difficile* toxin A (TcdA) or toxin B (TcdB) and are selected from h5D (SEQ ID NO:1), hE3 (SEQ ID NO:2), hAA6 (SEQ ID NO:3) and hAH3 (SEQ ID NO:4), wherein the first, second, third, and fourth humanized $V_H H$ peptide monomers have specificity for one or a combination of epitopes and are selected from h5D (SEQ ID NO: 1), hE3 (SEQ ID NO:2), hAA6 (SEQ ID NO:3) and hAH3 (SEQ ID NO:4).

15. A humanized $V_H H$ peptide binding agent comprising at least one humanized $V_H H$ peptide monomer, wherein each humanized $V_H H$ peptide monomer has binding specificity for a unique epitope of *Clostridium difficile* toxin A (TcdA) or toxin B (TcdB), wherein the at least one humanized $V_H H$ peptide monomers is selected from h5D (SEQ ID NO:1), hE3 (SEQ ID NO:2), hAA6 (SEQ ID NO:3) and hAH3 (SEQ ID NO:4), wherein the first, second, third, and fourth humanized $V_H H$ peptide monomers have specificity for one or a combination of epitopes and are selected from h5D (SEQ ID NO: 1), hE3 (SEQ ID NO:2), hAA6 (SEQ ID NO:3) and hAH3 (SEQ ID NO:4).

16. A pharmaceutical formulation comprising a binding agent of claim 1 and a pharmaceutically acceptable carrier or diluent.

17. A method of treating or preventing a disease symptom induced by *C. difficile* in a subject comprising administering a therapeutically-effective amount of the binding agent of claim 1 to a subject having *C. difficile* infection or a risk of developing *C. difficile* infection.

18. A method of neutralizing *C. difficile* toxin TcdA and/or TcdB in a subject infected by *C. difficile* comprising administering a therapeutically-effective amount of the binding agent of claim 1 to a subject having *C. difficile* infection.

19. A method of treating or preventing *C. difficile* infection in a subject comprising administering a therapeutically-effective amount of the binding agents of claim 1 to a subject having *C. difficile* infection or a risk of developing *C. difficile* infection.

* * * * *

SEQUENCE LISTING

```
<160> NUMBER OF SEQ ID NOS: 39

<210> SEQ ID NO 1
<211> LENGTH: 127
<212> TYPE: PRT
<213> ORGANISM: Artificial Sequence
<220> FEATURE:
<223> OTHER INFORMATION: Humanized VHH peptide monomer 5D

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Gly Ile Gly Trp Phe Arg Gln Ala Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Arg Phe Ser Ala Ser Ser Val Asn Arg Trp Leu Ala Asp
            100                 105                 110

Asp Tyr Asp Val Trp Gly Gln Gly Thr Leu Val Thr Val Ser Ser
```

-continued

```
            115                 120                 125

<210> SEQ ID NO 2
<211> LENGTH: 111
<212> TYPE: PRT
<213> ORGANISM: Artificial Sequence
<220> FEATURE:
<223> OTHER INFORMATION: Humanized VHH peptide monomer E3

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Ile Ala Gly Phe Glu
            20                  25                  30

Thr Val Thr Trp Ser Arg Gln Ala Pro Gly Lys Ser Leu Gln Trp Val
        35                  40                  45

Ala Ser Met Thr Lys Thr Asn Asn Glu Ile Tyr Ser Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Lys
                85                  90                  95

Gly Pro Glu Leu Arg Gly Gln Gly Thr Leu Val Thr Val Ser Ser
            100                 105                 110

<210> SEQ ID NO 3
<211> LENGTH: 121
<212> TYPE: PRT
<213> ORGANISM: Artificial Sequence
<220> FEATURE:
<223> OTHER INFORMATION: Humanized VHH peptide monomer AA6

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Val Ile Ser Ala Ser Ala Ile Arg Gly Ala Val Arg Gly
            100                 105                 110

Gln Gly Thr Leu Val Thr Val Ser Ser
        115                 120

<210> SEQ ID NO 4
<211> LENGTH: 127
<212> TYPE: PRT
<213> ORGANISM: Artificial Sequence
<220> FEATURE:
<223> OTHER INFORMATION: Humanized VHH peptide monomer AH3

<400> SEQUENCE: 4

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Ser Gly Asp Ser Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Phe Arg Ala Thr Met Cys Gly Val Phe Pro Leu Ser Pro Tyr
            100                 105                 110

Gly Lys Asp Asp Trp Gly Gln Gly Thr Leu Val Thr Val Ser Ser
        115                 120                 125

<210> SEQ ID NO 5
<211> LENGTH: 15
<212> TYPE: PRT
<213> ORGANISM: Artificial Sequence
<220> FEATURE:
<223> OTHER INFORMATION: Codon-optimized flexible linker 1

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Codon-optimized flexible linker 2

<400> SEQUENCE: 6

Gly Gly Gly Ser Gly Gly Gly Ser Gly Gly Gly Ser Gly Gly Gly Ser
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Codon-optimized flexible linker 3

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 354
<212> TYPE: PRT
<213> ORGANISM: Artificial Sequence
<220> FEATURE:
<223> OTHER INFORMATION: hAA6-hE3 kappa light chain of FZ003 binding
      agent

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
```

```
                35                  40                  45
Ala Thr Ile Asn Thr Asp Gly Ser Thr Met Arg Asp Asp Ser Thr Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Arg Val Ile Ser Ala Ser Ala Ile Arg Gly Ala Val Arg Gly
            100                 105                 110

Gln Gly Thr Leu Val Thr Val Ser Ser Gly Gly Gly Ser Gly Gly
            115                 120                 125

Gly Gly Ser Gly Gly Gly Ser Glu Val Gln Leu Leu Glu Ser Gly
        130                 135                 140

Gly Gly Leu Val Gln Pro Gly Gly Ser Leu Arg Leu Ser Cys Ala Ala
145                 150                 155                 160

Ser Gly Ser Ile Ala Gly Phe Glu Thr Val Thr Trp Ser Arg Gln Ala
                165                 170                 175

Pro Gly Lys Ser Leu Gln Trp Val Ala Ser Met Thr Lys Thr Asn Asn
            180                 185                 190

Glu Ile Tyr Ser Asp Ser Val Lys Gly Arg Phe Thr Ile Ser Arg Asp
        195                 200                 205

Asn Ser Lys Asn Thr Val Tyr Leu Gln Met Asn Ser Leu Arg Ala Glu
    210                 215                 220

Asp Thr Ala Val Tyr Tyr Cys Lys Gly Pro Glu Leu Arg Gly Gln Gly
225                 230                 235                 240

Thr Leu Val Thr Val Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys

<210> SEQ ID NO 9
<211> LENGTH: 599
<212> TYPE: PRT
<213> ORGANISM: Artificial Sequence
<220> FEATURE:
<223> OTHER INFORMATION: hAH3-h5D heavy chain of FZ003 binding agent

<400> SEQUENCE: 9

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45
```

```
Ser Cys Ile Ser Ser Ser Gly Asp Ser Thr Lys Tyr Ala Asp Ser Val
    50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ala Phe Arg Ala Thr Met Cys Gly Val Phe Pro Leu Ser Pro Tyr
                100                 105                 110
Gly Lys Asp Asp Trp Gly Gln Gly Thr Leu Val Thr Val Ser Ser Gly
            115                 120                 125
Gly Gly Gly Ser Gly Gly Gly Ser Gly Gly Gly Ser Glu Val
        130                 135                 140
Gln Leu Leu Glu Ser Gly Gly Gly Leu Val Gln Pro Gly Gly Ser Leu
145                 150                 155                 160
Arg Leu Ser Cys Ala Ala Ser Gly Phe Thr Leu Asp Tyr Tyr Gly Ile
                165                 170                 175
Gly Trp Phe Arg Gln Ala Pro Gly Lys Glu Arg Glu Ala Val Ser Tyr
            180                 185                 190
Ile Ser Ala Ser Ala Arg Thr Ile Leu Tyr Ala Asp Ser Val Lys Gly
        195                 200                 205
Arg Phe Thr Ile Ser Arg Asp Asn Ser Lys Asn Thr Leu Tyr Leu Gln
210                 215                 220
Met Asn Ser Leu Arg Ala Glu Asp Thr Ala Val Tyr Tyr Cys Ala Arg
225                 230                 235                 240
Arg Arg Phe Ser Ala Ser Ser Val Asn Arg Trp Leu Ala Asp Asp Tyr
                245                 250                 255
Asp Val Trp Gly Gln Gly Thr Leu Val Thr Val Ser Ser Ala Ser Thr
            260                 265                 270
Lys Gly Pro Ser Val Phe Pro Leu Ala Pro Ser Ser Lys Ser Thr Ser
        275                 280                 285
Gly Gly Thr Ala Ala Leu Gly Cys Leu Val Lys Asp Tyr Phe Pro Glu
    290                 295                 300
Pro Val Thr Val Ser Trp Asn Ser Gly Ala Leu Thr Ser Gly Val His
305                 310                 315                 320
Thr Phe Pro Ala Val Leu Gln Ser Ser Gly Leu Tyr Ser Leu Ser Ser
                325                 330                 335
Val Val Thr Val Pro Ser Ser Ser Leu Gly Thr Gln Thr Tyr Ile Cys
            340                 345                 350
Asn Val Asn His Lys Pro Ser Asn Thr Lys Val Asp Lys Arg Val Glu
        355                 360                 365
Pro Lys Ser Cys Asp Lys Thr His Thr Cys Pro Pro Cys Pro Ala Pro
370                 375                 380
Glu Leu Leu Gly Gly Pro Ser Val Phe Leu Phe Pro Pro Lys Pro Lys
385                 390                 395                 400
Asp Thr Leu Met Ile Ser Arg Thr Pro Glu Val Thr Cys Val Val Val
                405                 410                 415
Asp Val Ser His Glu Asp Pro Glu Val Lys Phe Asn Trp Tyr Val Asp
            420                 425                 430
Gly Val Glu Val His Asn Ala Lys Thr Lys Pro Arg Glu Glu Gln Tyr
        435                 440                 445
Asn Ser Thr Tyr Arg Val Val Ser Val Leu Thr Val Leu His Gln Asp
    450                 455                 460
```

Trp Leu Asn Gly Lys Glu Tyr Lys Cys Lys Val Ser Asn Lys Ala Leu
465                 470                 475                 480

Pro Ala Pro Ile Glu Lys Thr Ile Ser Lys Ala Lys Gly Gln Pro Arg
                485                 490                 495

Glu Pro Gln Val Tyr Thr Leu Pro Pro Ser Arg Glu Glu Met Thr Lys
            500                 505                 510

Asn Gln Val Ser Leu Thr Cys Leu Val Lys Gly Phe Tyr Pro Ser Asp
        515                 520                 525

Ile Ala Val Glu Trp Glu Ser Asn Gly Gln Pro Glu Asn Asn Tyr Lys
    530                 535                 540

Thr Thr Pro Pro Val Leu Asp Ser Asp Gly Ser Phe Phe Leu Tyr Ser
545                 550                 555                 560

Lys Leu Thr Val Asp Lys Ser Arg Trp Gln Gln Gly Asn Val Phe Ser
                565                 570                 575

Cys Ser Val Met His Glu Ala Leu His Asn His Tyr Thr Gln Lys Ser
            580                 585                 590

Leu Ser Leu Ser Pro Gly Lys
        595

<210> SEQ ID NO 10
<211> LENGTH: 1064
<212> TYPE: DNA
<213> ORGANISM: Artificial Sequence
<220> FEATURE:
<223> OTHER INFORMATION: polynucleotide sequence encoding the hAA6-hE3 kappa light chain of FZ003 binding agent

<400> SEQUENCE: 10

```
gaggtgcagc tgctggagag cggaggagga ctggtgcagc ctggaggatc cctgaggctg      60
tcttgcgcag caagcggctt cacctttagc gactacgtga tgacatgggt cgcccaggca     120
ccaggcaagg gacctgagtg gatcgccacc atcaacacag atggctccac catgagggac     180
gattctacca agggccggtt cacaatctcc agagacaact ctaagaatac cctgtatctg     240
cagatgaata gcctgcgggc cgaggataca gccgtgtact attgcgcaag ggaagagtg      300
atctccgcct ctgccatcag gggagccgtg cgcggacagg gcaccctggt gacagtgagc     360
tccggaggag gaggatccgg cggaggaggc tctggcggcg gcggcagcga agtccagctg     420
ctggaatctg gcgcggggcct ggtgcagcca ggcggcagcc tgcggctgtc ctgtgccgcc     480
agcggctcca tcgccggctt cgagaccgtg acatggtcta gacaggcacc aggcaagagc     540
ctgcagtggg tggcctccat gaccaagaca aacaatgaga tctactctga cagcgtgaag     600
ggcaggttta ccatctctcg cgataacagc aagaatacag tgtatctgca gatgaactcc     660
ctgagggcag aggacaccgc cgtgtactat tgtaagggac agagctgag aggcaggggg     720
acactcgtca ccgtgtctag ccgtacggtg gctgcaccat ctgtcttcat cttcccgcca     780
tctgatgagc agttgaaatc tggaactgcc tctgttgtgt gcctgctgaa taacttctat     840
cccagagagg ccaaagtaca gtggaaggtg gataacgccc tccaatcggg taactcccag     900
gagagtgtca cagagcagga cagcaaggac agcacctaca gcctcagcag cacctgacg     960
ctgagcaaag cagactacga gaaacacaaa gtctacgcct gcgaagtcac ccatcagggc    1020
ctgagctcgc ccgtcacaaa gagcttcaac aggggagagt gtta                     1064
```

<210> SEQ ID NO 11
<211> LENGTH: 1799
<212> TYPE: DNA
<213> ORGANISM: Artificial Sequence
<220> FEATURE:
<223> OTHER INFORMATION: polynucleotide sequence encoding the hAH3-h5D heavy chain of FZ003 binding agent

<400> SEQUENCE: 11

```
gaggtgcagc tgctggagag cggaggagga ctggtgcagc caggaggatc cctgaggctg      60
tcttgcgcag caagcggctt caccctggac tacagctcca tcggatggtt taggcaggca     120
ccaggcaagg agagggaggg cgtgtcctgt atctctagct ccggcgactc tacaaagtac     180
gccgatagcg tgaagggccg cttcaccatc tcccgggaca actctaagaa tacactgtat     240
ctgcagatga actctctgcg cgccgaggat accgccgtgt actattgcgc cgccttccgg     300
gcaacaatgt gcggcgtgtt tcccctgtcc ccttatggca aggacgattg gggccagggc     360
accctggtga cagtgtctag cggaggagga ggatctggag gaggaggaag cggaggagga     420
ggatccgaag tccagctgct ggaatctggc ggcggcctgg tgcagcctgg cggcagcctg     480
aggctgtcct gcgcagcatc tggcttcacc ctgattact atggcatcgg ctggtttaga     540
caggcccctg gcaaggagag ggaggccgtg tcctacatct gccagcgc ccggacaatc     600
ctgtatgccg actctgtgaa gggcagattc accatcagca ggataactc caagaataca     660
ctgtacctgc agatgaacag cctgagagcc gaggacaccg ccgtgtacta ttgtgcccgg     720
agaaggtttt ccgcctcctc tgtgaatagg tggctggccg acgattatga cgtgtgggga     780
caggggacac tcgtcacagt gagctccgcg tcgaccaagg gcccatcggt cttcccgcta     840
gcaccctcct ccaagagcac ctctgggggc acagcggccc tgggctgcct ggtcaaggac     900
tacttccccg aacctgtgac ggtctcgtgg aactcaggcg ccctgaccag cggcgtgcac     960
accttcccgg ctgtcctaca gtcctcagga ctctactccc tcagcagcgt ggtgaccgtg    1020
ccctccagca gcttgggcac ccagacctac atctgcaacg tgaatcacaa gcccagcaac    1080
accaaggtgg acaagagagt tgagcccaaa tcttgtgaca aaactcacac atgcccaccg    1140
tgcccagcac ctgaactcct ggggggaccg tcagtcttcc tcttcccccc aaaacccaag    1200
gacaccctca tgatctcccg gacccctgag gtcacatgcg tggtggtgga cgtgagccac    1260
gaagaccctg aggtcaagtt caactggtac gtggacggcg tggaggtgca taatgccaag    1320
acaaagccgc gggaggagca gtacaacagc acgtaccgtg tggtcagcgt cctcaccgtc    1380
ctgcaccagg actggctgaa tggcaaggag tacaagtgca aggtctccaa caaagccctc    1440
ccagccccca tcgagaaaac catctccaaa gccaaagggc agccccgaga accacaggtg    1500
tacaccctgc cccatcccg ggaggagatg accaagaacc aggtcagcct gacctgcctg    1560
gtcaaaggct tctatcccag cgacatcgcc gtggagtggg agagcaatgg gcagccggag    1620
aacaactaca agaccacgcc tcccgtgctg gactccgacg gctccttctt cctctatagc    1680
aagctcaccg tggacaagag caggtggcag caggggaacg tcttctcatg ctccgtgatg    1740
catgaggctc tgcacaacca ctacacgcag aagagcctct ccctgtcccc gggtaaatg    1799
```

<210> SEQ ID NO 12
<211> LENGTH: 6459
<212> TYPE: DNA
<213> ORGANISM: Artificial Sequence
<220> FEATURE:
<223> OTHER INFORMATION: expression vector comprising the polynucleotide sequence encoding the hAA6-hE3 kappa light chain of FZ003 binding agent

<400> SEQUENCE: 12

```
ttcgagctcg cccgacattg attattgact agttattaat agtaatcaat tacggggtca     60
```

```
ttagttcata gcccatatat ggagttccgc gttacataac ttacggtaaa tggcccgcct    120
ggctgaccgc ccaacgaccc ccgcccattg acgtcaataa tgacgtatgt tcccatagta    180
acgccaatag ggactttcca ttgacgtcaa tgggtggagt atttacggta aactgcccac    240
ttggcagtac atcaagtgta tcatatgcca agtacgcccc ctattgacgt caatgacggt    300
aaatggcccg cctggcatta tgcccagtac atgaccttat gggactttcc tacttggcag    360
tacatctacg tattagtcat cgctattacc atggtgatgc ggttttggca gtacatcaat    420
gggcgtggat agcggtttga ctcacgggga tttccaagtc tccaccccat tgacgtcaat    480
gggagtttgt tttggcacca aaatcaacgg gactttccaa aatgtcgtaa caactccgcc    540
ccattgacgc aaatgggcgg taggcgtgta cggtgggagg tctatataag cagagctcgt    600
ttagtgaacc gtcagatcgc ctggagacgc catccacgct gttttgacct ccatagaaga    660
caccgggacc gatccagcct ccgcggccgg gaacggtgca ttggaacgcg gattccccgt    720
gccaagagtg acgtaagtac cgcctataga gtctataggc ccaccccctt ggcttcgtta    780
gaacgcggct acaattaata cataaccttat tgtatcatac atacgattt aggtgacac    840 tatagaataa catccacttt gcctttctct ccacaggtgt ccactcccag gtccaactgc    900
acctcggttc tatcgattga attccaccat gggatggtca tgtatcatcc tttttctagt    960
agcaactgca accggtgtac attccgaggt gcagctgctg gagagcggag gaggactggt   1020
gcagcctgga ggatccctga ggctgtcttg cgcagcaagc ggcttcacct ttagcgacta   1080
cgtgatgaca tgggtgcgcc aggcaccagg caagggacct gagtggatcg ccaccatcaa   1140
cacagatggc tccaccatga gggacgattc taccaagggc cggttcacaa tctccagaga   1200
caactctaag aataccctgt atctgcagat gaatagcctg cgggccgagg atacagccgt   1260
gtactattgc gcaaggggaa gagtgatctc cgcctctgcc atcaggggag ccgtgcgcgg   1320
acagggcacc ctggtgacag tgagctccgg aggaggagga tccggcggag gaggctctgg   1380
cggcggcggc agcgaagtcc agctgctgga atctggcggc ggcctggtgc agccaggcgg   1440
cagcctgcgg ctgtcctgtg ccgccagcgg ctccatcgcc ggcttcgaga ccgtgacatg   1500
gtctagacag gcaccaggca agagcctgca gtgggtggcc tccatgacca agacaaacaa   1560
tgagatctac tctgacagcg tgaagggcag gtttaccatc tctcgcgata cagcaagaa   1620 tacagtgtat ctgcagatga actccctgag ggcagaggac accgccgtgt actattgtaa   1680
gggaccagag ctgagaggcc aggggacact cgtcaccgtg tctagccgta cggtggctgc   1740
accatctgtc ttcatcttcc cgccatctga tgagcagttg aaatctggaa ctgcctctgt   1800
tgtgtgcctg ctgaataact tctatcccag agaggccaaa gtacagtgga aggtggataa   1860
cgccctccaa tcgggtaact cccaggagag tgtcacagag caggacagca aggacagcac   1920
ctacagcctc agcagcaccc tgacgctgag caaagcagac tacgagaaac acaaagtcta   1980
cgcctgcgaa gtcacccatc agggcctgag ctcgcccgtc acaaagagct tcaacagggg   2040
agagtgttag gcggccgcaa gcttggcccg tttaaacccg ctgatcagcc tcgactgtgc   2100
cttctagttg ccagccatct gttgtttgcc cctcccccgt gccttccttg accctggaag   2160
gtgccactcc cactgtcctt tcctaataaa atgaggaaat tgcatcgcat tgtctgagta   2220
ggtgtcattc tattctgggg ggtggggtgg ggcaggacag caaggggag gattgggaag   2280 acaatagcag gcatgctggg gatgcggtgg gctctatggc ttctgaggcg gaaagaacca   2340 gctgggctc taggggtat ccccacgcgc cctgtagcgg cgcattaagc gcggcgggtg   2400
```

```
tggtggttac gcgcagcgtg accgctacac ttgccagcgc cctagcgccc gctcctttcg    2460 cttttcttccc ttcctttctc gccacgttcg ccggctttcc ccgtcaagct ctaaatcggg   2520
ggctcccttt aggggttccga tttagtgctt tacggcacct cgaccccaaa aaacttgatt   2580
agggtgatgg ttcacgtagt gggccatcgc cctgatagac ggttttttcgc cctttgacgt   2640 tggagtccac gttctttaat agtggactct tgttccaaac tggaacaaca ctcaaccta    2700 tctcggtcta ttcttttgat ttataaggga ttttgccgat ttcggcctat tggttaaaaa    2760
atgagctgat ttaacaaaaa tttaacgcga attaattctg tggaatgtgt gtcagttagg   2820
gtgtggaaag tccccaggct ccccagcagg cagaagtatg caaagcatgc atctcaatta    2880
gtcagcaacc aggtgtggaa agtccccagg ctccccagca ggcagaagta tgcaaagcat   2940
gcatctcaat tagtcagcaa ccatagtccc gcccctaact ccgcccatcc cgcccctaac   3000
tccgcccagt tccgcccatt ctccgcccca tggctgacta ttttttttta tttatgcaga    3060
ggccgaggcc gcctctgcct ctgagctatt ccagaagtag tgaggaggct ttttggagg    3120 cctaggcttt tgcaaaaagc tcccgggagc ttgtatatcc attttcggat ctgatcagca   3180
cgtgatggtt cgaccattga actgcatcgt cgccgtgtcc caaaatatgg ggattggcaa   3240
gaacggagac ctaccctggc ctccgctcag gaacgagttc aagtacttcc aaagaatgac   3300
cacaacctct tcagtggaag gtaaacagaa tctggtgatt atgggtagga aaacctggtt   3360
ctccattcct gagaagaatc gaccattaaa ggacagaatt aatatagttc tcagtagaga   3420
actcaaagaa ccaccacgag gagcacattt tcttgccaaa agtttggatg atgccttaag   3480
acttattgaa caaccggaat tggcaagtaa agttgacatg gtttggatag tcggaggcag   3540
ttctgtttac caggaagcca tgaatcaacc aggccacctc agactctttg tgacaaggat   3600
catgcaggaa tttgaaagtg acacgttttt cccagaaatt gatttgggga aatataaact    3660
tctcccagaa tacccaggcg tcctctctga ggtccaggag gaaaaaggca tcaagtataa   3720
gtttgaagtt tacgagaaga agactaata gcacgtgcta cgagatttcg attccaccgc    3780
cgccttctat gaaaggttgg gcttcggaat cgttttccgg gacgccggct ggatgatcct   3840
ccagcgcggg gatctcatgc tggagttctt cgcccacccc aacttgttta ttgcagctta   3900
taatggttac aaataaagca atagcatcac aaatttcaca aataaagcat ttttttcact   3960
gcattctagt tgtggtttgt ccaaactcat caatgtatct tatcatgtct ggatcggaa    4020 ttaattcggc gcagcaccat ggcctgaaat aacctctgaa agaggaactt ggttaggtac   4080
cttctgaggc ggaaagaacc atctgtggaa tgtgtgtcag ttagggtgtg aaagtcccc    4140 aggctcccca gcaggcagaa gtatgcaaag ccgggagctg catgtgtcag aggttttcac   4200
cgtcatcacc gaaacgcgcg agacgaaagg gcctcgtgat acgcctattt ttataggtta   4260
atgtcatgat aataatggtt tcttagacgt caggtggcac ttttcgggga aatgtgcgcg   4320 gaaccctat ttgttttattt ttctaaatac attcaaatat gtatccgctc atgagacaat   4380
aaccctgata aatgcttcaa taatattgaa aaaggaagag tatgagtatt caacatttcc   4440
gtgtcgccct tattcccttt tttgcggcat tttgccttcc tgttttttgct cacccagaaa   4500 cgctggtgaa agtaaaagat gctgaagatc agttgggtgc acgagtgggt tacatcgaac   4560
tggatctcaa cagcggtaag atccttgaga gttttcgccc cgaagaacgt tttccaatga    4620
tgagcacttt taaagttctg ctatgtggcg cggtattatc ccgtattgac gccgggcaag   4680
agcaactcgg tcgccgcata cactattctc agaatgactt ggttgagtac tcaccagtca    4740
cagaaaagca tcttacggat ggcatgacag taagagaatt atgcagtgct gccataacca   4800
```

```
tgagtgataa cactgcggcc aacttacttc tgacaacgat cggaggaccg aaggagctaa    4860 ccgcttttt  gcacaacatg ggggatcatg taactcgcct tgatcgttgg gaaccggagc    4920
tgaatgaagc cataccaaac gacgagcgtg acaccacgat gcctgtagca atggcaacaa    4980
cgttgcgcaa actattaact ggcgaactac ttactctagc ttcccggcaa caattaatag    5040
actggatgga ggcggataaa gttgcaggac cacttctgcg ctcggccctt ccggctggct    5100
ggtttattgc tgataaatct ggagccgtg agcgtgggtc tcgcggtatc attgcagcac     5160
tggggccaga tggtaagccc tcccgtatcg tagttatcta cacgacgggg agtcaggcaa    5220
ctatggatga cgaaataga cagatcgctg agataggtgc ctcactgatt aagcattggt     5280
aactgtcaga ccaagtttac tcatatatac tttagattga tttaaaactt cattttaat    5340 ttaaaaggat ctaggtgaag atccttttg ataatctcat gaccaaaatc ccttaacgtg     5400
agttttcgtt ccactgagcg tcagacccg tagaaaagat caaaggatct tcttgagatc     5460 cttttttct  gcgcgtaatc tgctgcttgc aaacaaaaaa accaccgcta ccagcggtgg    5520 tttgttgcc  ggatcaagag ctaccaactc ttttccgaa ggtaactggc ttcagcagag     5580
cgcagatacc aaatactgtt cttctagtgt agccgtagtt aggccaccac ttcaagaact    5640
ctgtagcacc gcctacatac ctcgctctgc taatcctgtt accagtggct gctgccagtg    5700
gcgataagtc gtgtcttacc gggttggact caagacgata gttaccggat aaggcgcagc    5760
ggtcgggctg aacggggggt tcgtgcacac agcccagctt ggagcgaacg acctacaccg    5820
aactgagata cctacagcgt gagctatgag aaagcgccac gcttcccga  agggagaaag    5880 gcggacaggt atccggtaag cggcagggtc ggaacaggag agcgcacgag ggagcttcca    5940
gggggaaacg cctggtatct ttatagtcct gtcgggttc  gccacctctg acttgagcgt    6000
cgatttttgt gatgctcgtc aggggggcgg agcctatgga aaaacgccag caacgcggcc    6060 ttttacggt  tcctggcctt tgctggcct  tttgctcaca tgttcttcc  tgcgttatcc    6120 cctgattctg tggataaccg tattaccgcc tttgagtgag ctgataccgc tcgccgcagc    6180
cgaacgaccg agcgcagcga gtcagtgagc gaggaagcgg aagagcgccc aatacgcaaa    6240
ccgcctctcc ccgcgcgttg gccgattcat taatccaact ggcacgacag gtttcccgac    6300
tggaaagcgg gcagtgagcg caacgcaatt aatgtgagtt agctcactca ttaggcaccc    6360
caggctttac actttatgct tccggctcgt atgttgtgtg gaattgtgag cggataacaa    6420
tttcacacag gaaacagcta tgacatgatt acgaattaa                           6459
```

<210> SEQ ID NO 13
<211> LENGTH: 7067
<212> TYPE: DNA
<213> ORGANISM: Artificial Sequence
<220> FEATURE:
<223> OTHER INFORMATION: expression vector comprising the polynucleotide
      sequence encoding the hAH3-h5D heavy chain of FZ003 binding agent

<400> SEQUENCE: 13

```
ttcgagctcg cccgacattg attattgact agttattaat agtaatcaat tacggggtca      60
ttagttcata gcccatatat ggagttccgc gttacataac ttacggtaaa tggcccgcct     120
ggctgaccgc ccaacgaccc ccgcccattg acgtcaataa tgacgtatgt tcccatagta     180
acgccaatag ggactttcca ttgacgtcaa tgggtggagt atttacggta aactgcccac     240
ttggcagtac atcaagtgta tcatatgcca agtacgcccc ctattgacgt caatgacggt     300
aaatggcccg cctggcatta tgcccagtac atgaccttat gggactttcc tacttggcag    360
```

```
tacatctacg tattagtcat cgctattacc atggtgatgc ggttttggca gtacatcaat    420
gggcgtggat agcggtttga ctcacgggga tttccaagtc tccacccat tgacgtcaat    480 gggagtttgt tttggcacca aaatcaacgg gactttccaa aatgtcgtaa caactccgcc   540
ccattgacgc aaatgggcgg taggcgtgta cggtgggagg tctatataag cagagctcgt   600
ttagtgaacc gtcagatcgc ctggagacgc catccacgct gttttgacct ccatagaaga   660
caccgggacc gatccagcct ccgcggccgg aacggtgcat tggaacgcg gattccccgt    720 gccaagagtg acgtaagtac cgcctataga gtctataggc ccacccctt ggcttcgtta    780 gaacgcggct acaattaata cataaccta tgtatcatac acatcgatt taggtgacac     840 tatagaataa catccacttt gcctttctct ccacaggtgt ccactcccag gtccaactgc   900
acctcggttc tatcgattga attccaccat gggatggtca tgtatcatcc ttttctagt    960 agcaactgca accggtgtac attccgaggt gcagctgctg gagagcggag gaggactggt   1020
gcagccagga ggatccctga ggctgtcttg cgcagcaagc ggcttcaccc tggactacag   1080
ctccatcgga tggtttaggc aggcaccagg caaggagagg gagggcgtgt cctgtatctc   1140
tagctccggc gactctacaa agtacgccga tagcgtgaag ggccgcttca ccatctcccg   1200
ggacaactct aagaatacac tgtatctgca gatgaactct ctgcgcgccg aggataccgc   1260
cgtgtactat tgcgccgcct tccgggcaac aatgtgcggc gtgttcccc tgtccccta    1320 tggcaaggac gattggggcc agggcaccct ggtgacagtg tctagcggag gaggaggatc   1380
tggaggagga ggaagcggag gaggaggatc cgaagtccag ctgctggaat ctggcggcgg   1440
cctggtgcag cctggcggca gcctgaggct gtcctgcgca gcatctggct tcaccctgga   1500
ttactatggc atcggctggt ttagacaggc ccctggcaag gagagggagg ccgtgtccta   1560
catctctgcc agcgcccgga caatcctgta tgccgactct gtgaagggca gattcaccat   1620
cagcagggat aactccaaga atacactgta cctgcagatg aacagcctga gccgcgagga   1680
caccgccgtg tactattgtg cccggagaag gtttttccgcc tcctctgtga ataggtggct   1740
ggccgacgat tatgacgtgt ggggacaggg gacactcgtc acagtgagct ccgcgtcgac   1800
caagggccca tcggtcttcc cgctagcacc ctcctccaag agcacctctg ggggcacagc   1860
ggccctgggc tgcctggtca aggactactt ccccgaacct gtgacggtct cgtggaactc   1920
aggcgccctg accagcggcg tgcacacctt cccggctgtc ctacagtcct caggactcta   1980
ctccctcagc agcgtggtga ccgtgccctc cagcagcttg ggcacccaga cctacatctg   2040
caacgtgaat cacaagccca gcaacaccaa ggtggacaag agagttgagc ccaaatcttg   2100
tgacaaaact cacacatgcc caccgtgccc agcacctgaa ctcctggggg gaccgtcagt   2160
cttcctcttc cccccaaaac ccaaggacac cctcatgatc tcccggaccc ctgaggtcac   2220
atgcgtggtg gtggacgtga gccacgaaga ccctgaggtc aagttcaact ggtacgtgga   2280
cggcgtggag gtgcataatg ccaagacaaa gccgcgggag gagcagtaca acagcacgta   2340
ccgtgtggtc agcgtcctca ccgtcctgca ccaggactgg ctgaatggca aggagtacaa   2400
gtgcaaggtc tccaacaaag ccctcccagc ccccatcgag aaaaccatct ccaaagccaa   2460
agggcagccc cgagaaccac aggtgtacac cctgccccca tcccgggagg agatgaccaa   2520
gaaccaggtc agcctgacct gcctggtcaa aggcttctat cccagcgaca tcgccgtgga   2580
gtgggagagc aatgggcagc cggagaacaa ctacaagacc acgcctcccg tgctggactc   2640
cgacggctcc ttcttcctct atagcaagct caccgtggac aagagcaggt ggcagcaggg   2700
```

-continued

```
gaacgtcttc tcatgctccg tgatgcatga ggctctgcac aaccactaca cgcagaagag     2760
cctctccctg tccccgggta aatgagcggc cgcaagcttg gcccgtttaa acccgctgat     2820
cagcctcgac tgtgccttct agttgccagc catctgttgt ttgcccctcc cccgtgcctt     2880
ccttgaccct ggaaggtgcc actcccactg tcctttccta ataaaatgag gaaattgcat     2940
cgcattgtct gagtaggtgt cattctattc tggggggtgg ggtggggcag gacagcaagg     3000
gggaggattg ggaagacaat agcaggcatg ctggggatgc ggtgggctct atggcttctg     3060
aggcggaaag aaccagctgg ggctctaggg ggtatcccca cgcgccctgt agcggcgcat     3120
taagcgcggc gggtgtggtg gttacgcgca gcgtgaccgc tacacttgcc agcgccctag     3180
cgcccgctcc tttcgctttc ttcccttcct ttctcgccac gttcgccggc tttccccgtc     3240
aagctctaaa tcgggggctc cctttagggt tccgatttag tgctttacgg cacctcgacc     3300
ccaaaaaact tgattagggt gatggttcac gtagtgggcc atcgccctga tagacggttt     3360
ttcgcccttt gacgttggag tccacgttct ttaatagtgg actcttgttc caaactggaa     3420
caacactcaa ccctatctcg gtctattctt ttgatttata agggattttg ccgatttcgg     3480
cctattggtt aaaaaatgag ctgatttaac aaaaatttaa cgcgaattaa ttctgtggaa     3540
tgtgtgtcag ttagggtgtg gaaagtcccc aggctcccca gcaggcagaa gtatgcaaag     3600
catgcatctc aattagtcag caaccaggtg tggaaagtcc ccaggctccc cagcaggcag     3660
aagtatgcaa agcatgcatc tcaattagtc agcaaccata gtcccgcccc taactccgcc     3720
catcccgccc ctaactccgc ccagttccgc ccattctccg ccccatggct gactaatttt     3780
ttttatttat gcagaggccg aggccgcctc tgcctctgag ctattccaga agtagtgagg     3840 aggcttttt ggaggcctag gcttttgcaa aaagctcccg ggagcttgta tatccatttt     3900
cggatctgat cagcacgtgt tgacaattaa tcatcggcat agtatatcgg catagtataa     3960
tacgacaagg tgaggaacta aaccatggcc aagttgacca gtgccgttcc ggtgctcacc     4020
gcgcgcgacg tcgccggagc ggtcgagttc tggaccgacc ggctcgggtt ctcccgggac     4080
ttcgtggagg acgacttcgc cggtgtggtc cgggacgacg tgaccctgtt catcagcgcg     4140
gtccaggacc aggtggtgcc ggacaacacc ctggcctggg tgtgggtgcg cggcctggac     4200
gagctgtacg ccgagtggtc ggaggtcgtg tccacgaact tccgggacgc ctccgggccg     4260
gccatgaccg agatcggcga gcagccgtgg gggcgggagt cgccctgcg cgacccggcc     4320 ggcaactgcg tgcacttcgt ggccgaggag caggactgac acgtgctacg agatttcgat     4380
tccaccgccg ccttctatga aaggttgggc ttcggaatcg ttttccggga cgccggctgg     4440
atgatcctcc agcgcgggga tctcatgctg gagttcttcg cccaccccaa cttgtttatt     4500
gcagcttata atggttacaa ataaagcaat agcatcacaa atttcacaaa taaagcattt     4560
ttttcactgc attctagttg tggtttgtcc aaactcatca atgtatctta tcatgtctgg     4620
atcgggaatt aattcggcgc agcaccatgg cctgaaataa cctctgaaag aggaacttgg     4680
ttaggtacct tctgaggcgg aaagaaccat ctgtggaatg tgtgtcagtt agggtgtgga     4740
aagtccccag gctccccagc aggcagaagt atgcaaagcc gggagctgca tgtgtcagag     4800
gttttcaccg tcatcaccga aacgcgcgag acgaaagggc ctcgtgatac gcctattttt     4860
ataggttaat gtcatgataa taatggtttc ttagacgtca ggtggcactt ttcggggaaa     4920
tgtgcgcgga accctatt gtttattttt ctaaatacat tcaaatatgt atccgctcat     4980
gagacaataa ccctgataaa tgcttcaata atattgaaaa aggaagagta tgagtattca     5040
acatttccgt gtcgccctta ttcccttttt tgcggcattt tgccttcctg tttttgctca     5100
```

```
cccagaaacg ctggtgaaag taaaagatgc tgaagatcag ttgggtgcac gagtgggtta    5160
catcgaactg gatctcaaca gcggtaagat ccttgagagt tttcgccccg aagaacgttt    5220
tccaatgatg agcacttta aagttctgct atgtggcgcg gtattatccc gtattgacgc     5280
cgggcaagag caactcggtc gccgcataca ctattctcag aatgacttgg ttgagtactc    5340
accagtcaca gaaaagcatc ttacggatgg catgacagta agagaattat gcagtgctgc    5400
cataaccatg agtgataaca ctgcggccaa cttacttctg acaacgatcg gaggaccgaa    5460
ggagctaacc gcttttttgc acaacatggg ggatcatgta actcgccttg atcgttggga    5520
accggagctg aatgaagcca taccaaacga cgagcgtgac accacgatgc ctgtagcaat    5580
ggcaacaacg ttgcgcaaac tattaactgg cgaactactt actctagctt cccggcaaca    5640
attaatagac tggatggagg cggataaagt tgcaggacca cttctgcgct cggcccttcc    5700
ggctggctgg tttattgctg ataaatctgg agccggtgag cgtgggtctc gcggtatcat    5760
tgcagcactg gggccagatg gtaagccctc ccgtatcgta gttatctaca cgacggggag    5820
tcaggcaact atggatgaac gaaatagaca gatcgctgag ataggtgcct cactgattaa    5880
gcattggtaa ctgtcagacc aagtttactc atatatactt tagattgatt taaaacttca    5940
tttttaattt aaaaggatct aggtgaagat cctttttgat aatctcatga ccaaaatccc    6000
ttaacgtgag ttttcgttcc actgagcgtc agaccccgta gaaagatca aaggatcttc    6060
ttgagatcct ttttttctgc gcgtaatctg ctgcttgcaa acaaaaaaac caccgctacc    6120
agcggtggtt tgtttgccgg atcaagagct accaactctt tttccgaagg taactggctt    6180
cagcagagcg cagataccaa atactgttct tctagtgtag ccgtagttag gccaccactt    6240
caagaactct gtagcaccgc ctacatacct cgctctgcta atcctgttac cagtggctgc    6300
tgccagtggc gataagtcgt gtcttaccgg gttggactca agacgatagt taccggataa    6360
ggcgcagcgg tcgggctgaa cggggggttc gtgcacacag cccagcttgg agcgaacgac    6420
ctacaccgaa ctgagatacc tacagcgtga gctatgagaa agcgccacgc ttcccgaagg    6480
gagaaaggc ggacaggtat ccggtaagcg gcagggtcgg aacaggagag cgcacgaggg    6540
agcttccagg gggaaacgcc tggtatcttt atagtcctgt cgggtttcgc cacctctgac    6600
ttgagcgtcg atttttgtga tgctcgtcag ggggcggag cctatggaaa aacgccagca    6660
acgcggcctt tttacggttc ctggcctttt gctggccttt tgctcacatg ttctttcctg    6720
cgttatcccc tgattctgtg gataaccgta ttaccgcctt tgagtgagct gataccgctc    6780
gccgcagccg aacgaccgag cgcagcgagt cagtgagcga ggaagcggaa gagcgcccaa    6840
tacgcaaacc gcctctcccc gcgcgttggc cgattcatta atccaactgg cacgacaggt    6900
ttcccgactg gaaagcgggc agtgagcgca acgcaattaa tgtgagttag ctcactcatt    6960
aggcacccca ggctttacac tttatgcttc cggctcgtat gttgtgtgga attgtgagcg    7020
gataacaatt tcacacagga aacagctatg acatgattac gaattaa                 7067
```

<210> SEQ ID NO 14
<211> LENGTH: 12
<212> TYPE: PRT
<213> ORGANISM: Vicugna pacos

<400> SEQUENCE: 14

Gly Phe Thr Leu Asp Tyr Tyr Gly Ile Gly Trp Phe
1               5                   10

```
<210> SEQ ID NO 15
<211> LENGTH: 22
<212> TYPE: PRT
<213> ORGANISM: Vicugna pacos

<400> SEQUENCE: 15

Glu Arg Glu Ala Val Ser Tyr Ile Ser Ala Ser Ala Arg Thr Ile Leu
1               5                   10                  15

Tyr Ala Asp Ser Val Lys
            20

<210> SEQ ID NO 16
<211> LENGTH: 21
<212> TYPE: PRT
<213> ORGANISM: Vicugna pacos

<400> SEQUENCE: 16

Ala Arg Arg Arg Phe Ser Ala Ser Ser Val Asn Arg Trp Leu Ala Asp
1               5                   10                  15

Asp Tyr Asp Val Trp
            20

<210> SEQ ID NO 17
<211> LENGTH: 12
<212> TYPE: PRT
<213> ORGANISM: Vicugna pacos

<400> SEQUENCE: 17

Gly Ser Ile Ala Gly Phe Glu Thr Val Thr Trp Ser
1               5                   10

<210> SEQ ID NO 18
<211> LENGTH: 21
<212> TYPE: PRT
<213> ORGANISM: Vicugna pacos

<400> SEQUENCE: 18

Ser Leu Gln Trp Val Ala Ser Met Thr Lys Thr Asn Asn Glu Ile Tyr
1               5                   10                  15

Ser Asp Ser Val Lys
            20

<210> SEQ ID NO 19
<211> LENGTH: 6
<212> TYPE: PRT
<213> ORGANISM: Vicugna pacos

<400> SEQUENCE: 19

Lys Gly Pro Glu Leu Arg
1               5

<210> SEQ ID NO 20
<211> LENGTH: 12
<212> TYPE: PRT
<213> ORGANISM: Vicugna pacos

<400> SEQUENCE: 20

Gly Phe Thr Leu Asp Tyr Ser Ser Ile Gly Trp Phe
1               5                   10

<210> SEQ ID NO 21
<211> LENGTH: 22
<212> TYPE: PRT
<213> ORGANISM: Vicugna pacos
```

```
<400> SEQUENCE: 21

Glu Arg Glu Gly Val Ser Cys Ile Ser Ser Ser Gly Asp Ser Thr Lys
1               5                   10                  15

Tyr Ala Asp Ser Val Lys
            20

<210> SEQ ID NO 22
<211> LENGTH: 21
<212> TYPE: PRT
<213> ORGANISM: Vicugna pacos

<400> SEQUENCE: 22

Ala Ala Phe Arg Ala Thr Met Cys Gly Val Phe Pro Leu Ser Pro Tyr
1               5                   10                  15

Gly Lys Asp Asp Trp
            20

<210> SEQ ID NO 23
<211> LENGTH: 12
<212> TYPE: PRT
<213> ORGANISM: Vicugna pacos

<400> SEQUENCE: 23

Gly Phe Thr Phe Ser Asp Tyr Val Met Thr Trp Val
1               5                   10

<210> SEQ ID NO 24
<211> LENGTH: 21
<212> TYPE: PRT
<213> ORGANISM: Vicugna pacos

<400> SEQUENCE: 24

Gly Pro Glu Trp Ile Ala Thr Ile Asn Thr Asp Gly Ser Thr Met Arg
1               5                   10                  15

Asp Asp Ser Thr Lys
            20

<210> SEQ ID NO 25
<211> LENGTH: 16
<212> TYPE: PRT
<213> ORGANISM: Vicugna pacos

<400> SEQUENCE: 25

Ala Arg Gly Arg Val Ile Ser Ala Ser Ala Ile Arg Gly Ala Val Arg
1               5                   10                  15

<210> SEQ ID NO 26
<211> LENGTH: 127
<212> TYPE: PRT
<213> ORGANISM: Vicugna pacos

<400> SEQUENCE: 26

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60
```

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
            100                 105                 110

Asp Tyr Asp Val Trp Gly Arg Gly Thr Gln Val Ala Val Ser Ser
            115                 120                 125

<210> SEQ ID NO 27
<211> LENGTH: 111
<212> TYPE: PRT
<213> ORGANISM: Vicugna pacos

<400> SEQUENCE: 27

Gln Val Gln Leu Val Glu Ser Gly Gly Gly Leu Val Gln Thr Gly Gly
1               5                   10                  15

Ser Leu Arg Leu Ser Cys Ala Ser Ser Gly Ser Ile Ala Gly Phe Glu
            20                  25                  30

Thr Val Thr Trp Ser Arg Gln Ala Pro Gly Lys Ser Leu Gln Trp Val
            35                  40                  45

Ala Ser Met Thr Lys Thr Asn Asn Glu Ile Tyr Ser Asp Ser Val Lys
50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Gly Val Tyr Phe Cys Lys
                85                  90                  95

Gly Pro Glu Leu Arg Gly Gln Gly Ile Gln Val Thr Val Ser Ser
            100                 105                 110

<210> SEQ ID NO 28
<211> LENGTH: 127
<212> TYPE: PRT
<213> ORGANISM: Vicugna pacos

<400> SEQUENCE: 28

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
            35                  40                  45

Ser Cys Ile Ser Ser Ser Gly Asp Ser Thr Lys Tyr Ala Asp Ser Val
50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser
            115                 120                 125

<210> SEQ ID NO 29
<211> LENGTH: 121
<212> TYPE: PRT
<213> ORGANISM: Vicugna pacos -continued

```
<400> SEQUENCE: 29

Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser
        115                 120

<210> SEQ ID NO 30
<211> LENGTH: 113
<212> TYPE: PRT
<213> ORGANISM: Homo sapiens

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Phe Asp Tyr Trp Gly Gln Gly Thr Leu Val Thr Val Ser
            100                 105                 110

Ser

<210> SEQ ID NO 31
<211> LENGTH: 15
<212> TYPE: PRT
<213> ORGANISM: Homo sapiens

<400> SEQUENCE: 31

Tyr Phe Asp Tyr Trp Gly Gln Gly Thr Leu Val Thr Val Ser Ser
1               5                   10                  15

<210> SEQ ID NO 32
<211> LENGTH: 127
<212> TYPE: PRT
<213> ORGANISM: Artificial Sequence
<220> FEATURE:
<223> OTHER INFORMATION: MS humanized VHH peptide monomer 5D

<400> SEQUENCE: 32

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Phe Thr Leu Asp Tyr Tyr
            20                  25                  30
Gly Ile Gly Trp Phe Arg Gln Ala Pro Gly Lys Gly Leu Glu Ala Val
            35                  40                  45
Ser Tyr Ile Ser Ala Ser Ala Arg Thr Ile Leu Tyr Ala Asp Ser Val
            50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Arg Arg Phe Ser Ala Ser Ser Val Asn Arg Trp Leu Ala Asp
                100                 105                 110
Asp Tyr Asp Val Trp Gly Arg Gly Thr Leu Val Thr Val Ser Ser
                115                 120                 125

<210> SEQ ID NO 33
<211> LENGTH: 111
<212> TYPE: PRT
<213> ORGANISM: Artificial Sequence
<220> FEATURE:
<223> OTHER INFORMATION: MS humanized VHH peptide monomer E3

<400> SEQUENCE: 33

Glu Val Gln Leu Val Glu Ser Gly Gly Gly Leu Val Lys Pro Gly Gly
1               5                   10                  15
Ser Leu Arg Leu Ser Cys Ala Ala Ser Gly Ser Ile Ala Gly Phe Glu
            20                  25                  30
Thr Val Thr Trp Val Arg Gln Ala Pro Gly Lys Gly Leu Gln Trp Val
            35                  40                  45
Ser Ser Met Thr Lys Thr Asn Asn Glu Ile Tyr Ser Asp Ser Val Lys
            50                  55                  60
Gly Arg Phe Thr Ile Ser Arg Asp Asn Ala Lys Asn Thr Val Tyr Leu
65                  70                  75                  80
Gln Met Asn Ser Leu Arg Ala Glu Asp Thr Ala Val Tyr Tyr Cys Lys
                85                  90                  95
Gly Pro Glu Leu Arg Gly Gln Gly Thr Leu Val Thr Val Ser Ser
                100                 105                 110

<210> SEQ ID NO 34
<211> LENGTH: 121
<212> TYPE: PRT
<213> ORGANISM: Artificial Sequence
<220> FEATURE:
<223> OTHER INFORMATION: MS humanized VHH peptide monomer AA6

<400> SEQUENCE: 34

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Val Met Thr Trp Val Arg Gln Ala Pro Gly Lys Gly Pro Glu Trp Ile
            35                  40                  45
Ala Thr Ile Asn Thr Asp Gly Ser Thr Met Arg Asp Asp Ser Thr Lys
            50                  55                  60
Gly Arg Phe Thr Ile Ser Arg Asp Asn Ala Lys Asn Thr Leu Tyr Leu
65                  70                  75                  80
```

Gln Met Asn Ser Leu Arg Ala Glu Asp Thr Ala Val Tyr Tyr Cys Ala
                85                  90                  95

Arg Gly Arg Val Ile Ser Ala Ser Ala Ile Arg Gly Ala Val Arg Gly
            100                 105                 110

Gln Gly Thr Leu Val Thr Val Ser Ser
        115                 120

<210> SEQ ID NO 35
<211> LENGTH: 127
<212> TYPE: PRT
<213> ORGANISM: Artificial Sequence
<220> FEATURE:
<223> OTHER INFORMATION: MS humanized VHH peptide monomer AH3

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Val Arg Gln Ala Pro Gly Lys Gly Leu Glu Gly Val
        35                  40                  45

Ser Cys Ile Ser Ser Ser Gly Asp Ser Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Phe Arg Ala Thr Met Cys Gly Val Phe Pro Leu Ser Pro Tyr
            100                 105                 110

Gly Lys Asp Asp Trp Gly Gln Gly Thr Leu Val Thr Val Ser Ser
        115                 120                 125

<210> SEQ ID NO 36
<211> LENGTH: 354
<212> TYPE: PRT
<213> ORGANISM: Artificial Sequence
<220> FEATURE:
<223> OTHER INFORMATION: MShAA6-MShE3 kappa light chain of FZ001 binding
      agent

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Val Ile Ser Ala Ser Ala Ile Arg Gly Ala Val Arg Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Glu Val Gln Leu Val Glu Ser Gly

```
            130                 135                 140
Gly Gly Leu Val Lys Pro Gly Gly Ser Leu Arg Leu Ser Cys Ala Ala
145                 150                 155                 160

Ser Gly Ser Ile Ala Gly Phe Glu Thr Val Thr Trp Val Arg Gln Ala
                165                 170                 175

Pro Gly Lys Gly Leu Gln Trp Val Ser Ser Met Thr Lys Thr Asn Asn
                180                 185                 190

Glu Ile Tyr Ser Asp Ser Val Lys Gly Arg Phe Thr Ile Ser Arg Asp
                195                 200                 205

Asn Ala Lys Asn Thr Val Tyr Leu Gln Met Asn Ser Leu Arg Ala Glu
            210                 215                 220

Asp Thr Ala Val Tyr Tyr Cys Lys Gly Pro Glu Leu Arg Gly Gln Gly
225                 230                 235                 240

Thr Leu Val Thr Val Ser Ser Arg Thr Val Ala Ala Pro Ser Val Phe
                245                 250                 255

Ile Phe Pro Pro Ser Asp Glu Gln Leu Lys Ser Gly Thr Ala Ser Val
                260                 265                 270

Val Cys Leu Leu Asn Asn Phe Tyr Pro Arg Glu Ala Lys Val Gln Trp
            275                 280                 285

Lys Val Asp Asn Ala Leu Gln Ser Gly Asn Ser Gln Glu Ser Val Thr
            290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
                340                 345                 350

Glu Cys

<210> SEQ ID NO 37
<211> LENGTH: 599
<212> TYPE: PRT
<213> ORGANISM: Artificial Sequence
<220> FEATURE:
<223> OTHER INFORMATION: MShAH3-MSh5D heavy chain of FZ001 binding agent

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Ser
                20                  25                  30

Ser Ile Gly Trp Val Arg Gln Ala Pro Gly Lys Gly Leu Glu Gly Val
            35                  40                  45

Ser Cys Ile Ser Ser Ser Gly Asp Ser Thr Lys Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Phe Arg Ala Thr Met Cys Gly Val Phe Pro Leu Ser Pro Tyr
                100                 105                 110

Gly Lys Asp Asp Trp Gly Gln Gly Thr Leu Val Thr Val Ser Ser Gly
            115                 120                 125

Gly Gly Gly Ser Gly Gly Gly Ser Gly Gly Gly Gly Ser Glu Val
            130                 135                 140
```

```
Gln Leu Val Glu Ser Gly Gly Gly Leu Val Gln Pro Gly Gly Ser Leu
145                 150                 155                 160

Arg Leu Ser Cys Ala Ala Ser Gly Phe Thr Leu Asp Tyr Tyr Gly Ile
                165                 170                 175

Gly Trp Phe Arg Gln Ala Pro Gly Lys Gly Leu Glu Ala Val Ser Tyr
            180                 185                 190

Ile Ser Ala Ser Ala Arg Thr Ile Leu Tyr Ala Asp Ser Val Lys Gly
        195                 200                 205

Arg Phe Thr Ile Ser Arg Asp Asn Ala Lys Asn Ser Leu Tyr Leu Gln
210                 215                 220

Met Asn Ser Leu Arg Ala Glu Asp Thr Ala Val Tyr Tyr Cys Ala Arg
225                 230                 235                 240

Arg Arg Phe Ser Ala Ser Ser Val Asn Arg Trp Leu Ala Asp Asp Tyr
                245                 250                 255

Asp Val Trp Gly Arg Gly Thr Leu Val Thr Val Ser Ser Ala Ser Thr
            260                 265                 270

Lys Gly Pro Ser Val Phe Pro Leu Ala Pro Ser Ser Lys Ser Thr Ser
        275                 280                 285

Gly Gly Thr Ala Ala Leu Gly Cys Leu Val Lys Asp Tyr Phe Pro Glu
290                 295                 300

Pro Val Thr Val Ser Trp Asn Ser Gly Ala Leu Thr Ser Gly Val His
305                 310                 315                 320

Thr Phe Pro Ala Val Leu Gln Ser Ser Gly Leu Tyr Ser Leu Ser Ser
                325                 330                 335

Val Val Thr Val Pro Ser Ser Ser Leu Gly Thr Gln Thr Tyr Ile Cys
            340                 345                 350

Asn Val Asn His Lys Pro Ser Asn Thr Lys Val Asp Lys Arg Val Glu
        355                 360                 365

Pro Lys Ser Cys Asp Lys Thr His Thr Cys Pro Pro Cys Pro Ala Pro
370                 375                 380

Glu Leu Leu Gly Gly Pro Ser Val Phe Leu Phe Pro Pro Lys Pro Lys
385                 390                 395                 400

Asp Thr Leu Met Ile Ser Arg Thr Pro Glu Val Thr Cys Val Val Val
                405                 410                 415

Asp Val Ser His Glu Asp Pro Glu Val Lys Phe Asn Trp Tyr Val Asp
            420                 425                 430

Gly Val Glu Val His Asn Ala Lys Thr Lys Pro Arg Glu Glu Gln Tyr
        435                 440                 445

Asn Ser Thr Tyr Arg Val Val Ser Val Leu Thr Val Leu His Gln Asp
450                 455                 460

Trp Leu Asn Gly Lys Glu Tyr Lys Cys Lys Val Ser Asn Lys Ala Leu
465                 470                 475                 480

Pro Ala Pro Ile Glu Lys Thr Ile Ser Lys Ala Lys Gly Gln Pro Arg
                485                 490                 495

Glu Pro Gln Val Tyr Thr Leu Pro Pro Ser Arg Glu Glu Met Thr Lys
            500                 505                 510

Asn Gln Val Ser Leu Thr Cys Leu Val Lys Gly Phe Tyr Pro Ser Asp
        515                 520                 525

Ile Ala Val Glu Trp Glu Ser Asn Gly Gln Pro Glu Asn Asn Tyr Lys
530                 535                 540

Thr Thr Pro Pro Val Leu Asp Ser Asp Gly Ser Phe Phe Leu Tyr Ser
545                 550                 555                 560
```

```
Lys Leu Thr Val Asp Lys Ser Arg Trp Gln Gln Gly Asn Val Phe Ser
            565                 570                 575
Cys Ser Val Met His Glu Ala Leu His Asn His Tyr Thr Gln Lys Ser
        580                 585                 590
Leu Ser Leu Ser Pro Gly Lys
        595

<210> SEQ ID NO 38
<211> LENGTH: 1065
<212> TYPE: DNA
<213> ORGANISM: Artificial Sequence
<220> FEATURE:
<223> OTHER INFORMATION: polynucleotide sequence encoding the
      MShAA6-MShE3 kappa light chain of FZ001 binding agent

<400> SEQUENCE: 38
gaggtgcagc tggtggagtc cggggggaggc ttagttcagc tggggggtc cctgagactc      60 tcctgtgcag cctctggatt caccttcagt gactacgtga tgacctgggt ccgccaagct     120
ccagggaagg ggcctgagtg gatcgcaact attaatactg atgggagcac aatgcgcgac     180
gactccacaa agggccggtt caccatctcc agagacaacg ccaagaacac tctgtatctg     240
caaatgaaca gtctgagagc cgaggacact gctgtgtatt actgtgcaag aggccgggtg     300
atctctgctt ccgctatcag aggcgcagtc agaggccaag gaaccctggt caccgtctcg     360
agcggaggtg gcgggtcagg cggtggggga tctgaggggg gtggctccga ggtgcagctg     420
gtggagtctg ggggaggcct ggtcaagcct ggggggtccc tgagactctc ctgtgcagcc     480
tctggaagca tcgccggctt cgagaccgtg acctgggtcc gccaggctcc agggaagggg     540
ctgcagtggg tctcatccat gactaagact aataatgaga tatactcaga ctcagtgaag     600
ggccgattca ccatctccag agacaacgcc aagaacacag tgtatctgca aatgaacagc     660
ctgagagccg aggacacagc tgtgtattac tgtaagggac ctgagctgag gggccagggc     720
accctggtca ccgtctcgag ccgtacggtg gctgcaccat ctgtcttcat cttcccgcca     780
tctgatgagc agttgaaatc tggaactgcc tctgttgtgt gcctgctgaa taacttctat     840
cccagagagg ccaaagtaca gtggaaggtg ataacgcccc tccaatcggg taactcccag     900
gagagtgtca cagagcagga cagcaaggac agcacctaca gcctcagcag caccctgacg     960
ctgagcaaag cagactacga aaacacaaa gtctacgcct gcgaagtcac ccatcagggc    1020
ctgagctcgc ccgtcacaaa gagcttcaac aggggagagt gttag                   1065

<210> SEQ ID NO 39
<211> LENGTH: 1800
<212> TYPE: DNA
<213> ORGANISM: Artificial Sequence
<220> FEATURE:
<223> OTHER INFORMATION: polynucleotide sequence encoding the
      MShAH3-MSh5D heavy chain of FZ001 binding agent

<400> SEQUENCE: 39
gaggtgcagc tggtggagtc tgggggaggc ctggtacagc tggggggtc cctgagactc      60 tcctgtgcag cctctggatt caccttggac tattcttcca tcggctgggt ccgccaggct    120
ccagggaagg ggctggaggg ggtctcatgt attagtagta gtggtgatag cacaaagtac    180
gcagactccg tgaagggccg gttcaccatc tccagagaca attccaagaa caccttgtat    240
ctgcaaatga acagcctgag agccgaagac acggccgtat attactgtgc cgctttcagg    300
gctactatgt gcggcgtgtt ccctctgagc ccttacggca aggacgactg ggccaggga    360
```

-continued

```
acccctggtca ccgtctcgag cggaggtggc gggtcaggcg gtgggggatc tggagggggt    420
ggctccgagg tgcagctggt ggagtctggg ggaggcttgg tacagcctgg ggggtccctg    480
agactctcct gtgcagcctc tggattcacc ttggactact atggcatcgg ctggttccgc    540
caggctccag ggaaggggct ggaggccgtt tcatacatta gtgccagtgc ccggaccata    600
ctgtacgcag actctgtgaa gggccgattc accatctcca gagacaatgc caagaactca    660
ctgtatctgc aaatgaacag cctgagagcc gaggacaccg ctgtgtatta ctgtgcgaga    720
cggcgcttct ccgcttctag cgtgaataga tggctggccg acgactacga cgtgtgggc     780 cggggcaccc tggtcaccgt ctcctcagcg tcgaccaagg gcccatcggt cttcccgcta    840
gcaccctcct ccaagagcac ctctgggggc acagcggccc tgggctgcct ggtcaaggac    900
tacttccccg aacctgtgac ggtctcgtgg aactcaggcg ccctgaccag cggcgtgcac    960
accttcccgg ctgtcctaca gtcctcagga ctctactccc tcagcagcgt ggtgaccgtg   1020
ccctccagca gcttgggcac ccagacctac atctgcaacg tgaatcacaa gcccagcaac   1080
accaaggtgg acaagagagt tgagcccaaa tcttgtgaca aaactcacac atgcccaccg   1140
tgcccagcac ctgaactcct ggggggaccg tcagtcttcc tcttccccc aaaacccaag    1200 gacaccctca tgatctcccg gacccctgag gtcacatgcg tggtggtgga cgtgagccac   1260
gaagaccctg aggtcaagtt caactggtac gtggacggcg tggaggtgca taatgccaag   1320
acaaagccgc gggaggagca gtacaacagc acgtaccgtg tggtcagcgt cctcaccgtc   1380
ctgcaccagg actggctgaa tggcaaggag tacaagtgca aggtctccaa caaagccctc   1440 ccagcccca tcgagaaaac catctccaaa gccaaaggc agccccgaga ccacaggtg     1500 tacaccctgc ccccatcccg ggaggagatg accaagaacc aggtcagcct gacctgcctg   1560
gtcaaaggct tctatcccag cgacatcgcc gtggagtggg agagcaatgg gcagccggag   1620
aacaactaca agaccacgcc tcccgtgctg gactccgacg gctccttctt cctctatagc   1680
aagctcaccg tggacaagag caggtggcag caggggaacg tcttctcatg ctccgtgatg   1740
catgaggctc tgcacaacca ctacacgcag aagagcctct ccctgtcccc gggtaaatga   1800
```